US011905326B2

(12) United States Patent
Trinklein et al.

(10) Patent No.: US 11,905,326 B2
(45) Date of Patent: Feb. 20, 2024

(54) MULTISPECIFIC HEAVY CHAIN ANTIBODIES BINDING TO CD22 AND CD3

(71) Applicant: TeneoBio, Inc., Thousand Oaks, CA (US)

(72) Inventors: Nathan Trinklein, Thousand Oaks, CA (US); Udaya Rangaswamy, Thousand Oaks, CA (US); Suhasini Iyer, Thousand Oaks, CA (US); Kirthana Prabhakar, Thousand Oaks, CA (US); Harshad Ugamraj, Thousand Oaks, CA (US)

(73) Assignee: TeneoBio, Inc., Thousand Oaks, CA (US)

(*) Notice: Subject to any disclaimer, the term of this patent is extended or adjusted under 35 U.S.C. 154(b) by 173 days.

(21) Appl. No.: 16/900,586

(22) Filed: Jun. 12, 2020

(65) Prior Publication Data
US 2021/0047402 A1 Feb. 18, 2021

Related U.S. Application Data

(60) Provisional application No. 62/861,708, filed on Jun. 14, 2019.

(51) Int. Cl.
C07K 16/00 (2006.01)
C07K 16/28 (2006.01)
A61K 39/00 (2006.01)

(52) U.S. Cl.
CPC ...... C07K 16/2803 (2013.01); C07K 16/2809 (2013.01); A61K 2039/505 (2013.01); A61K 2039/545 (2013.01); C07K 2317/31 (2013.01); C07K 2317/52 (2013.01); C07K 2317/56 (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,500,362 A | 3/1996 | Robinson et al. |
| 5,585,097 A | 12/1996 | Bolt et al. |
| 5,821,337 A | 10/1998 | Carter et al. |
| 5,929,212 A | 7/1999 | Jolliffe et al. |
| 5,968,509 A | 10/1999 | Gorman et al. |
| 6,706,265 B1 | 3/2004 | Bolt et al. |
| 6,750,325 B1 | 6/2004 | Jolliffe et al. |
| 7,262,276 B2 | 8/2007 | Huang et al. |
| 7,381,803 B1 | 6/2008 | Weiner et al. |
| 7,541,513 B2 | 6/2009 | Bruggeman et al. |
| 7,635,472 B2 | 12/2009 | Kufer et al. |
| 7,728,114 B2 | 6/2010 | Mach et al. |
| 7,862,813 B2 | 1/2011 | Bjork |
| 8,236,308 B2 | 8/2012 | Kischel et al. |
| 8,367,888 B2 | 2/2013 | Bruggemann et al. |
| 8,883,150 B2 | 11/2014 | Craig et al. |
| 9,034,324 B2 | 5/2015 | Kalled et al. |
| 9,150,664 B2 | 10/2015 | Kufer et al. |
| 9,340,621 B2 | 5/2016 | Kufer et al. |
| 9,365,655 B2 | 6/2016 | Craig et al. |
| 11,434,299 B2 | 9/2022 | Force Aldred et al. |
| 11,505,606 B2 | 11/2022 | Trinklein et al. |
| 11,613,572 B2 | 3/2023 | Trinklein et al. |
| 2004/0229310 A1 | 8/2004 | Simmons |
| 2005/0048572 A1 | 3/2005 | Reilly et al. |
| 2007/0065437 A1 | 3/2007 | Elson et al. |
| 2007/0071675 A1 | 3/2007 | Wu et al. |
| 2007/0212733 A1 | 9/2007 | Martin |
| 2009/0098134 A1 | 4/2009 | Buelow |
| 2010/0122358 A1 | 5/2010 | Bruggemann et al. |
| 2013/0156769 A1 | 6/2013 | Kufer et al. |
| 2013/0273055 A1 | 10/2013 | Borges et al. |
| 2013/0273066 A1 | 10/2013 | Gokarn et al. |
| 2014/0056897 A1 | 2/2014 | Buelow et al. |
| 2014/0088295 A1 | 3/2014 | Smith et al. |
| 2015/0118251 A1 | 4/2015 | Deslandes et al. |
| 2015/0095412 A1 | 6/2015 | Wang |
| 2015/0266966 A1 | 9/2015 | Smith et al. |
| 2015/0337054 A1 | 11/2015 | Gardner, II et al. |
| 2015/0368351 A1 | 12/2015 | Vu et al. |
| 2015/0376287 A1 | 12/2015 | Vu et al. |
| 2016/0046724 A1 | 2/2016 | Brogdon et al. |
| 2016/0166689 A1 | 6/2016 | Adler et al. |
| 2016/0194399 A1 | 7/2016 | Irving et al. |
| 2016/0355591 A1 | 12/2016 | Goldenberg et al. |

(Continued)

FOREIGN PATENT DOCUMENTS

| | | |
|---|---|---|
| CA | 2828347 | 9/2012 |
| CN | 1889979 A | 1/2007 |

(Continued)

OTHER PUBLICATIONS

Rangaswamy et al. (J. of Clinical Oncology, vol. 36, No. 5, suppl. 26, Feb. 2018) (Year: 2018).*
Lefranc et al., "The Immunoglobulin FactsBook," Academic Press 2001.
Bruggemann et al., "Human Antibody Production in Transgenic Animals," (2014) Archivum Immunologiae et Therapie Experimentalis, Birkahaeser Verlag AG 63(2):101-108.
Menoret et al., "Transgenic Animals and Genetic Engineering Techniques," (2015) Transgenic Res 24:1079-1085.
Amiri et al., "A Novel Anti-CD22 scFv-apoptin Fusion Protein Induces Apoptosis in Malignant B-cells," (2017) AMB Express 7(112) Abstract.

(Continued)

Primary Examiner — Meera Natarajan
(74) Attorney, Agent, or Firm — Haynes and Boone LLP

(57) ABSTRACT

Multispecific, human heavy chain antibodies (e.g., Uni-Abs™) binding to CD22 and CD3 are disclosed, along with methods of making such antibodies, compositions, including pharmaceutical compositions, comprising such antibodies, and their use to treat disorders that are characterized by the expression of CD22.

97 Claims, 21 Drawing Sheets
Specification includes a Sequence Listing.

(56) References Cited

U.S. PATENT DOCUMENTS

| | | |
|---|---|---|
| 2017/0051068 A1 | 2/2017 | Pillarisetti et al. |
| 2017/0174770 A1 | 6/2017 | Bruggemann et al. |
| 2017/0275363 A1 | 9/2017 | Chang et al. |
| 2019/0225671 A1 | 7/2019 | van Schooten et al. |
| 2019/0263904 A1 | 8/2019 | Trinklein et al. |
| 2019/0352412 A1 | 11/2019 | Force Aldred et al. |
| 2020/0048348 A1 | 2/2020 | Trinklein et al. |
| 2020/0085839 A1 | 3/2020 | Sidransky et al. |
| 2020/0138865 A1 | 5/2020 | Kochenderfer et al. |
| 2020/0157232 A1 | 5/2020 | Trinklein et al. |
| 2020/0339685 A1 | 10/2020 | Schellenberger et al. |
| 2021/0047402 A1 | 2/2021 | Trinklein et al. |
| 2021/0095022 A1 | 4/2021 | Force Aldred et al. |
| 2021/0147564 A1 | 5/2021 | Trinklein et al. |
| 2021/0332133 A1 | 10/2021 | Force Aldred et al. |
| 2021/0340255 A1 | 11/2021 | Harris et al. |
| 2021/0355215 A1 | 11/2021 | Jorgensen et al. |
| 2021/0388106 A1 | 12/2021 | van Schooten et al. |
| 2021/0403587 A1 | 12/2021 | Buelow et al. |
| 2022/0025047 A1 | 1/2022 | Trinklein et al. |
| 2022/0089729 A1 | 3/2022 | Harris et al. |
| 2022/0195068 A1 | 6/2022 | van Schooten et al. |
| 2022/0332820 A1 | 10/2022 | Harris et al. |

FOREIGN PATENT DOCUMENTS

| | | |
|---|---|---|
| CN | 103619876 | 3/2014 |
| CN | 104114578 A | 10/2014 |
| CN | 104710528 A | 6/2015 |
| CN | 105384825 A | 3/2016 |
| CN | 106029098 A | 10/2016 |
| EP | 1210425 B1 | 4/2007 |
| EP | 1223964 B1 | 4/2007 |
| EP | 2762496 A1 | 8/2014 |
| EP | 1806143 B1 | 6/2016 |
| EP | 2780374 B1 | 8/2019 |
| EP | 2780375 B1 | 9/2019 |
| JP | 2012/504403 | 2/2012 |
| JP | 2012504403 A | 2/2012 |
| JP | 2013/528569 | 7/2013 |
| JP | 2013528569 A | 7/2013 |
| JP | 2014515598 | 7/2014 |
| JP | 2015/521032 | 7/2015 |
| JP | 2015521032 A | 7/2015 |
| RU | 2492186 C2 | 9/2013 |
| RU | 2561457 C2 | 8/2015 |
| RU | 2014147452 A | 6/2016 |
| WO | 1996/027011 A1 | 9/1996 |
| WO | 1996/032478 | 10/1996 |
| WO | 1997/034631 | 9/1997 |
| WO | 1998/050431 A2 | 11/1998 |
| WO | 2000/040716 A2 | 7/2000 |
| WO | 2001/012812 A2 | 2/2001 |
| WO | 2001/024811 A1 | 4/2001 |
| WO | 2001/024812 A1 | 4/2001 |
| WO | 2001/077342 A1 | 10/2001 |
| WO | 2001/087977 A2 | 11/2001 |
| WO | 2002/066516 A2 | 8/2002 |
| WO | 2004/106383 A1 | 12/2004 |
| WO | 2005/040220 A1 | 5/2005 |
| WO | 2005/061547 A2 | 7/2005 |
| WO | 2006/008548 | 1/2006 |
| WO | 2006/008548 A2 | 1/2006 |
| WO | 2007/042261 A2 | 4/2007 |
| WO | 2007/066109 | 6/2007 |
| WO | 2007/117600 | 10/2007 |
| WO | 2008/119565 A2 | 10/2008 |
| WO | 2008/119566 A2 | 10/2008 |
| WO | 2008/119567 A2 | 10/2008 |
| WO | 2009/132058 A2 | 10/2009 |
| WO | 2010/037835 A2 | 4/2010 |
| WO | 2010/037836 A2 | 4/2010 |
| WO | 2010/037837 A2 | 4/2010 |
| WO | 2010/037838 A2 | 4/2010 |
| WO | 2010/104949 A2 | 9/2010 |
| WO | 2010/109165 A2 | 9/2010 |
| WO | 2011/097603 | 8/2011 |
| WO | 2011/097603 A1 | 8/2011 |
| WO | 2012/066058 A1 | 5/2012 |
| WO | 2012/122512 | 9/2012 |
| WO | 2012/122528 | 9/2012 |
| WO | 2012/143498 | 10/2012 |
| WO | 2012/145714 A2 | 10/2012 |
| WO | 2012/163805 | 12/2012 |
| WO | 2013/072406 | 5/2013 |
| WO | 2013/072406 A1 | 5/2013 |
| WO | 2013/072415 | 5/2013 |
| WO | 2014/022540 | 2/2014 |
| WO | 2014/022540 A1 | 2/2014 |
| WO | 2014/047231 A1 | 3/2014 |
| WO | 2014/068079 A1 | 5/2014 |
| WO | 2014/089335 A2 | 6/2014 |
| WO | 2014/093908 | 6/2014 |
| WO | 2014/122144 | 8/2014 |
| WO | 2014/140248 | 9/2014 |
| WO | 2015/095412 A1 | 6/2015 |
| WO | 2015/121383 A1 | 8/2015 |
| WO | 2015/130416 A1 | 9/2015 |
| WO | 2015/149077 A1 | 10/2015 |
| WO | 2016/014974 | 1/2016 |
| WO | 2016/062990 A1 | 4/2016 |
| WO | 2016/079081 | 5/2016 |
| WO | 2016/079081 A1 | 5/2016 |
| WO | 2016/079177 | 5/2016 |
| WO | 2016/079177 A1 | 5/2016 |
| WO | 2016079177 | 5/2016 |
| WO | 2016/094304 A2 | 6/2016 |
| WO | 2016/113555 A1 | 7/2016 |
| WO | 2016/187546 A1 | 11/2016 |
| WO | 2017/023761 A1 | 2/2017 |
| WO | 2017/025038 A1 | 2/2017 |
| WO | 2017/031104 A1 | 2/2017 |
| WO | 2015/063339 | 5/2017 |
| WO | 2017/081211 A2 | 5/2017 |
| WO | 2017/134134 | 8/2017 |
| WO | 2017/223111 | 12/2017 |
| WO | 2018/039180 | 3/2018 |
| WO | 2018/039180 A1 | 3/2018 |
| WO | 2018/052503 | 3/2018 |
| WO | 2018/052503 A1 | 3/2018 |
| WO | WO2018/052503 | * 3/2018 |
| WO | 2018/119215 | 6/2018 |
| WO | 2018/237006 | 12/2018 |
| WO | 2018/237037 | 12/2018 |
| WO | 2019/000223 A1 | 1/2019 |
| WO | 2019/006072 | 1/2019 |
| WO | 2019/055689 | 3/2019 |
| WO | 2019/075413 A1 | 4/2019 |
| WO | 2019/126756 | 6/2019 |
| WO | WO2019/126756 | * 6/2019 |
| WO | 2019/133761 | 7/2019 |
| WO | 2020/018922 | 1/2020 |
| WO | 2020/061478 | 3/2020 |
| WO | 2020/087065 | 4/2020 |
| WO | 2020/206330 | 10/2020 |
| WO | 2010/032061 | 12/2020 |
| WO | 2020/252366 | 12/2020 |
| WO | 2021/127489 | 6/2021 |
| WO | 2021/222578 | 11/2021 |
| WO | 2021/222616 | 11/2021 |
| WO | 2021/228783 A1 | 11/2021 |
| WO | 2022/006316 | 1/2022 |
| WO | 2022/109010 | 5/2022 |
| WO | 2022/183074 | 9/2022 |
| WO | 2022/183101 | 9/2022 |
| WO | 2022/212848 | 10/2022 |
| WO | 2022/216864 | 10/2022 |
| WO | 2022/221698 | 10/2022 |

(56) References Cited

FOREIGN PATENT DOCUMENTS

| WO | 2022/271987 | 12/2022 |
|----|-------------|---------|
| WO | 2023/004197 | 1/2023  |

OTHER PUBLICATIONS

Buelow et al., "Development of a Fully Human T Cell Antibody Fragments and Mouse Monoclonal Antibodies," (1999) Biochimica et Biophysica Acta 1431:37-46.

Ghahroudi et al., "Selection and Identification of Single Domain Antibody Fragments from Camel Heavy-chain Antibodies," (1997) FEBS Letters 414:521-526.

Bruggemann et al., "Heavy-Chain-Only Antibody Expression and B-Cell Development in the Mouse," (2006) Crit. Rev. Immunol. 26(5):377-90.

Zou et al., "Heavy Chain-Only Antibodies are Spontaneously Produced in Light Chain-Deficient," (2007) J Exp Med 204(13): 3271-3283.

Iri-Sofla et al., "Nanobody-based Chimeric Receptor Gene Integration in Jurkat Cells Mediated by PhiC31 Integrase," (2011) Experimental Cell Research 317:2630-2641.

Jamnani et al., "T Cells Expressing VHH-directed Oligoclonal Chimeric HER2 Antigen Receptors: Towards Tumor-directed Oligoclonal T Cell Therapy," (2014) Biochimica et Biophysica Acta 1840:378-386A.

Duncan et al., "Localization of the binding site for the human high-affinity Fc receptor on IgG ," (1988) Nature 332:563-564.

Canfield et al"The Binding Affinity of Human IgG for its High Affinity Fc Receptor Is Determined by Multiple Amino Acids in the CH2 Domain and Is Modulated by the Hinge Region," J. Exp. Med. 173:1483-1491.

Armour et al., "Recombinant human IgG molecules lacking Fcγ receptor I binding and monocyte triggering activities," (1999) Eur J Immunol. 29(8):2613-2624.

Boesch et al., "Highly parallel characterization of IgG Fc binding interactions," (2014) MAbs 6(4):915-927.

Hamers-Casterman et al., "Naturally Occurring Antibodies Devoid of Light Chains," (1993) Letters to Nature 363:446-448.

Desmyter et al., "Antigen Specificity and High Affinity Binding Provided by One Single Loop of a Camel Single-domain Antibody," (2001) Journal of Biological Chemistry 276(28):26285-26290.

Menoret et al., "Characterization of Immunoglobulin Heavy Chain Knockout Rats," (2010) European Journal Immunology 40:2932-2941.

Alderson et al., "CAT-8015: A Second-Generation Pseudomonas Exotoxin A—Based Immunotherapy Targeting CD22-Expressing Hematologic Malignancies," (2009) Clinical Cancer Research 15(3):832-839.

Rangaswamy et al., "A Novel T-cell Antibody Platform for Efficient T-cell Mediated Killing of Tumor Cells with Minimal Cytokine Release," (2018) Journal of Clinical Oncology 36(5):Supplement 26, Abstract.

Kim et al., ""Mutational approaches to improve the biophysical properties of human single-domain antibodies", (2014) Biochimica Et Biophysica ACTA (BBA)—Proteins & Proteomics, Elseviern Netherlands (2014) 1844(11):1983-2001".

Aalberse et al., "IgG4 Breaking the Rules," (2002) Immunology 105:9-19.

Goel et al., "Plasticity within the Antigen-Combining Site May Manifest as Molecular Mimicry in the Humoral Immune Response," (2004) J Immunol 173(12): 7358-7367.

Ippoliti et al., "Immunomodulation with rabbit anti-thymocyte globulin in solid organ transplantation," (2015) World Journal of Transplantation 5(4):261-266.

Llyod et al., Modelling the human immune response: performance of a $10^{11}$ human antibody repertoire against a broad panel of therapeutically relevant antigens, (2009) Protein Engineering, Design & Selection 22(3):159-168.

Rabia et al., "Understanding and overcoming trade-offs between antibody affinity, specificity, stability and solubility," (2018) Biochemical Engineering Journal 137:365-374.

Tam et al., "Functional, Biophysical and Structural Characterization of Human IgG1 and IgG4 Fc Variants with Ablated Immune Functionality," (2017) Antibodies 6(12): 1-34.

Adams et al., "Prolonged in Vivo Tumour Retention of a Human Diabody Targeting the Extracellular Domain of Human HER2/neu," (1998) British Journal of Cancer 77(9):1405-1412.

Ali et al., "T cells expressing an anti-B-cell maturation antigen chimeric antigen receptor cause remissions of multiple myeloma," (2016) Blood 128(13):1688-1700.

Almagro "Identification of differences in the specificity-determining residues of antibodies that recognize antigens of different size: implications for the rational design of antibody repertoires," (2004) Journal of Molecular Recognition 17(2):132-143.

Anonymous (TeneoBio, Inc.), "A Study of TNB-383B in Subjects with Relapsed or Refractory Multiple Myeloma," (2019) retrieved from the Internet on May 1, 2019 from URL: https://clinicaltrials.gov/ct2/show/NCT03933735.

Anonymous, "Antibody Therapeutics—TeneoBio's Next Generation of Multispecific Antibody Therapeutics," (2018) retrieved from the Internet at: https://drug-dev.com/antibody-therapeutics-teneobios-next-generation-of-multispecific-antibody-therapeutics/.

Anonymous, "Flow Cytometry Antibody: CD3e Cat. No. CT026-R301, SinoBiological Inc,—Antibody-Catalogue," (2017) Sinobiological, Inc., Retrieved from the Internet: <https://www.sinobiological.com/antibodies/human-cynomolgus-cd3d-cd3e-ct026-r301>.

Armitage, "A clinical evaluation of the International Lymphoma Study Group classification of non-Hodgkin's lymphoma," (1997) Blood 89(11): 3909-3918.

Armour et al., "Recombinant human IgG molecules lacking Fcγ receptor I binding and monocyte triggering activities," (1999) Eur J Immunol. 29(8):2613-2624.

Arnett et al., "Crystal Structure of a Human CD3-epsilon/delta Dimer in Complex with a UCHT1 Single-chain Antibody Fragment," (2004) Proc Natl Acad Sci USA 101(46):16268-16273.

Baas et al., "Superhuman Mice," (2014) Science-Business exchange 7(17):1-2.

Baeuerle et al., "Bispecific T-cell engaging antibodies for cancer therapy," (2009) Cancer Research 69(12):4941-4944.

Baeuerle et al., "BiTE: A new class of antibodies that recruit T-cells," (2008) Drugs of the Future 33(2):137-147.

Baeuerle et al., "BiTE: Teaching antibodies to engage T-cells for cancer therapy," (2009) Current Opinion in Molecular Therapeutics 11(1):22-30.

Bargou et al., "Tumor Regression in Cancer Patients by Very Low Doses of a T Cell-Engaging Antibody," (2008) Science 321:974-977.

BCMA (Vicky-1): ALX-804-151 product datasheet, Enzo Life Sciences, last revised Dec. 20, 2019.

BCMA (Vicky-1): sc-57037 datasheet, Santa Cruz Biotechnology, https://datasheets.scbt.com/sc-57037.pdf (last visited Apr. 12, 2022).

Bellucci et al., "Complete response to donor lymphocyte infusion in multiple myeloma is associated with antibody responses to highly expressed antigens," (2004) Blood 103(2):656-663.

Bellucci et al., "Complete response to donor lymphocyte infusion in patients with multiple myeloma is associated with antibody response to BCMA, a plasma cell membrane receptor" (2003) Blood 102(11):192a-193a.

Bellucci et al., "Graft-versus-tumor response in patients with multiple myeloma is associated with antibody response to BCMA, a plasma-cell membrane receptor," (2005) Blood 105(10):3945-3950.

Bluemel et al., "Epitope Distance to the Target Cell Membrane and Antigen Size Determine the Potency of T Cell-mediated Lysis by BiTE Antibodies Specific for a Large Melanoma Surface Antigen," (2010) Cancer Immunol Immunother 59(8):1197-1209.

Bodmer et al., "Review—The molecular architecture of the TNF superfamily," (2002) Trends in Biochemical Sciences 27(1):19-26.

Borchmann et al., "Phase 1 trial of the Novel Bispecific Molecule H22xKi-4 in Patients with Refractory Hodgkin Lymphoma," (2002) Blood 100(9):3101-3107.

(56) References Cited

OTHER PUBLICATIONS

Bossen et al., "Review, Baff, April and their receptors: Structure, function and signaling," (2006) Seminars in Immunology 18:263-275.
Bruggemann et al., "Heavy-Chain-Only Antibody Expression and B-Cell Development in the Mouse," (2006) Crit. Rev. Immunol. 26(5):377-390.
Bruggemann et al., "Human Antibody Production in Transgenic Animals," (2015) Archivum Immunologiae et Therapiae Experimentalis, Birkhaeuser Verlag AG 63:101-108.
Buelow et al., "Development of a fully human T cell engaging bispecific antibody for the treatment of multiple myeloma," (2017) J Clin Oncol vol. 35 Supplement.
Buelow et al., "TNB3838.0001: A Multicenter, Phase 1, Open-Label, Dose-Escalation And Expansion Study of TNB-3838, a Bispecific Antibody Targeting BCMA in Subjects with Relapsed or Refractory Multiple Myeloma," (2019) Blood 134(Supplement 1):1874.
Canfield et al., "The Binding Affinity of Human IgG for its High Affinity Fc Receptor Is Determined by Multiple Amino Acids in the CH2 Domain and Is Modulated by the Hinge Region," J. Exp. Med. 173(6): 1483-1491.
Caraccio et al., "Bispecific Antibodies for Multiple Myeloma: A Review of Targets, Drugs, Clinical Trials and Future Directions," (2020) Frontiers in Immunology 11(50):1-25.
Carpenter et al., "B-cell Maturation Antigen Is a Promising Target for Adoptive T-cell Therapy of Multiple Myeloma," (2013) Clin Cancer Res 19(8):2048-2060.
Chames et al., "Bispecific antibodies for cancer therapy," (2009) Current Opinion in Drug Discovery & Development 12(2): 276-283.
Chames et al., "Bispecific Antibodies for Cancer Therapy," (2009) mAbs 1(6):539-547.
Chassaing et al., "Dextran Sulfate Sodium (DSS)-Inducted Colitis in Mice," (2014) Current Protocols in Immunology 15(25):1-14.
Chatenoud et al., "CD3 Monoclonal Antibodies: A First Step Towards Operational Immune Tolerance in the Clinic," (2012) Rev Diabet Stud 9(4):372-381.
Chen et al., "Fusion protein linkers: Property, design and functionality," (2013) Advanced Drug Delivery Reviews 65(10):1357-1369.
Chini et al., "The Pharmacology of CD38/NADase: An Emerging Target in Cancer and Diseases of Aging," (2018) Trends in Parmacological Sciences 39(4):424-436.
Choi et al., "Bispecific antibodies engage T-cells for antitumor Immunotherapy, " (2011) Expert Opinion on Biological Therapy 11(7): 843-853.
Chothia et al., "Conformations of immunoglobulin hypervariable regions," (1989) Nature 342:877-883.
Chothia et al., "Canonical structures for the hypervariable regions of immunoglobulins," (1987) Journal of Molecular Biology 196(4):901-917.
Chou et al., "Quantitative Analysis of Dose-Effect Relationships: The Combined Effects of Multiple Drugs or Enzyme Inhibitors," (1984) Hopkins University School of Medicine 22:27-55.
Clayton et al., "CD3η and CD3ζ are alternatively spliced products of a common genetic locus and are transcriptionally and/or post-transcriptionally regulated during T-cell development," (1991) Proceedings of the National Academy of Sciences USA 88:5202-5206.
Clynes et al., "Fc Receptors are Required in Passive and Active Immunity to Melanoma," (1998) PNAS (USA) 95(2):652-656.
Concepcion et al., "Label-Free Detection of Biomolecular Interactions Using BioLayer Interferometry for Kinetic Characterization," (2009) Combinatorial Chemistry & High Throughput Screening 12(8):791-800.
Conference abstracts of the International Myeloma Society 19th Annual Meeting and Exposition (2022).
Cui et al., "Targeted Integration in Rat and Mouse Embryos with Zinc-finger Nucleases," (2011) Nature Biotechnology 29(1):64-67.
Dai et al., "Chimeric Antigen Receptors Modified T-Cells for Cancer Therapy," (2016) J Natl Cancer Inst 108(7):dvj439.

Dasilva, "Abstract 34: A Met x MET Bispecific Antibody that Induces Receptor Degradation Potently Inhibits the Growth of MET-addicted Tumor Xenografts," (2017) Cancer Research 77(13 Suppl): 34-34.
ClinicalTrials.gov, "Study of CC-93269, a BCMA x CD3 T Cell Engaging Antibody, In Participants with Relapsed and Refectory Multiple Myeloma", (2022) ID: NCT03486067; 3 pages.
Declaration Nathan D. Trinklein, Ph.D. in EP 2780375 Opposition, EP Application No. 12805432.7.
Declaration of Dr. Rui Zhu, PhD, dated Jun. 9, 2020 in EP 2780375 Opposition, EP Application No. 12805432.7.
Declaration of Kara Olson, dated May 14, 2021 in EP 2780375 Opposition, EP Application No. 12805432.7.
Declaration of Kevin C. Lindquist in EP 2780375 Opposition, EP Application No. 12805432.7.
Desmyter et al., "Antigen Specificity and High Affinity Binding Provided by One Single Loop of a Camel Single-domain Antibody," (2001) Journal of Biological Chemistry, American Society for Biochemistry and Molecular Biology 276(28):26285-26290.
DiLillo et al., "A BCMAxCD3 Bispecific T Cell-engaging Antibody Demonstrates Robust Antitumor Efficacy Similar to that of Anti-BCMA Car T Cells," (2020) Blood Advances 5(5):1291-1304.
Dillon et al., "An APRIL to remember: Novel TNF ligands as therapeutic targets," (2006) Nat Rev 5(3):235-246.
Dimopoulos et al., "Daratumumab, Lenalidomide, and Dexamethasone for Multiple Myeloma," (2016) New England Journal of Medicine 375(14):1319-1331.
Dondelinger et al., "Understanding the Significance and Implications of Antibody Numbering and Antigen-binding Surface/Residue Definition," (2018) Frontiers in Immunology 9:1-15.
Dooley et al., "Selection and Characterization of Naturally Occurring Single-domain (IgNAR) Antibody Fragments from Immunized Sharks by Phage Display," (2003) Molecular Immunology 40(1):25-33.
Duncan et al., "Localization of the binding site for the human high-affinity Fc receptor on IgG," (1988) Nature 332:563-564.
Durben et al., "Characterization of a Bispecific FLT3 X CD3 Antibody in an Improved, Recombinant Format for the Treatment of Leukemia," (2015) Molecular Therapy 23(4):648- 655.
Excerpt of examination report from EP Application No. 12805432.7, dated Oct. 31, 2016, p. 1.
Opposition to European Patent No. EP 2780375 B1, Opponent 06: James Poole Limited, Experimental Report 1: Cytotoxic Activity.
Figure 6.8 of Antigen receptor structure and signaling pathways, Immunobiology: The Immune System in Health and Disease. 5th Edition, Janeway CA Jr, Travers P, Walport M, et al., New York: Garland Science; 2001.
Fitzgerald et al., "The Cytokine FactsBook," 2nd ed. (2001) Academic Press, pp. 151-152.
Foote et al., "Antibody Framework Residues Affecting the Conformation of the Hypervariable Loops," (1992) Journal of Molecular Biology 224(2):487-499.
Force Aldred et al., "Winning the Numbers Game: Novel Multi-specific Therapeutics from a Diverse Collection of Human Domain Antibodies," (2016) retrieved from the Internet at: https://2019.lakepharma.com/files/symposiums/Winning%20the%20Numbers%20Game%20- %20Novel%20Multi-specific%20Therapeutics%20from%20a%20Diverse%20Collection%20of%20Human%20Domain %20Antibodies%20-%20Shelley%20Force%20Aldred.pdf [Inactive link].
Frenken et al., Isolation of Antigen Specific Llama $V_{HH}$ Antibody Fragments and Their High Level Secretion by *Saccharomyces Cerevisiae*, (2000) J Biotechnol 78:11-21.
Fry et al., "CD22-targeted Car T Cells Induce Remission in B-ALL that is Naive or Resistant to CD19-targeted CAR Immunotherapy," (2018) Nature Medicine 24(1):20-28.
Gazzano-Santoro et al., "A non-radioactive complement-dependent cytotoxicity assay for anti-CD20 monoclonal antibody," (1996) Journal of Immunological Methods 202(2):163-171.
GenBank Accession No. AB052772.1, "*Homo sapiens* gene for BCMA, complete cds," available at https://www.ncbi.nlm.nih.gov/nuccore/AB052772 (last visited Apr. 23, 2020).

(56) References Cited

OTHER PUBLICATIONS

GenBank Accession No. NM_000733, "*Homo sapiens* CD3e molecule (CD3E), mRNA", available at https://www.ncbi.nlm.nih.gov/nuccore/NM_000733.3 (last visited Apr. 23, 2020).
Gershoni et al., "Epitope Mapping—The First Step in Developing Epitope-based Vaccines," (2007) Biodrugs, Adis International, Ltd. NZ 21(3):145-156.
Geurts et al., "Knockout Rats via Embryo Microinjection of Zinc-Finger Nucleases," (2009) Science 325(5939):433.
Ghahroudi et al., "Selection and Identification of Single Domain Antibody Fragments from Camel Heavy-chain Antibodies," (1997) FEBS Lett 414:521-526.
Giavridis et al., "Car T cell—induced cytokine release syndrome is mediated by macrophages and abated by IL-1 blockade," (2018) Nature Medicine 24(6):731-738.
Glennie et al., "Preparation and Performance of Bispecific F(ab' gamma)2 Antibody Containing Thioether-linked Fab' gamma Fragments," (1987) Journal of Immunology 139(7):2367-2375.
Goldstein et al., "AMG 701 induces cytotoxicity of multiple myeloma cells and depletes plasma cells in cynomoglus monkeys," (2020) Blood Advances 4(17): 4180—4194.
Gras et al., "BCMAp: an integral membrane protein in the Golgi apparatus of human mature B lymphocytes," (1995) Int. Immunol. 7(7):1093-1106.
Gruss et al., "Structural and Biological Features of the TNF Receptor and TNF Ligand Superfamilies: Interactive Signals in the Pathobiology of Hodgkin's Disease," (1996) Ann Oncol, 7 (Suppl 4):S19-S26.
Gust et al., "Endothelial Activation and Blood-Brain Barrier Disruption in Neurotoxicity after Adoptive Immunotherapy with CD19 Car-T Cells," (2017) Cancer Discovery 7(12):1405-1419.
Guy et al., "Organization of Proximal Signal at the TCR:CD3 Complex," (2009) Immunol Rev 232(1):1-22.
Haffner et al., "Discovery, Synthesis and Biological Evaluation of Thiazoloquin(az)olin(one)es as Potent CD38 Inhibitors," (2015) Journal of Medical Chemistry 58:3548-3571.
Hagner et al., "Targeting B-Cell Maturation Antigen (BCMA) with CC-93269, a 2+1 T Cell Engager, Elicits Significant Apoptosis in Diffuse Large B-Cell Lymphoma Preclinical Models," (2019) Preclinical Blood 2019, 134(Suppl. 1):1580.
Hamers-Casterman et al., "Naturally Occurring Antibodies Devoid of Light Chains," (1993) Nature 363:446-448.
Hamilton et al., "Humanization of Yeast to Produce Complex Terminally Sialylated Glycoproteins," (2006) Science 313(8):1441-1443.
Hanes et al., "New advances in microsphere-based single-dose vaccines," (1997) Advanced Drug Delivery Reviews 28(1):97-119.
Hipp et al., "A Novel BCMA/CD3 Bispecific T-cell Engager for the Treatment of Multiple Myeloma Induces Selective Lysis in Vitro and in Vivo," (2017) 31(8):1743-1751.
Hlavacek et al., "Steric Effects on Multivalent Ligand-Receptor Binding: Exclusion of Ligand Sites by Bound Cell Surface Receptors," (1999) Biophysical Journal 76(6):3031-3043.
Honegger, "Yet Another numbering scheme for immunoglobulin variable domains: an automatic modeling and analysis tool," (2001) Journal of Molecular Biology 309(3):657-670.
Honemann et al., 'A Novel Recombinant Bispecific Single-chain Antibody, bscWue-1 x CD3, Induces T-cell-mediated Cytotoxicity Towards Human Multiple Myeloma Cells, (2004) Leukemia 18(3):636-644.
Hotzel et al., "A strategy for risk mitigation of antibodies with fast clearance," (2012) mAbs 4(6):753-760.
Hymowitz et al., "Structures of APRIL-Receptor Complexes," (2005) Journal of Biological Chemistry 280(8):7218-7227.
Iri-Sofla et al., "Nanobody-based chimeric receptor gene integration in Jurkat cells mediated by PhiC31 integrase," (2011) Experimental Cell Research 317(18):2630-2641.
Jabbour et al., "Monoclonal Antibodies in Acute Lymphoblastic Leukemia," (2015) Blood 125(26):2010-2016.
Jackson et al., "Driving CAR T-cells forward," (2016) Nature Reviews Clinical Oncology 13:370-383.
Jamnani et al., "T cells expressing VHH-directed oligoclonal chimeric HER2 antigen receptors: Towards tumor-directed oligoclonal T cell therapy," (2014) Biochim Biophys Acta 1840(1):378- 386.
Janssens et al., "Generation of Heavy-chain-only Antibodies in Mice," (2006) Proceedings of the National Academy of Sciences of the USA 103(41):15130-15135.
Jaton et al., "Recovery of antibody activity on reoxidation of completely reduced polyalanyl heavy chain and its Fd fragment derived from anti-2,4-dinitrophenyl antibody," (1968) Biochemistry 7(12):4185-4195.
Jemal et al., "Cancer Statistics, 2008," ACS Journals (2008) 58(2):71-96.
Kanda et al., "Establishment of a GDP-mannose 4,6-dehydratase (GMD) knockout host cell line: A new strategy for generating completely non-fucosylated recombinant therapeutics," (2007) Journal of Biotechnology 130(3):300-310.
Kaneko et al., "Anti-inflammatory Activity of Immunoglobulin G Resulting from Fc Sialylation," (2006) Science 313(5787)670-673.
Kapoor et al., "Anti-CD20 Monoclonal Antibody Therapy in Multiple Myeloma," (2008) Br J Haematol 141(2):135-148.
Kjer-Nielsen et al., "Crystal Structure of the Human T Cell Receptor CD3Ey Heterodimer Complexed to the Therapeutic mAb OKT3," (2004) Proceedings of the Nation 101(20):7675-7680.
Koarada et al., "Autoantibody-Producing RP105- B Cells, from Patients with Systematic Lupus Erythematosus, showed more Preferential Expression of BCMA Compared with BAFF-R than Normal Subject," (2010) Rheumatology 49(4):662-670.
Kohler et al., "Continuous cultures of fused cells secreting antibody of predefined specificity," (1975) Nature 256:495-497.
Kontermann "Bispecific Antibodies" (2011), Springer-Verlag Berlin Heidelberg, Chapters 1, 2, 7, 11, 13, 14 and 15.
Kontermann, "Invited review—Recombinant bispecific antibodies for cancer therapy," (2005) Acta Pharmacologica Sinica 26(1):1-9.
Kufer et al., "Review—A revival of bispecific antibodies," (2004) Trends in Biotechnology 22(5):238-244.
Kuhns et al., "Deconstructing the Form and Function of the TCR/CD3 Complex," (2006) Immunity 24(2):133-139.
Kumar et al., "Improved survival in multiple myeloma and the impact of novel therapies," (2008) Blood 111(5):2516-2520.
Kumar et al., "International Myeloma Working Group consensus criteria for response and minimal residual disease assessment in multiple myeloma," (2016) The Lancet Oncology 17(8):e328-e346.
Langer, "New Methods of Drug Delivery," (1990) Science 249(4976):1527-1533.
Leiba et al., "Activation of B cell maturation antigen (BCMA) on human multiple myeloma cells by a proliferation-inducing ligand (APRIL) promotes myeloma cell function in the bone marrow microenvironment," (2007) Blood 110(11):1503.
Levine, "Mechanisms of Soluble Cytokine Generation," (2004) J Immunol 173(9):5343-8.
Lindhofer et al., "Preferential Species-restricted Heavy/Light Chain Pairing in Rat/Mouse Quadromas. Implications for a Single-step Purification of Bispecific Antibodies," (1995) The Journal of Immunology, 155(1):219-225.
Link et al., "Anti-CD3-Based Bispecific Antibody Designed for Therapy of Human B-Cell Malignancy can Induce T-cell Activation by Antigen-dependent and Antigen-independent Mechanisms," (1998) Int. J. Cancer 77:251-256.
Liu et al., "Ligand-receptor binding revealed by the TNF family member TALL-1," (2003) Nature 423:49-56.
Lund et al., "Expression and characterization of truncated forms of humanized L243 IgG1," (2000) European Journal of Biochemistry 267(24):7246-7256.
MAB193 data sheet, Human BCMA/TNFRSF17 Antibody, R&D Systems, last revised Feb. 7, 2018.
Mack et al., "A Small Bispecific Antibody Construct Expressed as a Functional Single-chain Molecule with High Tumor Cell Cytotoxicity," (1995) PNAS 92:7021-7025.
Mailankody et al., "T-Cell Engagers—Modern Immune-Based Therapies for Multiple Myeloma," (2022) N Engl J Med 387(6): 558-561.

(56) References Cited

OTHER PUBLICATIONS

Mariuzza et al., "The Structural Basis of Antigen-Antibody Recognition," (1987) Ann Rev Biophys Biophys Chem 16:139-159.
Menoret et al., "Characterization of Immunoglobulin Heavy Chain Knockout Rats," (2010) European Journal Immunology 40(1):2932-2941.
Ménoret et al., Transgenic Animals and Genetic Engineering Techniques, Nantes, France, Jul. 2-3, 2015 (2015) Transgenic Res 24:1079-1085.
Merchant et al., "An Efficient Route to Human Bispecific IgG," (1998) Nature Biotechnology, Gale Group, Inc. 16(7):677-684.
Mikkilineni et al., "Chimeric antigen receptor T-cell therapies for multiple myeloma," (2017) Blood 130(24): 2594-2602.
Miller et al., "Design, Construction, and In Vitro Analyses of Multivalent Antibodies," (2003) Jour. of Immunology 170(9):4854-4861.
Moreau et al., "Teclistamab in Relapsed or Refractory Multiple Myeloma," (2022) N Engl J Med 387(6)495-505.
Moreaux et al., "APRIL and TACI interact with syndecan-1 on the surface of multiple myeloma cells to form an essential survival loop, " (2009) Eur J Heamatol 83(2):119-129.
Müller et al., "Bispecific antibodies for cancer immunotherapy," (2010) Biodrugs 24(2):89-98.
Muller et al., "Recombinant bispecific antibodies for cellular cancer immunotherapy," (2006) Current Opinion in Molecular Therapeutics 9(4):319-326.
Muyldermans "Single domain camel antibodies: current status," (2001) J Biotechnol 74(4):277-302.
Neisig et al., "Assembly of the T-Cell Antigen Receptor," (1993) Journal of Immunology 151:870-879.
Nguyen et al., "Functional Heavy-Chain Antibodies in Camelidae," (2001) Advances in Immunology 79:261-296.
Nguyen et al., "Heavy-chain Only Antibodies Derived from Dromedary are Secreted and Displayed by Mouse B Cells," (2003) Immunology 109(1):93-101.
Nishimoto et al., "Adoptive Therapy with Cord Blood T Regulatory Cells Enhances Anti-myeloma Efficacy of T Cell Based Immunotherapies," (2020) Blood 136(Suppl1); 26-27.
Norelli et al., "Monocyte-derived IL-1 and IL-6 are differentially required for cytokine-release syndrome and neurotoxicity due to Car T cells," (2018) Nature Medicine24(6): 739-748.
Novak et al., "Expression of BCMA, TACI, and BAFF-R in multiple myeloma: a mechanism for growth and survival," (2004) Blood 103(2):689-694.
Nuttall et al., "Isolation and Characterization of an IgNAR Variable Domain Specific for the Human Mitochondrial Translocase Receptor Tom70," (2003) Eur. J. Biochem. 270(17):3543-3554.
Nuttall et al., "Selection and Affinity Maturation of IgNAR Variable Domains Targeting *Plasmodium Falciparum* AMA1," (2004) Function and Bioinformatics 55:187-197.
Ofran et al. "Automated identification of complementarity determining regions (CDRs) reveals peculiar characteristics of CDRs and B-cell epitopes," (2008) Journal of Immunology 181(9):6230-6235.
Omniab: Naturally Optimized Human Antibodies (2016) retrieved from the Internet at: http://content.stockpr.com/omniab/db/252/746/file/OmniAb.pdf.
OMT Therapeutics Announces UniRatTM Alliance with Caltech, Business Wire (2015) retrieved from the Internet at: http://www.businesswire.com/news/home/20150514006523/en/OMT-Therapeutics-Announces-UniRat(TM)-Alliance-Caltech.
Padlan et al., "Identification of specificity-determining residues in antibodies," (1995) FASEB Journal 9(1):133-139.
Palumbo et al., "Daratumumab, Bortezomib, and Dexamethasone for Multiple Myeloma," (2016) New England Journal of Medicine 375(8):754-766.
Panowski et al., "Preclinical efficacy and safety comparison of CD3 bispecific and ADC modalities targeting BCMA for the treatment of multiple myeloma," (2019) Mol Cancer Ther 18(11):2008-2020.
Patel et al., "Engineering an APRIL-specific B Cell Maturation Antigen," (2004) Journal of Biological Chemistry 279(16):16727-16735.
Patentee's Response to EP Communication under Article 94(3), dated May 10, 2017 in EP Application No. 12805432.7.
Patentee's Response to EP Communication under Article 94(3), dated Apr. 13, 2016 in EP Application No. 12805432.7.
Pelekanou et al., "Expression of TNF-superfamily members BAFF and APRIL in Breast Cancer: Immunohistochemical Study in 52 Invasive Ductal Breast Carcinomas," (2008) BMC Cancer 8(76):1-9.
Pessano et al., "The T3/T cell receptor complex: antigenic distinction between the two 20-kd T3 (T3-o and T3-£) subunits," (1985) The EMBO Journal 4(2):337-344.
Pick et al., "Daratumumab resistance is frequent in advanced-stage multiple myeloma patients irrespective of CD38 expression and is related to dismal prognosis," (2018) European Journal of Haematology 100(5):494-501.
Plückthun et al., "New protein engineering approaches to multivalent and bispecific antibody fragments," (1997) Immunology 3(2):83-105.
Presta et al., "Generation of Humanized, High Affinity Anti-tissue Factor Antibody Use as a Novel Antithrombotic Therapeutic," (2001) Thromb Haemost 85(3):379-389.
Presta et al., "Humanization of an Antibody Directed Against IgE," (1993) Journal of Immunology 151(5):2623-2632.
Product Summary for Milteniy Biotec CD3 Antibodies Recombinant [online], Retrieved from the Internet: https://www.miltenyibiotec.com/US-en/products/cd3-antibodies-rea613.html#fitc:1-ml.
Product Summary for Cd3e Monoclonal Antibody (SPV-T3b) [online], Retrieved from the Internet: https://www.labome.com/product/Invitrogen/07-0303.html.
Proprietor's Remarks in Response to Office Action dated Dec. 16, 2014 in U.S. Pat. No. 9,340,621.
Proprietor's Remarks in Response to Office Action dated Jun. 19, 2014 in U.S. Pat. No. 9,150,664.
Pulte et al., "CD369 Expression on T Lymphoctyes Correlates with Severity of Disease in Patients with Chronic Lymphocytic Leukemia," (2011) Clinical Lymphoma, Myeloma & Leukemia 11(4):367-372.
Qin et al., "Paralleled comparison of vectors for the generation of CAR-T cells," (2016) Anti-Cancer Drugs 27(8):711-722.
Rangaswamy et al., "A Novel T-cell Bispecific Antibody Platform for Efficient T-cell Mediated Killing of Tumor Cells with Minimal Cytokine Oncology," (2018) Journal of Clinical Oncology No. 5_suppl: 209-209, DOI: 10.1200/JCO.2018.36.5_suppl.20.
Ravetch et al., "Fc Receptors," (1991) Annual Review of Immunology 9:457-492.
Reichert et al., "Development Trends for Monoclonal Antibody Cancer Therapeutics," (2007) Nat Rev Drug Discov 6(5):349-356.
Rennert et al., "A Soluble Form of B Cell Maturation Antigen, a Receptor for the Tumor Necrosis Factor Family Member APRIL, Inhibits Tumor Cell Growth," (2000) J. Exp. Med. 192(11):1677-1683.
Revets et al., "Nanobodies as novel agents for cancer therapy," (2005) Expert Opin Biol Ther 5(1):111-124.
Ridgway et al., "'Knobs-into-holes' Engineering of Antibody $C_H 3$ Domains for Heavy Chain Heterodimerization," (1996) Protein Engineering 9(7):617-621.
Rodriguez et al., "Initial Results of a Phase I Study of TNB-383B, a BCMA x CD3 Bispecific T-Cell Redirecting Antibody, in Relapsed/Refractory Multiple Myeloma," (2020) Blood 136 (Supp 1):43-44.
Roit, Immunology, translated from English, Moscow: Mir; 2000.
Rossi et al., "Redirected T-cell Killing of Solid Cancers Targeted with an Anti-CD3/Trop-2-Bispecific Antibody is Enhanced in Combination with Interferon-g," 2014 Molecular Cancer Therapeutics 13(10):2341-2351.
Rouet et al., "Fully Human VH Single Domains that Rival the Stability and Cleft Recognition of Camelid Antibodies," (2015) Journal of Biological Chemistry 290(19):11905-11917.

(56) References Cited

OTHER PUBLICATIONS

Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.
Ryan et al., "Antibody Targeting of B-Cell Maturation Antigen on Malignant Plasma Cells," (2007) Mol Cancer Ther 6(11):3009-3018.
Salmeron et al., "A conformational epitope expressed upon association of CD3-epsilon with either CD3-delta or CD3-gamma is the main target for recognition by anti-CD3 monoclonal antibodies." (1991) J. Immunol 147(9):3047-3052.
Sanchez et al., "Serum B-cell Maturation Antigen Elevated in Multiple Myeloma and Correlates with Disease Status and Survival," (2012) Br J Haematol 158(6): 727-738.
Sanz et al., "B cells as therapeutic targets in SLE" (2010) Nat Rev Rheumatol 6(6):326-337.
Seckinger et al., "Target Expression, Generation, Preclinical Activity, and Pharmacokinetics of the BCMA-T Cell Bispecific Antibody EM801 for Multiple Myeloma Treatment," (2017) Cancer Cell, Cell Press US 31(3):396-410.
Shallis et al., "The Multi-faced Potential of CD38 Antibody Targeting in Multiple Myeloma," (2017) Cancer Immunol Immunother 66:697-703.
Shields et al., "High Resolution Mapping of the Binding Site on Human IgG1 for FcγRI, FcγRII, FcγRIII, and FcRn and Design of IgG1 Variants with Improved Binding to the FcγR," (2001) J Biol Chem. 276(9):6591-6604.
Shoji-Hosaka et al., "Enhanced Fc-Dependent Cellular Cytotoxicity of Fc Fusion Proteins Derived from TNF Receptor II and LFA-3 by Fucose Removal from Asn-linked Oligosaccarides," (2006) Journal of Biochemistry 140(6):777-783.
Sitia et al., "Developmental regulation of IgM secretion: The role of the carboxy-terminal cysteine," (1990) Cell 60(5):781-790.
Tai et al., "APRIL and BCMA promote human multiple myeloma growth and immunosuppression in the bone marrow microenvironment," (2016) Blood 127(25):3225-3236, DOI: 10.1182/blood-2016-01-691162.
Tai et al., "Novel anti-B-cell maturation antigen antibody-drug conjugate (GSK2857916) selectively induces killing of multiple myeloma," (2014) Blood 123(20):3128-3138.
Tao et al., "Structural features of human immunoglobulin G that determine isotype-specific differences in complement activation," (1993) Journal of Experimental Medicine 178(2):661-667.
Tarte et al., "BAFF is a survival factor for multiple myeloma cells," Myeloma Biology II (2002) p. 811a (Abstract #3203).
Thakur et al., "Cancer therapy with bispecific antibodies: Clinical experience," (2010) Current Opinion in Molecular Therapeutics 12(3):340-349.
Topp et al., "Anti-B-Cell Maturation Antigen BiTE Molecule AMG 420 Induces Responses in Multiple Myeloma." (2020) J Clin Oncol 38(8): 775-783.
Trinklein et al., "Efficient Tumor Killing and Minimal Cytokine Release with Novel T-cell Agonist Bispecific Antibodies," (2019) MABS 11(4):639-652.
Tueresson et al., "Patterns of Improved Survival in Patients with Multiple Myeloma in the Twenty-First Century: A Population-Based Study," (2010) Journal of Clinical Oncology 28(5):830-834.
Van der Linden et al., "Comparison of Physical Chemical Properties of Llama VHH Antibody Fragments and Mouse Monoclonal Antibodies," (1999) Biochim Biophys Acta 1431(1):37-46.
Van Schooten et al., "A Novel CD3/BCMA Bispecific Antibody Selectively Kills Plasma Cells in Bone Marrow of Healthy Individuals with Improved Safety," (2019) Lupus Science and Medicine 6, DOI: 1 0.1136/lupus-2019-lsm.293.
Verkleij et al., "T-Cell Redirecting Bispecific Antibodies Targeting BCMA for the Treatment of Multiple Myeloma," (2020) Oncotarget 11(45):4076-4081.

Vidal-Laliena et al., "Characterization of antibodies submitted to the B cell section of the 8th human leukocyte differentiation antigens workshop by flow cytometry and immunohistochemistry," (2005) Cellular Immunology 236(1-2):6-16.
Vu, "A New Class of T-cell Bispecific Antibodies for the Treatment of Multiple Myeloma, Binding to B Cell Maturation Antigen and CD3 and Showing Potent, Specific Antitumor Activity in Myeloma Cells and Long Duration of Action in Cynomolgus Monkeys," (2015) Blood 126(23):2998.
Walker et al., "CD22: An Inhibitory Enigma," (2007) Immunology 123:314-325.
Wallweber et al., "The Crystal Structure of A Proliferation-inducing Ligand, APRIL," (2004) Journal of Molecular Biology 343(2):283-290.
Waxman et al., "Racial disparities in incidence and outcome in multiple myeloma: a population-based study," (2010) Blood 116(25):5501-5506.
Wayback machine snapshot of BCMA UniprotKB/Swiss-Prot entry, Aug. 3, 2011 https://web.archive.org/web/20110803071256/ https://www.uniprot.orq/uniprot/Q02223 [Inactive Link].
Werther et al., "Humanization of an Anti-lymphocyte Function-associated Antigen (LFA)-1 Monoclonal Antibody and Reengineering of the Humanized Antibody for Binding to Rhesus LFA-1," (1996) Journal of Immunology 157(11):4986-4995.
Winter et al., "Humanized Antibodies," (1993) Immunology Today 14(6):243 246.
Wu et al., "CD38-expressing Macrophages Drive Age—related NAD+ Decline," (2020) Nature Metabolism 2(11):1186-1187.
Wu et al., "Simultaneous Targeting of Multiple Disease Mediators by a Dual-variable-domain Immunoglobulin," (2007) Nature Biotechnology 25(11):1290-1297.
Yoon et al., "Both High and Low Avidity Antibodies to the T Cell Receptor can have Agonist Activity," (1994) Immunity 1(7):563-569.
Zhao et al., "A germline knowledge based computational approach for determining antibody complementarity determining regions," (2010) Molecular Immunology 47(4):694-700.
Zou et al., "Heavy chain—only antibodies are spontaneously produced in light chain—deficient mice," (2007) J Exp Med 204(13): 3271-3283.
Buelow et al., "Effect of modulation of CD3 binding in a PSMAxCD3 T-cell engaging bispecific antibody on maintenance of efficient tumor cell kill cytokine release," (2020) J. Clin. Oncol. 38(15):Supple. 17583, DOI: 10.1200/JCO.2020.38.15_suppl.e17583.
Buelow et al., "TNB585.001: A multicenter, phase 1, open-label, dose-escalation and expansion study of TNB-585, a bispecific T-cell engager targeting PSMA in subjects with metastatic castrate resistant prostate cancer," (2021) J. Clin. Oncol. 39(15):Suppl.TPS5092, DOI: 10.1200/JCO.2021.39.15_suppl.TPS5092.
Clarke et al., "A novel CD3xPSMA bispecific antibody for efficient T cell mediated killing of prostate tumor cells with minimal cytokine release," (2019) Journal of Clinical Oncology 37, No. 7_suppl, DOI: 10.1200/JCO.2019.37.7_suppl.324.
ClinicalTrials.gov, "A Study of AMG 340 in Subjects with Metastatic Castrate-Resistant Prostate Carcinoma," (2021) ID: NCT04740034; 8 pages.
Dang et al., "Attenuating CD3 affinity in a PSMAxCD3 bispecific antibody enables killing of prostate tumor cells with reduced cytokine release," (2021) J Immunother Cancer 9:e002488; 14 pages.
Dong et al., "Structural Basis of Assembly of the Human T Cell Receptor—CD3 Complex," (2019) Nature, vol. 573: 546-552.
Hassanzadeh-Ghassabeh et al., "Nanobodies and their potential applications," (2013) 8(6):1013-1023.
Kishimoto et al., "Physical Dissociation of the TCR-CD3 Complex Accompanies Receptor Ligation," (1995). Journal of Experimental Medicine, vol. 182: 1997-B1762006.
Vincke et al., "General strategy to humanize a camelid single-domain antibody and identification of a universal humanized nanobody scaffold," (2009) J Biol Chem 284(5):32373-3284.

* cited by examiner

Anti-CD3 x monovalent, monospecific anti-CD22

Anti-CD3 x bivalent, monospecific anti-CD22

Anti-CD3 x bivalent, biparatopic anti-CD22

| Clone ID # | KD (M) | Kdis (1/s) | Daudi binding | CHO_cyCD22 | CHO_cyOFFtgt |
|---|---|---|---|---|---|
| 335161 | 2.66E-09 | 2.40E-04 | 811.0 | 208.0 | 5.2 |
| 335254 | 2.83E-09 | 2.45E-04 | 733.0 | 194.0 | 5.1 |
| 335260 | 3.17E-09 | 2.75E-04 | 725.0 | 185.0 | 5.1 |
| 335207 | 3.24E-09 | 2.94E-04 | 776.0 | 209.0 | 5.3 |
| 335151 | 3.77E-09 | 3.21E-04 | 861.0 | 222.0 | 5.3 |
| 335170 | 6.50E-09 | 3.40E-04 | 791.0 | 181.0 | 5.3 |
| 335176 | 4.62E-09 | 3.79E-04 | 848.0 | 212.0 | 5.3 |
| 335181 | 9.44E-09 | 4.43E-04 | 809.0 | 234.0 | 5.4 |
| 335244 | 5.07E-09 | 4.45E-04 | 752.0 | 198.0 | 5.2 |
| 335154 | 5.41E-09 | 4.46E-04 | 837.0 | 232.0 | 5.3 |
| 335201 | 5.19E-09 | 4.67E-04 | 761.0 | 199.0 | 5.5 |
| 335261 | 5.27E-09 | 5.10E-04 | 748.0 | 181.0 | 5.1 |
| 324510 | 6.42E-09 | 5.54E-04 | 690.0 | 172.0 | 5.2 |
| 335293 | 7.41E-09 | 5.57E-04 | 742.0 | 179.0 | 5.3 |
| 335203 | 6.80E-09 | 6.41E-04 | 729.0 | 194.0 | 5.3 |
| 335185 | 8.43E-09 | 6.47E-04 | 754.0 | 220.0 | 5.5 |
| 324317 | 8.48E-09 | 6.58E-04 | 709.0 | 173.0 | 5.2 |
| 335206 | 7.53E-09 | 6.90E-04 | 735.0 | 189.0 | 5.3 |
| 335245 | 7.44E-09 | 7.02E-04 | 742.0 | 192.0 | 5.4 |
| 335218 | 8.91E-09 | 7.05E-04 | 711.0 | 204.0 | 5.1 |
| 335160 | 8.51E-09 | 7.24E-04 | 750.0 | 218.0 | 5.2 |
| 335158 | 4.23E-08 | 8.01E-41 | 883.0 | 193.0 | 5.4 |
| 324508 | 1.25E-08 | 8.28E-04 | 839.0 | 162.0 | 5.2 |
| 335307 | 1.03E-08 | 1.02E-03 | 737.0 | 176.0 | 5.0 |
| 335301 | 1.26E-08 | 1.29E-03 | 716.0 | 166.0 | 5.0 |
| 335323 | 1.41E-08 | 1.30E-03 | 720.0 | 169.0 | 5.3 |
| 335271 | 2.16E-08 | 1.31E-03 | 711.0 | 147.0 | 5.2 |
| 335234 | 1.24E-08 | 1.37E-03 | 734.0 | 161.0 | 5.2 |
| 335182 | 2.24E-08 | 1.58E-03 | 750.0 | 192.0 | 5.3 |

FIG. 16

| Clone ID # | KD (M) | Kdis (1/s) | Daudi binding | CHO_cyCD22 | CHO_cyOFFtgt |
|---|---|---|---|---|---|
| 335186 | 1.76E-08 | 1.72E-03 | 402.0 | 33.5 | 5.5 |
| 335233 | 1.90E-08 | 2.01E-03 | 697.0 | 166.0 | 5.3 |
| 335224 | 2.34E-08 | 2.07E-03 | 689.0 | 173.0 | 5.4 |
| 335210 | 6.25E-08 | 2.28E-03 | 735.0 | 159.0 | 5.2 |
| 335311 | 2.66E-09 | 2.77E-03 | 151.0 | 11.7 | 5.1 |
| 335159 | 1.61E-08 | 3.58E-03 | 532.0 | 61.7 | 5.4 |
| 335188 | 5.30E-08 | 4.12E-03 | 663.0 | 113.0 | 5.3 |
| 335274 | 2.36E-08 | 4.30E-03 | 414.0 | 26.0 | 5.1 |
| 335226 | 2.55E-08 | 4.37E-03 | 221.0 | 12.0 | 5.2 |
| 335333 | 2.24E-08 | 4.37E-03 | 372.0 | 21.2 | 5.0 |
| 335283 | 3.69E-08 | 4.57E-03 | 513.0 | 42.4 | 5.2 |
| 335297 | 2.88E-08 | 4.80E-03 | 107.0 | 12.3 | 5.2 |
| 335273 | 4.22E-08 | 4.87E-03 | 385.0 | 23.1 | 5.2 |
| 335187 | 1.28E-07 | 5.12E-03 | 531.0 | 60.7 | 6.0 |
| 335295 | 3.16E-08 | 5.21E-03 | 491.0 | 43.8 | 5.1 |
| 335220 | 4.82E-08 | 5.31E-03 | 322.0 | 18.4 | 5.4 |
| 335173 | 3.05E-08 | 5.43E-03 | 393.0 | 26.7 | 5.5 |
| 335219 | 9.06E-08 | 5.50E-03 | 590.0 | 76.2 | 5.2 |
| 335236 | 2.73E-08 | 5.62E-03 | 338.0 | 18.4 | 5.3 |
| 335266 | 3.85E-08 | 5.79E-03 | 411.0 | 29.2 | 5.1 |
| 335208 | 5.84E-08 | 5.93E-03 | 452.0 | 34.0 | 5.4 |
| 335195 | 1.50E-07 | 5.99E-03 | 420.0 | 33.0 | 5.4 |
| 335285 | 1.14E-07 | 6.07E-03 | 620.0 | 94.7 | 5.1 |
| 335150 | 1.41E-08 | 6.08E-03 | 86.3 | 8.8 | 5.2 |
| 335316 | 2.35E-08 | 6.62E-03 | 103.0 | 9.6 | 5.1 |
| 335189 | 3.60E-08 | 6.92E-03 | 410.0 | 28.6 | 5.3 |
| 335179 | 1.48E-07 | 8.91E-03 | 88.8 | 10.5 | 5.5 |
| 335230 | 7.52E-08 | 8.92E-03 | 47.1 | 7.8 | 5.3 |
| 335166 | 3.30E-08 | 9.15E-03 | 422.0 | 35.5 | 5.2 |
| 335242 | 7.97E-08 | 9.30E-03 | 136.0 | 11.3 | 5.2 |
| 335162 | 9.96E-08 | 9.41E-03 | 23.3 | 9.1 | 5.2 |

FIG. 16 (Cont. 1)

| Clone ID # | KD (M) | Kdis (1/s) | Daudi binding | CHO_cyCD22 | CHO_cyOFFtgt |
|---|---|---|---|---|---|
| 335171 | 8.45E-08 | 1.24E-02 | 471.0 | 39.0 | 5.4 |
| 335232 | 2.46E-08 | 1.83E-02 | 288.0 | 42.5 | 5.3 |
| 335263 | 2.58E-06 | 3.85E-02 | 30.0 | 8.2 | 5.2 |

FIG. 16 (Cont. 2)

```
                        SEQUENCE LISTING

<160> NUMBER OF SEQ ID NOS: 107

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Asp Ser Ile Ser Ser Gly Asp Tyr Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Asp Ser Ile Ser Ser Gly Gly Tyr Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Ser Ile Ser Ser Gly Asp Tyr Tyr
1               5                   10

<210> SEQ ID NO 4
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Ile Ser Ser Ser Ser Tyr Tyr
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Ser Phe Ser Gly Tyr Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asp Ser Ile Ser Ser Ser Ser Tyr Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Ser Ile Thr Ser Ser Ser Tyr Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Ser Ile Ser Ser Ser Ser His Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Gly Gly Ser Ile Ile Ser Ser Ser Tyr Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Ser Ile Asn Asp Asn Ser His Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Tyr Tyr Ser Gly Val Thr
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Tyr Tyr Ser Gly Ala Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Tyr Tyr Ser Gly Ser Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Tyr Tyr Thr Gly Ser Thr
1               5

<210> SEQ ID NO 15
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 15

Val Tyr Tyr Thr Gly Ala Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile His Tyr Ser Gly Ser Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Tyr Tyr Ser Gly Ser Ala
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Arg Glu Asp Ser Ser Asn Trp Arg Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Arg Asp Asp Ser Ser Asn Trp Arg Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Arg Glu Asp Ser Ser Ser Trp Arg Ser
1               5                   10
```

```
<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Arg Glu Asp Ser Ser Ser Trp Arg Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Arg Asp Asp Ser Ser Asn Trp Arg Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Arg Asp Asp Ser Ser Asn Trp Arg Ser
1               5                   10

<210> SEQ ID NO 24
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
                20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Val Thr Tyr Tyr Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 25
<211> LENGTH: 118
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Glu Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Leu Gln Leu Gln Glu Ser Gly Pro Gly Leu Val Lys Pro Ser Glu
```

```
                1               5                   10                  15
Thr Leu Ser Leu Thr Cys Thr Val Ser Gly Asp Ser Ile Ser Ser Gly
                20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
                20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
                20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
```

```
                 50                  55                  60

Leu Lys Asn Arg Val Thr Ile Ser Val Asp Thr Ser Arg Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Asp Asp Ser Ser Asn Trp Arg Ser Arg Gly Gln Gly Thr
                100                 105                 110

Leu Val Thr Val Ser Ser
            115

<210> SEQ ID NO 30
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Ser Ser Gly
                 20                  25                  30

Asp Tyr Tyr Trp Gly Trp Ile Arg Gln Pro Pro Gly Lys Gly Leu Glu
                 35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Asp Asp Ser Ser Asn Trp Arg Ser Arg Gly Gln Gly Thr
                100                 105                 110

Leu Val Thr Val Ser Ser
            115

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Ser Ser Gly
                 20                  25                  30

Gly Tyr Tyr Trp Gly Trp Ile Arg Gln Pro Pro Gly Lys Gly Leu Glu
                 35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Asp Asp Ser Ser Asn Trp Arg Ser Arg Gly Gln Gly Thr
```

```
                    100                 105                 110

Leu Val Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 34
<211> LENGTH: 118
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 34

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Glu Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Leu Gln Leu Gln Glu Ser Gly Pro Gly Leu Val Lys Pro Ser Glu
1               5                   10                  15

```
Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
 65                  70                  75                  80

Ser Leu Lys Leu Ser Ser Val Thr Ala Ala Asp Thr Ala Val Tyr Tyr
            85                  90                  95

Cys Thr Arg Glu Asp Ser Ser Trp Arg Ser Arg Gly Gln Gly Thr
                100                 105                 110

Leu Val Thr Val Ser Ser
            115
```

```
<210> SEQ ID NO 37
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Val Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
            85                  90                  95

Cys Thr Arg Glu Asp Ser Ser Asn Trp Arg Ser Arg Gly Gln Gly Thr
                100                 105                 110

Leu Val Thr Val Ser Ser
            115
```

```
<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60
```

```
Leu Lys Asn Arg Val Thr Ile Ser Val Asp Thr Ser Arg Asn Gln Phe
 65                  70                  75                  80

Ser Leu Asn Leu Ser Ser Val Thr Ala Ala Asp Thr Ala Val Tyr Tyr
                 85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Ser Ser Gly
                 20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Ser Ser Gly
                 20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Glu Asp Ser Ser Ser Trp Arg Ser Arg Gly Gln Gly Thr
            100                 105                 110
```

```
Leu Val Thr Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 43
<211> LENGTH: 118
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Glu Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
                100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Asn Ile Tyr Tyr Ser Gly Ala Thr Tyr Tyr Asn Pro Ser
     50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
                100                 105                 110

Leu Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Gly Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
     50                  55                  60
```

-continued

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
                20                  25                  30

Asp Tyr Tyr Trp Gly Trp Ile Arg His Pro Pro Gly Lys Gly Leu Glu
            35                  40                  45

Trp Ile Gly His Ile Tyr Tyr Ser Gly Ala Thr Tyr Tyr Asn Pro Ser
        50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
                20                  25                  30

Asp Tyr Tyr Trp Gly Trp Ile Arg Gln Pro Pro Gly Lys Gly Leu Glu
            35                  40                  45

Trp Ile Gly Asn Ile Tyr Tyr Ser Gly Ala Thr Tyr Tyr Asn Pro Ser
        50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Asn Ile Tyr Tyr Ser Gly Ala Thr Tyr Tyr Asn Pro Ser
50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Thr Arg Asp Asp Ser Ser Asn Trp Arg Ser Arg Gly Gln Gly Thr
        100                 105                 110

Leu Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Thr Arg Asp Asp Ser Ser Asn Trp Arg Ser Arg Gly Gln Gly Thr
        100                 105                 110

Leu Val Thr Val Ser Ser
        115

<210> SEQ ID NO 52
<211> LENGTH: 118
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly

```
                 20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
 65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
            115

<210> SEQ ID NO 55
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Leu Gln Leu Gln Glu Ser Gly Pro Gly Leu Val Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Gly Trp Ile Arg Gln Pro Pro Gly Lys Gly Leu Glu Trp Ile
            35                  40                  45

Gly His Ile Tyr Tyr Ser Gly Ala Thr Tyr Tyr Asn Pro Ser Leu Lys
 50                  55                  60

Asn Arg Val Thr Ile Ser Val Asp Thr Ser Arg Asn Gln Phe Ser Leu
 65                  70                  75                  80

Asn Leu Ser Ser Val Thr Ala Ala Asp Thr Ala Val Tyr Tyr Cys Thr
                85                  90                  95

Arg Glu Asp Ser Ser Trp Arg Ser Arg Gly Gln Gly Thr Leu Val
            100                 105                 110

Thr Val Ser Ser
            115

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly His Ile Tyr Tyr Ser Gly Val Thr Tyr Tyr Asn Pro Ser
 50                  55                  60

Leu Lys Asn Arg Val Thr Ile Ser Val Asp Thr Ser Lys Asn Gln Phe
```

```
65                  70                  75                  80

Ser Leu Lys Leu Ser Ser Val Thr Ala Ala Asp Thr Ala Ala Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly His Ile Tyr Tyr Ser Gly Val Thr Tyr Tyr Asn Pro Ser
        50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
```

115

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Ser Ser Ser Trp Arg Ser Arg Gly Gln Gly Thr
            100                 105                 110

Leu Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 61

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 62

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 63

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

```
Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
                100                 105                 110

Leu Val Thr Val Ser Ser
            115

<210> SEQ ID NO 64
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
                100                 105                 110

Leu Val Thr Val Ser Ser
            115

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
 65                  70                  75                  80
```

```
Ser Leu Asn Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115
```

```
<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Val Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 70

Gln Leu Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 71
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 72
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

```
Ser Tyr Tyr Trp Gly Trp Ile Arg Gln Pro Pro Lys Gly Leu Glu
        35                  40                  45

Trp Ile Gly Ser Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
 65                  70                  75                  80

Ser Leu Asn Leu Ser Ser Val Thr Ala Ala Asp Thr Ala Met Tyr Tyr
                 85                  90                  95

Cys Thr Arg Glu Asp Ser Ser Asn Trp Arg Ser Arg Gly Gln Gly Thr
            100                 105                 110

Leu Val Thr Val Ser Ser
        115
```

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Val Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Glu Asp Ser Ser Ser Trp Arg Ser Arg Gly Gln Gly Thr
            100                 105                 110

Leu Val Thr Val Ser Ser
        115
```

<210> SEQ ID NO 74
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Ser Pro Glu Lys Gly Leu Glu
        35                  40                  45

Trp Ile Gly His Ile Tyr Tyr Ser Gly Val Thr Tyr Tyr Asn Pro Ser
 50                  55                  60

Leu Lys Asn Arg Val Thr Ile Ser Val Asp Thr Ser Lys Asn Gln Phe
 65                  70                  75                  80
```

```
Ser Leu Lys Leu Ser Ser Val Thr Ala Ala Asp Thr Ala Val Tyr Tyr
             85                  90                  95

Cys Lys Arg Asp Asp Ser Ser Asn Trp Arg Ser Arg Gly Gln Gly Thr
            100                 105                 110

Leu Val Thr Val Ser Ser
        115

<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
             85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 76
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Val Tyr Tyr Thr Gly Ala Thr Tyr Tyr Asn Pro Ser
50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
             85                  90                  95

Cys Thr Arg Asp Asp Ser Ser Asn Trp Arg Ser Arg Gly Gln Gly Thr
            100                 105                 110

Leu Val Thr Val Ser Ser
        115
```

<210> SEQ ID NO 77
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Phe Arg His Pro Pro Gly Lys Gly Leu Asp
        35                  40                  45

Trp Ile Gly Ser Ile His Tyr Ser Gly Ser Thr Tyr Tyr Asn Pro Ser
    50                  55                  60

Leu Lys Ser Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 78
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Leu Gln Leu Gln Glu Ser Asp Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser His Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 79
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 79

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115
```

<210> SEQ ID NO 80
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115
```

<210> SEQ ID NO 81
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Ser Ser
            20                  25                  30

Ser Tyr Tyr Trp Gly Trp Ile Arg Gln Pro Pro Gly Lys Gly Leu Glu
```

```
                35                  40                  45
Trp Ile Gly Ser Ile Tyr Tyr Ser Gly Ser Ala Tyr Tyr His Pro Ser
         50                  55                  60
Leu Lys Ser Arg Val Thr Ile Ser Ile Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg Asp Asp Ser Ser Asn Trp Arg Ser Arg Gly Gln Gly Thr
            100                 105                 110
Leu Val Thr Val Ser Ser
        115

<210> SEQ ID NO 82
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Leu Gln Leu Gln Glu Ser Gly Pro Gly Leu Val Lys Pro Ser Glu
 1               5                  10                  15
Thr Leu Ser Leu Thr Cys Thr Val Ser Gly Gly Ser Ile Ser Ser Ser
             20                  25                  30
Ser Tyr Tyr Trp Gly Trp Ile Arg Gln Pro Pro Gly Lys Gly Leu Glu
         35                  40                  45
Trp Ile Gly Ser Ile Tyr Tyr Ser Gly Ala Thr Tyr Tyr Asn Pro Ser
         50                  55                  60
Leu Lys Asn Arg Val Thr Ile Ser Val Asp Thr Ser Arg Asn Gln Phe
 65                  70                  75                  80
Ser Leu Asn Leu Ser Ser Val Thr Ala Ala Asp Thr Ala Val Tyr Tyr
                 85                  90                  95
Cys Thr Arg Asp Asp Ser Ser Asn Trp Arg Ser Arg Gly Gln Gly Thr
            100                 105                 110
Leu Val Thr Val Ser Ser
        115

<210> SEQ ID NO 83
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Leu Gln Leu Gln Glu Ser Gly Pro Gly Leu Val Lys Pro Ser Glu
 1               5                  10                  15
Thr Leu Ser Leu Thr Cys Thr Val Ser Gly Asp Ser Ile Ser Ser Gly
             20                  25                  30
Asp Tyr Tyr Trp Gly Trp Ile Arg Gln Pro Pro Gly Lys Gly Leu Glu
         35                  40                  45
Trp Ile Gly His Ile Tyr Tyr Ser Gly Ala Thr Tyr Tyr Asn Pro Ser
         50                  55                  60
Leu Lys Asn Arg Val Thr Ile Ser Val Asp Thr Ser Arg Asn Gln Ser
 65                  70                  75                  80
Ser Leu Asn Leu Ser Ser Val Thr Ala Ala Asp Thr Ala Val Tyr Tyr
```

```
                         85                  90                  95

Cys Thr Arg Glu Asp Ser Ser Asn Trp Arg Ser Arg Gly Gln Gly Thr
                100                 105                 110

Leu Val Thr Val Ser Ser
        115

<210> SEQ ID NO 84
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Asp Asn
            20                  25                  30

Ser His Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
                100                 105                 110

Leu Val Thr Val Ser Ser
        115

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Phe Thr Phe His Asn Tyr Ala
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Ser Trp Asn Ser Gly Ser Ile
1               5

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 87

Ala Lys Asp Ser Arg Gly Tyr Gly Asp Tyr Ser Leu Gly Gly Ala Tyr
1               5                   10                  15

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Ser Val Ser Ser Asn
1               5

<210> SEQ ID NO 89
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Ala Ser
1

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gln Tyr Asn Asn Trp Pro Trp Thr
1               5

<210> SEQ ID NO 91
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Leu Gly Gly Ala Tyr
            100                 105                 110
```

```
Trp Gly Gln Gly Thr Leu Val Thr Val Ser Ser Asp Tyr Arg Leu Gly
        115                 120                 125
Gly Ala Tyr Trp Gly Gln Gly Thr Leu Val Thr Val Ser Ser
    130                 135                 140

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro Trp
                85                  90                  95
Thr Phe Gly Gln Gly Thr Lys Val Glu Ile Lys
            100                 105

<210> SEQ ID NO 93
<211> LENGTH: 330
<212> TYPE: PRT
<213> ORGANISM: Homo sapiens

<400> SEQUENCE: 93

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 94
<211> LENGTH: 327
<212> TYPE: PRT
<213> ORGANISM: Homo sapiens

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
                    210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 95
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 96
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 97
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 98
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Glu Val Gln Leu Val Glu Ser Gly Gly Gly Leu Val Gln Pro Gly Arg
1               5                   10                  15
```

-continued

Ser Leu Arg Leu Ser Cys Ala Ala Ser Gly Phe Thr Phe His Asn Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ser Arg Gly Tyr Gly Asp Tyr Ser Leu Gly Gly Ala Tyr
             100                 105                 110

Trp Gly Gln Gly Thr Leu Val Thr Val Ser Ser Ala Ser Thr Lys Gly
         115                 120                 125

Pro Ser Val Phe Pro Leu Ala Pro Ser Ser Lys Ser Thr Ser Gly Gly
     130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Ile Cys Asn Val
         195                 200                 205

Asn His Lys Pro Ser Asn Thr Lys Val Asp Lys Val Glu Pro Lys
     210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                 245                 250                 255

Leu Met Ile Ser Arg Thr Pro Glu Val Thr Cys Val Val Val Asp Val
             260                 265                 270

Ser His Glu Asp Pro Glu Val Lys Phe Asn Trp Tyr Val Asp Gly Val
         275                 280                 285

Glu Val His Asn Ala Lys Thr Lys Pro Arg Glu Glu Gln Tyr Asn Ser
     290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Glu Glu Met Thr Lys Asn Gln
         355                 360                 365

Val Ser Leu Thr Cys Leu Val Lys Gly Phe Tyr Pro Ser Asp Ile Ala
     370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
             420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 99
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 100
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly

```
            225                 230                 235                 240
Pro Ser Val Phe Leu Phe Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 101
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser Ala Ser Thr Lys Gly
        115                 120                 125
```

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
450

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Gly Ser
1               5

<210> SEQ ID NO 103

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Gly Gly Ser Gly Gly Gly Gly Ser
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp or Gly
<220> FEATURE:
<221> NAME/KEY: MOD_RES
<222> LOCATION: (5)..(5)
<223> OTHER INFORMATION: Ser, Thr, Ile, or Asn
<220> FEATURE:
<221> NAME/KEY: MOD_RES
<222> LOCATION: (6)..(6)
<223> OTHER INFORMATION: Ser or Asp
<220> FEATURE:
<221> NAME/KEY: MOD_RES
<222> LOCATION: (7)..(7)
<223> OTHER INFORMATION: Gly, Ser, or Asn
<220> FEATURE:
<221> NAME/KEY: MOD_RES
<222> LOCATION: (8)..(8)
<223> OTHER INFORMATION: Asp, Gly, or Ser
<220> FEATURE:
<221> NAME/KEY: MOD_RES
<222> LOCATION: (9)..(9)
<223> OTHER INFORMATION: Tyr or His

<400> SEQUENCE: 104

Gly Xaa Ser Ile Xaa Xaa Xaa Xaa Xaa Tyr
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (2)..(2)
<223> OTHER INFORMATION: Tyr or His
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Ala, Val, or Ser
<220> FEATURE:
<221> NAME/KEY: MOD_RES
<222> LOCATION: (7)..(7)
<223> OTHER INFORMATION: Thr or Ala
```

```
<400> SEQUENCE: 105

Xaa Xaa Tyr Xaa Gly Xaa Xaa
1               5

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr, Ala, or Lys
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (7)..(7)
<223> OTHER INFORMATION: Asn or Ser

<400> SEQUENCE: 106

Xaa Arg Xaa Asp Ser Ser Xaa Trp Arg Ser
1               5                   10

<210> SEQ ID NO 107
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units
<220> FEATURE:
<223> OTHER INFORMATION: See specification as filed for detailed
      description of substitutions and preferred embodiments

<400> SEQUENCE: 107

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

MULTISPECIFIC HEAVY CHAIN ANTIBODIES BINDING TO CD22 AND CD3

CROSS-REFERENCE TO RELATED APPLICATIONS

This application claims priority benefit of the filing date of U.S. Provisional Patent Application Ser. No. 62/861,708, filed on Jun. 14, 2019, the disclosure of which application is herein incorporated by reference in its entirety.

SEQUENCE LISTING

The instant application contains a Sequence Listing which has been submitted electronically in ASCII format and is hereby incorporated by reference in its entirety. Said ASCII copy, created on Jul. 10, 2020, is named TNO-0017-US_SL.txt and is 112,369 bytes in size.

FIELD OF THE INVENTION

The present invention concerns multispecific, human heavy chain antibodies (e.g., UniAbs™) binding to CD22 and CD3. The invention further concerns methods of making such antibodies, compositions, including pharmaceutical compositions, comprising such antibodies, and their use to treat disorders that are characterized by the expression of CD22.

BACKGROUND OF THE INVENTION

CD22

CD22, also known as SIGLEC-2 (UniProt P20273), is a cell-surface receptor that is expressed on mature B-cells. CD22 contains multiple Ig domains and is a member of the immunoglobulin superfamily. The extracellular domain of CD22 interacts with sialic acid moieties, including those present on the CD45 cell surface protein. CD22 is thought to function as an inhibitory receptor for B-cell receptor signaling. Along with CD20 and CD19, the restricted B-cell expression of CD22 makes it an attractive target for the therapeutic treatment of B-cell malignancies. Monoclonal antibodies specific to CD22 have been described in the literature (e.g., Jabbour, Elias, et al. "Monoclonal antibodies in acute lymphoblastic leukemia." *Blood* 125.26 (2015): 4010-4016) and have been used therapeutically as standard monoclonals (e.g., epratuzumab) as well as antibody-drug conjugates (inotuzumab ozogamicin). In addition, anti-CD22 chimeric antigen receptor T-cells have been used in the clinic to treat leukemia (Fry, Terry J., et al. "CD22-targeted CAR T cells induce remission in B-ALL that is naive or resistant to CD19-targeted CAR immunotherapy." *Nature medicine* (2017)).

Heavy Chain Antibodies

In a conventional IgG antibody, the association of the heavy chain and light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs™). The UniAbs™ of Camelidae (*Camelus dromedarius*, *Camelus bactrianus*, *Lama glama*, *Lama guanaco*, *Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These UniAbs™ lack the first domain of the constant region (CH1) which is present in the genome, but is spliced out during mRNA processing. The absence of the CH1 domain explains the absence of the light chain in the UniAbs™, since this domain is the anchoring place for the constant domain of the light chain. Such UniAbs™ naturally evolved to confer antigen-binding specificity and high affinity by three CDRs from conventional antibodies or fragments thereof (Muyldermans, 2001; *J Biotechnol* 74:277-302; Revets et al., 2005; *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The ability of heavy chain-only antibodies devoid of light chain to bind antigen was established in the 1960s (Jaton et al. (1968) *Biochemistry*, 7, 4185-4195). Heavy chain immunoglobulin physically separated from light chain retained 80% of antigen-binding activity relative to the tetrameric antibody. Sitia et al. (1990) *Cell*, 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Brüggemann et al., *Crit. Rev. Immunol.;* 2006, 26(5):377-90; and Zou et al., 2007, *J Exp Med;* 204(13): 3271-3283. The production of knockout rats via embryo microinjections of zinc-finger nucleases is described in Geurts et al., 2009, *Science,* 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domain are described, for example, in Iri-Sofia et al., 2011, *Experimental Cell Research* 317:2630-2641 and Jamnani et al., 2014, *Biochim Biophys Acta,* 1840:378-386.

SUMMARY OF THE INVENTION

Aspects of the invention relate to heavy chain antibodies, including but not limited to UniAbs™, with binding affinity to CD22. Further aspects of the invention relate to methods of making such antibodies, compositions comprising such antibodies, and their use in the treatment of disorders that are characterized by the expression of CD22.

Aspects of the invention include multi-specific binding compounds that bind to CD3, comprising: a heavy chain variable region comprising: (a) a CDR1 sequence having two or fewer substitutions in SEQ ID NO: 85; and/or (b) a CDR2 sequence having two or fewer substitutions in SEQ ID NO: 86; and/or (c) a CDR3 sequence having two or fewer substitutions in SEQ ID NO: 87; and a light chain variable region. In some embodiments, the heavy chain CDR1, CDR2 and CDR3 sequences are present in a human VH framework. In some embodiments, the heavy chain variable region comprises heavy chain CDR1, CDR2 and CDR3 sequences in a human VH framework, wherein each CDR sequence comprises a sequence with at least 85% identity to any one of SEQ ID NOs:85-87; and the binding compound also comprises a light chain variable region.

In some embodiments, the multi-specific binding compound comprises: a heavy chain variable region comprising: (a) a CDR1 sequence having two or fewer substitutions in SEQ ID NO: 85; and (b) a CDR2 sequence having two or fewer substitutions in SEQ ID NO: 86; and (c) a CDR3 sequence having two or fewer substitutions in SEQ ID NO: 87; and the binding compound also comprises a light chain variable region.

In some embodiments, the multi-specific binding compound comprises: a heavy chain variable region comprising a CDR1 sequence of SEQ ID NO: 85, a CDR2 sequence of SEQ ID NO: 86, and a CDR3 sequence of SEQ ID NO: 87; and the binding compound also comprises a light chain variable region.

In some embodiments, the light chain variable region comprises a CDR1, CDR2 and CDR3 sequence in a human VL framework, wherein each CDR sequence comprises a sequence with 3 or fewer amino acid substitutions relative to a CDR sequence or set of CDR sequences in SEQ ID NO: 92; or wherein the CDR sequences comprise a sequence with at least 85% identity to a CDR sequence or set of CDR sequences in SEQ ID NO: 92. In some embodiments, the light chain variable region comprises a CDR1 sequence of SEQ ID NO: 88, a CDR2 sequence of SEQ ID NO: 89, and a CDR3 sequence of SEQ ID NO: 90. In some embodiments, the heavy chain variable region comprises an amino acid sequence having at least 95% identity to SEQ ID NO: 91. In some embodiments, the heavy chain variable region comprises an amino acid sequence set forth in SEQ ID NO: 91. In some embodiments, the light chain variable region comprises an amino acid sequence having at least 95% identity to SEQ ID NO: 92. In some embodiments, the light chain variable region comprises an amino acid sequence of SEQ ID NO: 92.

Aspects of the invention include multi-specific binding compounds comprising a first binding unit having binding affinity to CD22 and a second binding unit having binding affinity to CD3, wherein the first binding unit comprises: (a) a CDR1 having two or fewer substitutions in any of the amino acid sequences of SEQ ID NOs: 1 to 10; and/or (b) a CDR2 having two or fewer substitutions in any of the amino acid sequences of SEQ ID NOs: 11 to 17; and/or (c) a CDR3 having two or fewer substitutions in any of the amino acid sequences of SEQ ID NOs: 18 to 23. In some embodiments, the CDR1, CDR2, and CDR3 sequences of the first binding unit are present in a human framework. In some embodiments, the first binding unit further comprises a heavy chain constant region sequence in the absence of a CH1 sequence.

In some embodiments, the first binding unit comprises a heavy chain variable region comprising: (a) a CDR1 sequence selected from the group consisting of SEQ ID NOs: 1 to 10; and/or (b) a CDR2 sequence selected from the group consisting of SEQ ID NOs: 11 to 17; and/or (c) a CDR3 sequence selected from the group consisting of SEQ ID NOs: 18 to 23.

In some embodiments, the multi-specific binding compound comprises: (a) a CDR1 sequence selected from the group consisting of SEQ ID NOs: 1 to 10; and (b) a CDR2 sequence selected from the group consisting of SEQ ID NOs: 11 to 17; and (c) a CDR3 sequence selected from the group consisting of SEQ ID NOs: 18 to 23.

In some embodiments, the multi-specific binding compound comprises: (a) a CDR1 sequence of SEQ ID NO: 1, a CDR2 sequence of SEQ ID NO: 11, and a CDR3 sequence of SEQ ID NO: 18; (b) a CDR1 sequence of SEQ ID NO: 1, a CDR2 sequence of SEQ ID NO: 12, and a CDR3 sequence of SEQ ID NO: 19; or (c) a CDR1 sequence of SEQ ID NO: 1, a CDR2 sequence of SEQ ID NO: 12, and a CDR3 sequence of SEQ ID NO: 20. In some embodiments, the multi-specific binding compound comprises a heavy chain variable region having at least 95% sequence identity to any one of the sequences of SEQ ID NOs: 24 to 84. In some embodiments, the multi-specific binding compound comprises a heavy chain variable region sequence selected from the group consisting of SEQ ID NOs: 24 to 84. In some embodiments, the multi-specific binding compound comprises a heavy chain variable region sequence of SEQ ID NO: 24.

Aspects of the invention include multi-specific binding compounds comprising a first binding unit having binding affinity to CD22 and a second binding unit having binding affinity to CD3, wherein the first binding unit comprises a heavy chain variable region comprising: (a) a CDR1 sequence of the formula: G $X_1$ S I $X_2$ $X_3$ $X_4$ $X_5$ $X_6$ Y (SEQ ID NO: 104), where $X_1$ is D or G; $X_2$ is S, T, I or N; $X_3$ is S or D; $X_4$ is G, S or N; $X_5$ is D, G or S; and $X_6$ is Y or H; and (b) a CDR2 sequence of the formula: $X_7$ $X_8$ Y $X_9$ G $X_{10}$ $X_{11}$ (SEQ ID NO: 105) where $X_7$ is I or V; $X_8$ is Y or H; $X_9$ is S or T; $X_{10}$ is A, V or S; and $X_{11}$ is T or A; and (c) a CDR3 sequence of the formula: $X_{12}$ R $X_{13}$ D S S $X_{14}$ W R S (SEQ ID NO: 106) where $X_{12}$ is T, A or K; $X_{13}$ is D or E; and $X_{14}$ is N or S.

Aspects of the invention include multi-specific binding compounds comprising a first binding unit having binding affinity to CD22 and a second binding unit having binding affinity to CD3, wherein the first binding unit comprises a heavy chain variable region comprising CDR1, CDR2 and CDR3 sequences in a human VH framework, wherein the CDR sequences comprise a sequence having two or fewer substitutions in a CDR sequence selected from the group consisting of SEQ ID NOs: 1-23.

Aspects of the invention include multi-specific binding compounds comprising a first binding unit having binding affinity to CD22 and a second binding unit having binding affinity to CD3, wherein the first binding unit comprises a heavy chain variable region comprising CDR1, CDR2 and CDR3 sequences in a human VH framework, wherein the CDR sequences are selected from the group consisting of SEQ ID NOs: 1-23.

Aspects of the invention include multi-specific binding compounds comprising a first binding unit having binding affinity to CD22 and a second binding unit having binding affinity to CD3, wherein the first binding unit comprises a heavy chain variable region comprising: (a) a CDR1 sequence of SEQ ID NO: 1, a CDR2 sequence of SEQ ID NO: 11, and a CDR3 sequence of SEQ ID NO: 18; or (b) a CDR1 sequence of SEQ ID NO: 1, a CDR2 sequence of SEQ ID NO: 12, and a CDR3 sequence of SEQ ID NO: 19; or (c) a CDR1 sequence of SEQ ID NO: 1, a CDR2 sequence of SEQ ID NO: 12, and a CDR3 sequence of SEQ ID NO: 20, in a human VH framework.

In some embodiments, the multi-specific binding compound is bispecific. In some embodiments, the multi-specific binding compound is in a CAR-T format.

Aspects of the invention include multi-specific binding compounds comprising: (i) a heavy chain variable region having binding affinity to CD3, comprising a CDR1 sequence of SEQ ID NO: 85, a CDR2 sequence of SEQ ID NO: 86, and CDR3 sequence of SEQ ID NO: 87, in a human VH framework; (ii) a light chain variable region comprising a CDR1 sequence of SEQ ID NO: 88, a CDR2 sequence of SEQ ID NO: 89, and CDR3 sequences of SEQ ID NO: 90, in a human VL framework; and (iii) an antigen-binding domain of an anti-CD22 heavy chain antibody, comprising a CDR1 sequence of SEQ ID NO: 1, a CDR2 sequence of SEQ ID NO: 11, and a CDR3 sequence of SEQ ID NO: 18, in a human VH framework.

Aspects of the invention include multi-specific binding compounds comprising: (i) a heavy chain variable region having binding affinity to CD3, comprising a CDR1 sequence of SEQ ID NO: 85, a CDR2 sequence of SEQ ID NO: 86, and CDR3 sequence of SEQ ID NO: 87, in a human VH framework; (ii) a light chain variable region comprising a CDR1 sequence of SEQ ID NO: 88, a CDR2 sequence of SEQ ID NO: 89, and CDR3 sequences of SEQ ID NO: 90, in a human VL framework; and (iii) an antigen-binding domain of an anti-CD22 heavy chain antibody, comprising a CDR1 sequence of SEQ ID NO: 1, a CDR2 sequence of SEQ ID NO: 12, and a CDR3 sequence of SEQ ID NO: 19, in a human VH framework.

Aspects of the invention include multi-specific binding compound comprising: (i) a heavy chain variable region having binding affinity to CD3, comprising a CDR1 sequence of SEQ ID NO: 85, a CDR2 sequence of SEQ ID NO: 86, and CDR3 sequence of SEQ ID NO: 87, in a human VH framework; (ii) a light chain variable region comprising a CDR1 sequence of SEQ ID NO: 88, a CDR2 sequence of SEQ ID NO: 89, and CDR3 sequences of SEQ ID NO: 90, in a human VL framework; and (iii) an antigen-binding domain of an anti-CD22 heavy chain antibody, comprising a CDR1 sequence of SEQ ID NO: 1, a CDR2 sequence of SEQ ID NO: 12, and a CDR3 sequence of SEQ ID NO: 20, in a human VH framework.

In some embodiments, the multispecific binding compound comprises a human IgG1 Fc region. In some embodiments, the human IgG1 Fc region is a silenced human IgG1 Fc region. In some embodiments, the multispecific binding compound comprises a human IgG4 Fc region. In some embodiments, the human IgG4 Fc region is a silenced human IgG4 Fc region.

Aspects of the invention include pharmaceutical compositions comprising a multi-specific binding compound as described herein.

Aspects of the invention include methods for the treatment of a B-cell disorder characterized by expression of CD22, comprising administering to a subject with said disorder a multi-specific binding compound or a pharmaceutical composition as described herein.

Aspects of the invention include use of a multi-specific binding compound in the preparation of a medicament for the treatment of a B-cell disorder characterized by expression of CD22.

In some embodiments, the disorder is diffuse large B cell lymphoma (DLBCL). In some embodiments, the disorder is non-Hodgkin's lymphoma (NHL). In some embodiments, the disorder is systemic lupus erythematosus (SLE). In some embodiments, the disorder is rheumatoid arthritis (RA). In some embodiments, the disorder is multiple sclerosis (MS).

Aspects of the invention include polynucleotides encoding a multi-specific binding compound as described herein. Aspects of the invention include vectors comprising the polynucleotides as described herein. Aspects of the invention include cells comprising the vectors as described herein.

Aspects of the invention include methods of producing a multi-specific binding compound as described herein, comprising growing a cell as described herein under conditions permissive for expression of the binding compound, and isolating the binding compound from the cell.

Aspects of the invention include methods of making a multi-specific binding compound as described herein, comprising immunizing a UniRat animal with CD22 and identifying CD22-binding heavy chain sequences.

Aspects of the invention include methods of treatment, comprising administering to an individual an effective dose of a multi-specific binding compound as described herein, or a pharmaceutical composition as described herein.

These and further aspects will be further explained in the rest of the disclosure, including the Examples.

BRIEF DESCRIPTION OF THE DRAWINGS

FIG. 16 is table showing data for various biological activities of anti-CD22 antibodies in accordance with embodiments of the invention.

DETAILED DESCRIPTION OF THE PREFERRED EMBODIMENTS

Figure 1A:
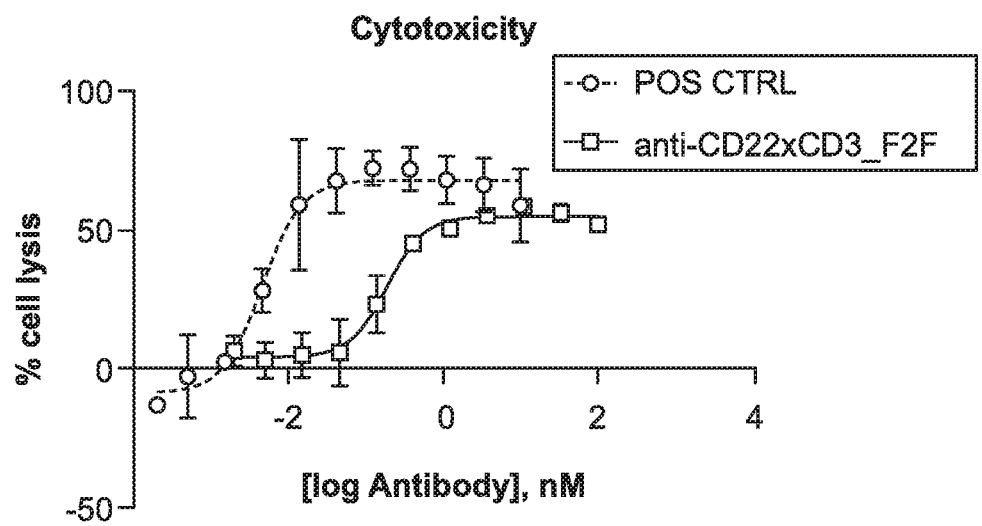
FIG. 1A is a graph depicting T cell mediated cytotoxicity of CD22 positive cells (Daudi) using resting human pan T cells.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

Antibodies, also referred to as immunoglobulins, conventionally comprise at least one heavy chain and one light chain, where the amino terminal domain of the heavy and light chains is variable in sequence, hence is commonly referred to as a variable region domain, or a variable heavy (VH) or variable light (VH) domain. The two domains conventionally associate to form a specific binding region, although as will be discussed here, specific binding can also be obtained with heavy chain-only variable sequences, and a variety of non-natural configurations of antibodies are known and used in the art.

A "functional" or "biologically active" antibody or antigen-binding molecule (including heavy chain-only antibodies and multi-specific (e.g., bispecific) three-chain antibody-like molecules (TCAs), described herein) is one capable of exerting one or more of its natural activities in structural, regulatory, biochemical or biophysical events. For example, a functional antibody or other binding molecule, e.g., a TCA, may have the ability to specifically bind an antigen and the binding may in turn elicit or alter a cellular or molecular event such as signal transduction or enzymatic activity. A functional antibody or other binding molecule, e.g., a TCA, may also block ligand activation of a receptor or act as an agonist or antagonist. The capability of an antibody or other binding molecule, e.g., a TCA, to exert one or more of its natural activities depends on several factors, including proper folding and assembly of the polypeptide chains.

The term "antibody" herein is used in the broadest sense and specifically covers monoclonal antibodies, polyclonal antibodies, monomers, dimers, multimers, multispecific antibodies (e.g., bispecific antibodies), heavy chain-only antibodies, three chain antibodies, single chain Fv (scFv), nanobodies, etc., and also includes antibody fragments, so long as they exhibit the desired biological activity (Miller et al (2003) Jour. of Immunology 170:4854-4861). Antibodies may be murine, human, humanized, chimeric, or derived from other species.

The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof, such targets including but not limited to, a cancer cell, or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. The immunoglobulins can be derived from any species. In one aspect, the immunoglobulin is of largely human origin.

The term "monoclonal antibody" as used herein refers to an antibody obtained from a population of substantially homogeneous antibodies, i.e., the individual antibodies comprising the population are identical except for possible naturally occurring mutations that may be present in minor amounts.

Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies in accordance with the present invention can be made by the hybridoma method first described by Kohler et al. (1975) *Nature* 256:495, and can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" residues 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." *Mol Immunol.* 2010; 47:694-700), which is based on sequence variability and is the most commonly used. The Chothia definition is based on the location of the structural loop regions (Chothia et al. "Conformations of immunoglobulin hypervariable regions." *Nature.* 1989; 342:877-883). Alternative CDR definitions of interest include, without limitation, those disclosed by Honegger, "Yet another numbering scheme for immunoglobulin variable domains: an automatic modeling and analysis tool." *J Mol Biol.* 2001; 309:657-670; Ofran et al. "Automated identification of complementarity determining regions (CDRs) reveals peculiar characteristics of CDRs and B cell epitopes." *J Immunol.* 2008; 181:6230-6235; Almagro "Identification of differences in the specificity-determining residues of antibodies that recognize antigens of different size: implications for the rational design of antibody repertoires." *J Mol Recognit.* 2004; 17:132-143; and Padlan et al. "Identification of specificity-determining residues in antibodies." Faseb J. 1995; 9:133-139, each of which is herein specifically incorporated by reference.

The terms "heavy chain-only antibody," and "heavy-chain antibody" are used interchangeably herein and refer, in the broadest sense, to antibodies lacking the light chain of a conventional antibody. The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs™). In one embodiment, a heavy chain-only antibody is composed of the variable region antigen-binding domain composed of framework 1, CDR1, framework 2, CDR2, framework 3, CDR3, and framework 4. In another embodiment, the heavy chain-only antibody is composed of an antigen-binding domain, at least part of a hinge region and CH2 and CH3 domains. In another embodiment, the heavy chain-only antibody is composed of an antigen-binding domain, at least part of a hinge region and a CH2 domain. In a further embodiment, the heavy chain-only antibody is composed of an antigen-binding domain, at least part of a hinge region and a CH3 domain. Heavy chain-only antibodies in which the CH2 and/or CH3 domain is truncated are also included herein. In a further embodiment the heavy chain is composed of an antigen binding domain, and at least one CH (CH1, CH2, CH3, or CH4) domain but no hinge region. In a further embodiment the heavy chain is composed of an antigen binding domain, at least one CH (CH1, CH2, CH3, or CH4) domain, and at least a portion of a hinge region. The heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, the heavy-chain antibody is of the IgG1, IgG2, IgG3, or IgG4 subtype, in particular the IgG1 subtype. In one embodiment, the heavy-chain antibody is of the IgG4 subtype, wherein one or more of the CH domains are modified to alter an effector function of the antibody. In one embodiment, the heavy-chain antibody is of the IgG1 subtype, wherein one or more of the CH domains are modified to alter an effector function of the antibody. Modifications of CH domains that alter effector function are further described herein. Non-limiting examples of heavy-chain antibodies are described, for example, in WO2018/039180, the disclosure of which is incorporated herein by reference in its entirety.

In one embodiment, the heavy chain-only antibodies herein are used as a binding (targeting) domain of a chimeric antigen receptor (CAR). The definition specifically includes human heavy chain-only antibodies produced by human immunoglobulin transgenic rats (UniRat™), called UniAbs™. The variable regions (VH) of UniAbs™ are called UniDabs™, and are versatile building blocks that can be linked to Fc regions or serum albumin for the development of novel therapeutics with multi-specificity, increased potency and extended half-life. Since the homodimeric UniAbs™ lack a light chain and thus a VL domain, the antigen is recognized by one single domain, i.e., the variable domain (antigen-binding domain) of the heavy chain of a heavy-chain antibody (VH).

An "intact antibody chain" as used herein is one comprising a full length variable region and a full length constant region (Fc). An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310). The light chains of antibodies from any vertebrate species can be assigned to one of two types, called κ and λ based on the amino acid sequences of their constant domains.

A "functional Fc region" possesses an "effector function" of a native-sequence Fc region. Non-limiting examples of effector functions include C1q binding; CDC; Fc-receptor binding; ADCC; ADCP; down-regulation of cell-surface receptors (e.g., B-cell receptor), etc. Such effector functions generally require the Fc region to interact with a receptor, e.g., the FcγRI; FcγRIIA; FcγRIIB1; FcγRIIB2; FcγRIIIA; FcγRIIIB receptors, and the low affinity FcRn receptor; and can be assessed using various assays known in the art. A "dead" or "silenced" Fc is one that has been mutated to retain activity with respect to, for example, prolonging serum half-life, but which does not activate a high affinity Fc receptor, or which has a reduced affinity to an Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences may include three amino acid substitutions in the CH2 region to reduce FcγRI binding at EU index positions 234, 235, and 237 (see Duncan et al., (1988) Nature 332:563). Two amino acid substitutions in the complement C1q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 or IgG2 residues at positions 233-236 and IgG4 residues at positions 327, 330 and 331 greatly reduces ADCC and CDC (see, for example, Armour K L. et al., 1999 Eur J Immunol. 29(8): 2613-24; and Shields R L. et al., 2001. J Biol Chem. 276(9):6591-604). The human IgG1 amino acid sequence (UniProtKB No. P01857) is provided herein as SEQ ID NO: 93. The human IgG4 amino acid sequence (UniProtKB No. P01861) is provided herein as SEQ ID NO: 94. Silenced IgG1 is described, for example, in Boesch, A. W., et al., "Highly parallel characterization of IgG Fc binding interactions." MAbs, 2014. 6(4): p. 915-27, the disclosure of which is incorporated herein by reference in its entirety.

Other Fc variants are possible, including, without limitation, one in which a region capable of forming a disulfide bond is deleted, or in which certain amino acid residues are eliminated at the N-terminal end of a native Fc, or a methionine residue is added thereto. Thus, in some embodiments, one or more Fc portions of a binding compound can comprise one or more mutations in the hinge region to eliminate disulfide bonding. In yet another embodiment, the hinge region of an Fc can be removed entirely. In still another embodiment, a binding compound can comprise an Fc variant.

Further, an Fc variant can be constructed to remove or substantially reduce effector functions by substituting (mutating), deleting or adding amino acid residues to effect complement binding or Fc receptor binding. For example, and not limitation, a deletion may occur in a complement-binding site, such as a C1q-binding site. Techniques for preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, an antibody having an Fc region according to this invention can comprise an antibody with or without K447.

Aspects of the invention include binding compounds having multi-specific configurations, which include, without limitation, bispecific, trispecific, etc. A large variety of methods and protein configurations are known and used in bispecific monoclonal antibodies (BsMAB), tri-specific antibodies, etc.

Various methods for the production of multivalent artificial antibodies have been developed by recombinantly fusing variable domains of two or more antibodies. In some embodiments, a first and a second antigen-binding domain on a polypeptide are connected by a polypeptide linker One non-limiting example of such a polypeptide linker is a GS linker, having an amino acid sequence of four glycine residues, followed by one serine residue, and wherein the sequence is repeated n times, where n is an integer ranging from 1 to about 10 (SEQ ID NO: 107), such as 2, 3, 4, 5, 6, 7, 8, or 9. Non-limiting examples of such linkers include GGGGS (SEQ ID NO: 102) (n=1) and GGGGSGGGGS (SEQ ID NO: 103) (n=2). Other suitable linkers can also be used, and are described, for example, in Chen et al., Adv Drug Deliv Rev. 2013 Oct. 15; 65(10): 1357-69, the disclosure of which is incorporated herein by reference in its entirety.

The term "three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy-chain only antibody comprising an Fc portion comprising CH2 and/or CH3 and/or CH4 domains, in the absence of a CH1 domain, and one or more antigen binding domains (e.g., two antigen binding domains) that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments. A TCA protein makes use of a heavy chain-only antibody as hereinabove defined.

A TCA binding compound makes use of a "heavy chain only antibody" or "heavy chain antibody" or "heavy chain polypeptide" which, as used herein, mean a single chain antibody comprising heavy chain constant regions CH2 and/or CH3 and/or CH4 but no CH1 domain. In one embodiment, the heavy chain antibody is composed of an antigen-binding domain, at least part of a hinge region and CH2 and CH3 domains. In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain. Heavy chain antibodies in which the CH2 and/or CH3 domain is truncated are also included herein. In a further embodiment, the heavy chain is composed of an antigen binding domain, and at least one CH (CH1, CH2, CH3, or CH4) domain but no hinge region. The heavy chain only antibody can be in the form of a dimer, in which two heavy chains are disulfide bonded other otherwise covalently or non-covalently attached with each other, and can optionally include an asymmetric interface between two or more of the CH domains to facilitate proper pairing between polypeptide chains. The heavy-chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype or the IgG4 subtype. Non-limiting examples of a TCA binding compound are described in, for example, WO2017/223111 and WO2018/052503, the disclosures of which are incorporated herein by reference in their entirety.

Heavy-chain antibodies constitute about one fourth of the IgG antibodies produced by the camelids, e.g., camels and llamas (Hamers-Casterman C., et al. Nature. 363, 446-448 (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. J. Biol. Chem. 276, 26285-26290 (2001)). Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)). Sharks have also been shown to have a single VH-like domain in their antibodies, termed VNAR. (Nuttall et al. Eur. J. Biochem. 270, 3543-3554 (2003); Nuttall et al. Function and Bioinformatics 55, 187-197 (2004); Dooley et al., Molecular Immunology 40, 25-33 (2003)).

The terms "CD22" and "cluster of differentiation-22" as used herein refer to a molecule belonging to the SIGLEC family of lectins, found on the surface of mature B cells, and to a lesser extent on some immature B cells. The term "CD22" includes a CD22 protein of any human and non-human animal species, and specifically includes human CD22 as well as CD22 of non-human mammals.

The term "human CD22" as used herein includes any variants, isoforms and species homologs of human CD22 (UniProt P20273), regardless of its source or mode of preparation. Thus, "human CD22" includes human CD22 naturally expressed by cells and CD22 expressed on cells transfected with the human CD22 gene.

The terms "anti-CD22 heavy chain-only antibody," "CD22 heavy chain-only antibody," "anti-CD22 heavy chain antibody" and "CD22 heavy chain antibody" are used herein interchangeably to refer to a heavy chain-only antibody as hereinabove defined, immunospecifically binding to CD22, including human CD22, as hereinabove defined. The definition includes, without limitation, human heavy chain antibodies produced by transgenic animals, such as transgenic rats or transgenic mice expressing human immunoglobulin, including UniRats™ producing human anti-CD22 UniAb™ antibodies, as hereinabove defined.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. The terms "multi-specific antibody," "multi-specific heavy chain-only antibody," "multi-specific heavy chain antibody," "multi-specific UniAb™", and "multi-specific binding compound" are used herein in the broadest sense and cover all antibodies with more than one binding specificity. The multi-specific heavy chain anti-CD22 antibodies of the present invention specifically include antibodies immunospecifically binding to one single epitope on a CD22 protein, such as a human CD22, and to an epitope on a different protein, such as, for example, a CD3 protein (i.e., bivalent and monoparatopic). The multi-specific heavy chain anti-CD22 antibodies of the present invention specifically include antibodies immunospecifically binding to two or more non-overlapping epitopes on a CD22 protein, such as a human CD22 (i.e., bivalent and biparatopic). The multi-specific heavy chain anti-CD22 antibodies of the present invention also specifically include antibodies immunospecifically binding to an epitope on a CD22 protein, such as human CD22 and to an epitope on a different protein, such as, for example, a CD3 protein, such as human CD3 (i.e., bivalent and biparatopic). The multi-specific heavy chain anti-CD22 antibodies of the present invention also specifically include antibodies immunospecifically binding to two or more non-overlapping or partially overlapping epitopes on a CD22 protein, such as a human CD22 protein, and to an epitope on a different protein, such as, for example, a CD3 protein, such as human CD3 protein (i.e., trivalent and biparatopic).

Antibodies of the invention include monospecific antibodies, having one binding specificity. Monospecific antibodies specifically include antibodies comprising a single binding specificity, as well as antibodies comprising more than one binding unit having the same binding specificity. The terms "monospecific antibody," "monospecific heavy chain-only antibody," "monospecific heavy chain antibody," and "monospecific UniAb™" are used herein in the broadest sense and cover all antibodies with one binding specificity. The monospecific heavy chain anti-CD22 antibodies of the present invention specifically include antibodies immunospecifically binding to one epitope on a CD22 protein, such as a human CD22 (monovalent and monospecific). The monospecific heavy chain anti-CD22 antibodies of the present invention also specifically include antibodies having more than one binding unit (e.g., multivalent antibodies) immunospecifically binding to an epitope on a CD22 protein, such as human CD22. For example, a monospecific antibody in accordance with embodiments of the invention can include a heavy chain variable region comprising two antigen-binding domains, wherein each antigen-binding domain binds to the same epitope on a CD22 protein (i.e., bivalent and monospecific).

An "epitope" is the site on the surface of an antigen molecule to which a single antibody molecule binds. Generally, an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present invention specifically includes anti-CD22 heavy chain antibodies with polyepitopic specificities, i.e., anti-CD22 heavy chain antibodies binding to one or more non-overlapping epitopes on a CD22 protein, such as a human CD22; and anti-CD22 heavy chain antibodies binding to one or more epitopes on a CD22 protein and to an epitope on a different protein, such as, for example, a CD3 protein. The term "non-overlapping epitope(s)" or "non-competitive epitope(s)" of an antigen is defined herein to mean epitope(s) that are recognized by one member of a pair of antigen-specific antibodies but not the other member. Pairs of antibodies, or antigen-binding regions targeting the same antigen on a multi-specific antibody, recognizing non-overlapping epitopes, do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "monovalent" antibody has one binding site. Thus a monovalent antibody is also monospecific.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent. A bivalent antibody in accordance with embodiments of the invention may have two binding sites to the same epitope (i.e., bivalent, monoparatopic), or to two different epitopes (i.e., bivalent, biparatopic).

A large variety of methods and protein configurations are known and used for the preparation of bispecific monoclonal antibodies (BsMAB), tri-specific antibodies, and the like.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T cell to create a chimeric antigen receptor (CAR). (*J Natl Cancer Inst*, 2015; 108(7):dvj439; and Jackson et al., *Nature Reviews Clinical Oncology*, 2016; 13:370-383).

The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T cell receptors or FcRs and perform effector functions. Preferably, the cells express at least FcγRIII and perform ADCC effector function. Examples of human leukocytes which mediate ADCC include natural killer (NK) cells, monocytes, cytotoxic T cells and neutrophils, with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B cells and T cells including cytolytic T cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, Calif.) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen*, 12(8), 791-800, 2009).

The terms "treatment", "treating" and the like are used herein to generally mean obtaining a desired pharmacologic and/or physiological effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "B-cell neoplasms" or "mature B-cell neoplasms" in the context of the present invention include small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma (DLBCL), multiple myeloma, lymphoplasmacytic lymphoma, splenic marginal zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

The term "characterized by expression of CD22" broadly refers to any disease or disorder in which CD22 expression is associated with or involved with one or more pathological processes that are characteristic of the disease or disorder. Such disorders include, but are not limited to, B-cell neoplasms.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomeriation), clipping/hydrolysis/fragmentation (e.g., hinge region fragmentation), succinimide formation, unpaired cysteine(s), N-terminal extension, C-terminal processing, glycosylation differences, etc.

II. Detailed Description

Anti-CD22 Antibodies

Aspects of the invention include multispecific binding compounds that comprise an anti-CD22 binding domain. A family of closely related heavy chain-only antibody binding domains that bind to human CD22 are provided herein. The antibodies of this family comprise a set of CDR sequences as defined herein and shown in Table 1, and are exemplified by the provided heavy chain variable region (VH) sequences of SEQ ID NOs: 24 to 84 set forth in Table 2. The antibodies described herein provide a number of benefits that contribute to utility as clinically therapeutic agent(s). The antibodies include members with a range of binding affinities, allowing the selection of a specific sequence with a desired binding affinity.

TABLE 1

Anti-CD22 heavy chain antibody unique CDR amino acid sequences.

| SEQ_aa_CDR1 | SEQ_aa_CDR2 | SEQ_aaCDR3 |
|---|---|---|
| GDSISSGDYY (SEQ ID NO: 1) | IYYSGVT (SEQ ID NO: 11) | TREDSSNWRS (SEQ ID NO: 18) |
| GDSISSGGYY (SEQ ID NO: 2) | IYYSGAT (SEQ ID NO: 12) | TRDDSSNWRS (SEQ ID NO: 19) |
| GGSISSGDYY (SEQ ID NO: 3) | IYYSGST (SEQ ID NO: 13) | TREDSSSWRS (SEQ ID NO: 20) |
| GGSISSSSYY (SEQ ID NO: 4) | IYYTGST (SEQ ID NO: 14) | AREDSSSWRS (SEQ ID NO: 21) |
| GGSFSGYY (SEQ ID NO: 5) | VYYTGAT (SEQ ID NO: 15) | KRDDSSNWRS (SEQ ID NO: 22) |
| GDSISSSSYY (SEQ ID NO: 6) | IHYSGST (SEQ ID NO: 16) | ARDDSSNWRS (SEQ ID NO: 23) |
| GGSITSSSYY (SEQ ID NO: 7) | IYYSGSA (SEQ ID NO: 17) | |
| GGSISSSSHY (SEQ ID NO: 8) | | |
| GGSIISSSYY (SEQ ID NO: 9) | | |
| GGSINDNSHY (SEQ ID NO: 10) | | |

TABLE 2

Anti-CD22 heavy chain antibody variable domain amino acid sequences.

| Clone ID # | SEQ_aa_FR1_FR4 | SEQ ID NO: |
|---|---|---|
| 335207 | QLQLQESGPGLVKPSETLSLTCTVSGDSISSGDYYWGWIRQPPGKGLEWIG HIYYSGVTYYNPSLKSRVTISVDTSRNQFSLKLSSVTAADTAVYYCTREDSS NWRSRGQGTLVTVSS | 24 |
| 335161 | QLQLQESGPGLVKPSETLSLTCTVSGDSISSGDYYWGWIRQPPGKGLEWIG HIYYSGATYYNPSLENRVTISVDTSKNQFSLKLSSVTAADTAVYYCTRDDS SNWRSRGQGTLVTVSS | 25 |
| 335254 | QLQLQESGPGLVKPSETLSLTCTVSGDSISSGDYYWGWIRQPPGKGLEWIG HIYYSGVTYYNPSLKNRVTISVDTSKNQFSLKLSSVTAADTAVYYCTREDS SSWRSRGQGTLVTVSS | 26 |
| 335260 | QLQLQESGPGLVKPSETLSLTCTVSGDSISSGDYYWGWIRQPPGKGLEWIG HIYYSGVTYYNPSLKNRVTISVDTSRNQFSLNLSSVTAADTAVYYCTREDS SSWRSRGQGTLVTVSS | 27 |
| 335151 | QLQLQESGPGLVKPSETLSLTCTVSGDSISSGDYYWGWIRQPPGKGLEWIG HIYYSGATYYNPSLKNRVTISVDTSRNQFSLNLSSVTAADTAVYYCTRDDS SNWRSRGQGTLVTVSS | 28 |

TABLE 2-continued

Anti-CD22 heavy chain antibody variable domain amino acid sequences.

| Clone ID # | SEQ_aa_FR1_FR4 | SEQ ID NO: |
|---|---|---|
| 335170 | QLQLQESGPGLVKPSETLSLTCTVSGDSISSGDYYWGWIRQPPGKGLEWIG<br>HIYYSGATYYNPSLKNRVTISVDTSRNQFSLKLSSVTAADTAVYYCTRDDS<br>SNWRSRGQGTLVTVSS | 29 |
| 335176 | QLQLQESGPGLVKPSETLSLTCTVSGDSISSGDYYWGWIRQPPGKGLEWIG<br>HIYYSGATYYNPSLKNRVTISVDTSKNQFSLKLSSVTAADTAVYYCTRDDS<br>SNWRSRGQGTLVTVSS | 30 |
| 335181 | QLQLQESGPGLVKPSETLSLTCTVSGDSISSGGYYWGWIRQPPGKGLEWIG<br>HIYYSGATYYNPSLKNRVTISVDTSKNQFSLKLSSVTAADTAVYYCTRDDS<br>SNWRSRGQGTLVTVSS | 31 |
| 335244 | QLQLQESGPGLVKPSETLSLTCTVSGDSISSGDYYWGWIRQPPGKGLEWIG<br>HIYYSGATYYNPSLKNRVTISVDTSRNQFSLNLSSVTAADTAVYYCTREDS<br>SSWRSRGQGTLVTVSS | 32 |
| 335154 | QLQLQESGPGLVKPSETLSLTCTVSGDSISSGDYYWGWIRQPPGKGLEWIG<br>HIYYSGVTYYNPSLKNRVTISVDTSKNQFSLKLSSVTAADTAVYYCTRDDS<br>SNWRSRGQGTLVTVSS | 33 |
| 335201 | QLQLQESGPGLVKPSETLSLTCTVSGDSISSGDYYWGWIRQPPGKGLEWIG<br>HIYYSGVTYYNPSLKNRVTISVDTSRNQFSLKLSSVTAADTAVYYCTREDS<br>SNWRSRGQGTLVTVSS | 34 |
| 335261 | QLQLQESGPGLVKPSETLSLTCTVSGDSISSGDYYWGWIRQPPGKGLEWIG<br>HIYYSGATYYNPSLENRVTISVDTSKNQFSLKLSSVTAADTAVYYCTREDS<br>SSWRSRGQGTLVTVSS | 35 |
| 335293 | QLQLQESGPGLVKPSETLSLTCTVSGDSISSGDYYWGWIRQPPGKGLEWIG<br>HIYYSGATYYNPSLKNRVTISVDTSRNQFSLKLSSVTAADTAVYYCTREDS<br>SSWRSRGQGTLVTVSS | 36 |
| 335203 | QLQLQESGPGLVKPSETLSLTCTVSGDSISSGDYYWGWIRQPPGKGLEWIG<br>HIYYSGVTYYNPSLKNRVTISVDTSKNQFSLKLSSVTAADTAVYYCTREDS<br>SNWRSRGQGTLVTVSS | 37 |
| 335185 | QLQLQESGPGLVKPSETLSLTCTVSGDSISSGDYYWGWIRQPPGKGLEWIG<br>HIYYSGATYYNPSLKNRVTISVDTSRNQFSLNLSSVTAADTAVYYCTREDS<br>SNWRSRGQGTLVTVSS | 38 |
| 335206 | QLQLQESGPGLVKPSETLSLTCTVSGDSISSGDYYWGWIRQPPGKGLEWIG<br>HIYYSGATYYNPSLKNRVTISVDTSRNQFSLKLSSVTAADTAVYYCTREDS<br>SNWRSRGQGTLVTVSS | 39 |
| 335245 | QLQLQESGPGLVKPSETLSLTCTVSGDSISSGDYYWGWIRQPPGKGLEWIG<br>HIYYSGATYYNPSLKNRVTISVDTSKNQFSLKLSSVTAADTAVYYCTREDS<br>SSWRSRGQGTLVTVSS | 40 |
| 335218 | QLQLQESGPGLVKPSETLSLTCTVSGDSISSGDYYWGWIRQPPGKGLEWIG<br>HIYYSGATYYNPSLKNRVTISVDTSRNQFSLKLSSVTAADTAVYYCTREDS<br>SNWRSRGQGTLVTVSS | 41 |
| 335160 | QLQLQESGPGLVKPSETLSLTCTVSGDSISSGDYYWGWIRQPPGKGLEWIG<br>SIYYSGATYYNPSLKNRVTISVDTSKNQFSLKLSSVTAADTAVYYCTRDDS<br>SNWRSRGQGTLVTVSS | 42 |
| 335158 | QLQLQESGPGLVKPSETLSLTCTVSGGSISSGDYYWGWIRQPPGKGLEWIG<br>HIYYSGATYYNPSLKNRVTISVDTSRNQFSLKLSSVTAADTAVYYCTRDDS<br>SNWRSRGQGTLVTVSS | 43 |
| 324508 | QLQLQESGPGLVKPSETLSLTCTVSGGSISSGDYYWGWIRQPPGKGLEWIG<br>HIYYSGATYYNPSLENRVTISVDTSKNQFSLKLSSVTAADTAVYYCTRDDS<br>SNWRSRGQGTLVTVSS | 44 |
| 335307 | QLQLQESGPGLVKPSETLSLTCTVSGDSISSGDYYWGWIRQPPGKGLEWIG<br>SIYYSGSTYYNPSLKSRVTISVDTSKNQFSLKLSSVTAADTAVYYCTREDSS<br>SWRSRGQGTLVTVSS | 45 |
| 335301 | QLQLQESGPGLVKPSETLSLTCTVSGDSISSGDYYWGWIRQPPGKGLEWIG<br>NIYYSGATYYNPSLKNRVTISVDTSKNQFSLKLSSVTAADTAVYYCTREDS<br>SSWRSRGQGTLVTVSS | 46 |

TABLE 2-continued

Anti-CD22 heavy chain antibody variable domain amino acid sequences.

| Clone ID # | SEQ_aa_FR1_FR4 | SEQ ID NO: |
|---|---|---|
| 335323 | QLQLQESGPGLVKPSETLSLTCTVSGDSISSGGYYWGWIRQPPGKGLEWIG SIYYSGSTYYNPSLKNRVTISVDTSKNQFSLKLSSVTAADTAVYYCTREDSS SWRSRGQGTLVTVSS | 47 |
| 335271 | QLQLQESGPGLVKPSETLSLTCTVSGDSISSGDYYWGWIRHPPGKGLEWIG HIYYSGATYYNPSLKNRVTISVDTSKNQFSLKLSSVTAADTAVYYCTREDS SSWRSRGQGTLVTVSS | 48 |
| 335234 | QLQLQESGPGLVKPSETLSLTCTVSGDSISSGDYYWGWIRQPPGKGLEWIG NIYYSGATYYNPSLKNRVTISVDTSKNQFSLKLSSVTAADTAVYYCTREDS SNWRSRGQGTLVTVSS | 49 |
| 335182 | QLQLQESGPGLVKPSETLSLTCTVSGDSISSGDYYWGWIRQPPGKGLEWIG NIYYSGATYYNPSLKNRVTISVDTSKNQFSLKLSSVTAADTAVYYCTRDDS SNWRSRGQGTLVTVSS | 50 |
| 335186 | QLQLQESGPGLVKPSETLSLTCTVSGGSISSSSYYWGWIRQPPGKGLEWIGS IYYSGSTYYNPSLKSRVTISVDTSKNQFSLKLSSVTAADTAVYYCTRDDSSN WRSRGQGTLVTVSS | 51 |
| 335233 | QLQLQESGPGLVKPSETLSLTCTVSGDSISSGDYYWGWIRQPPGKGLEWIG SIYYSGSTYYNPSLKSRVTISVDTSKNQFSLKLSSVTAADTAVYYCTREDSS NWRSRGQGTLVTVSS | 52 |
| 335224 | QLQLQESGPGLVKPSETLSLTCTVSGDSISSGDYYWGWIRQPPGKGLEWIG SIYYTGSTYYNPSLKSRVTISVDTSKNQFSLKLSSVTAADTAVYYCTREDSS NWRSRGQGTLVTVSS | 53 |
| 335210 | QLQLQESGPGLVKPSETLSLTCTVSGGSISSGDYYWGWIRQPPGKGLEWIG HIYYSGATYYNPSLKNRVTISVDTSRNQFSLKLSSVTAADTAVYYCTREDS SNWRSRGQGTLVTVSS | 54 |
| 335311 | QLQLQESGPGLVKPSETLSLTCAVYGGSFSGYYWGWIRQPPGKGLEWIGHI YYSGATYYNPSLKNRVTISVDTSRNQFSLNLSSVTAADTAVYYCTREDSSS WRSRGQGTLVTVSS | 55 |
| 335159 | QLQLQESGPGLVKPSETLSLTCTVSGGSISSSSYYWGWIRQPPGKGLEWIGH IYYSGVTYYNPSLKNRVTISVDTSKNQFSLKLSSVTAADTAAYYCTRDDSS NWRSRGQGTLVTVSS | 56 |
| 335188 | QLQLQESGPGLVKPSETLSLTCTVSGGSISSSSYYWGWIRQPPGKGLEWIGH IYYSGVTYYNPSLKNRVTISVDTSKNQFSLKLSSVTAADTAVYYCTRDDSS NWRSRGQGTLVTVSS | 57 |
| 335274 | QLQLQESGPGLVKPSETLSLTCTVSGGSISSSSYYWGWIRQPPGKGLEWIGS IYYSGSTYYNPSLKSRVTISVDTSRNQFSLNLSSVTAADTAVYYCTREDSSS WRSRGQGTLVTVSS | 58 |
| 335226 | QLQLQESGPGLVKPSETLSLTCTVSGDSISSSSYYWGWIRQPPGKGLEWIGS IYYSGSTYYNPSLKSRVTISVDTSKNQFSLKLSSVTAADTAVYYCTREDSSN WRSRGQGTLVTVSS | 59 |
| 335333 | QLQLQESGPGLVKPSETLSLTCTVSGGSISSSSYYWGWIRQPPGKGLEWIGS IYYSGSTYYNPSLKSRVTISVDTSKNQFSLKLSSVTAADTAVYYCAREDSSS WRSRGQGTLVTVSS | 60 |
| 335283 | QLQLQESGPGLVKPSETLSLTCTVSGGSISSSSYYWGWIRQPPGKGLEWIGS IYYSGATYYNPSLKNRVTISVDTSKNQFSLKLSSVTAADTAVYYCTREDSS SWRSRGQGTLVTVSS | 61 |
| 335297 | QLQLQESGPGLVKPSETLSLTCTVSGGSISSSSYYWGWIRQPPGKGLEWIGH IYYSGATYYNPSLKNRVTISVDTSRNQFSLNLSSVTAADTAVYYCTREDSSS WRSRGQGTLVTVSS | 62 |
| 335273 | QLQLQESGPGLVKPSETLSLTCTVSGGSISSSSYYWGWIRQPPGKGLEWIGS IYYSGSTYYNPSLKSRVTISVDTSKNQFSLKLSSVTAADTAVYYCTREDSSS WRSRGQGTLVTVSS | 63 |
| 335187 | QLQLQESGPGLVKPSETLSLTCTVSGGSISSSSYYWGWIRQPPGKGLEWIGH IYYSGATYYNPSLKNRVTISVDTSKNQFSLKLSSVTAADTAVYYCTRDDSS NWRSRGQGTLVTVSS | 64 |

TABLE 2-continued

Anti-CD22 heavy chain antibody variable domain amino acid sequences.

| Clone ID # | SEQ_aa_FR1_FR4 | SEQ ID NO: |
|---|---|---|
| 335295 | QLQLQESGPGLVKPSETLSLTCTVSGGSISSSSYYWGWIRQPPGKGLEWIGS IYYSGATYYNPSLKNRVTISVDTSRNQFSLNLSSVTAADTAVYYCTREDSSS WRSRGQGTLVTVSS | 65 |
| 335220 | QLQLQESGPGLVKPSETLSLTCTVSGGSISSSSYYWGWIRQPPGKGLEWIGS IYYSGSTYYNPSLKNRVTISVDTSKNQFSLKLSSVTAADTAVYYCTREDSS NWRSRGQGTLVTVSS | 66 |
| 335173 | QLQLQESGPGLVKPSETLSLTCTVSGGSITSSSYYWGWIRQPPGKGLEWIGS IYYSGSTYYNPSLKSRVTISVDTSKNQFSLKLSSVTAADTAVYYCTRDDSSN WRSRGQGTLVTVSS | 67 |
| 335219 | QLQLQESGPGLVKPSETLSLTCTVSGGSISSSSYYWGWIRQPPGKGLEWIGS IYYSGVTYYNPSLKNRVTISVDTSKNQFSLKLSSVTAADTAVYYCTREDSS NWRSRGQGTLVTVSS | 68 |
| 335236 | QLQLQESGPGLVKPSETLSLTCTVSGGSISSSSYYWGWIRQPPGKGLEWIGS IYYSGSTYYNPSLKSRVTISVDTSKNQFSLKLSSVTAADTAVYYCTREDSSN WRSRGQGTLVTVSS | 69 |
| 335266 | QLQLQESGPGLVRPSETLSLTCTVSGGSISSSSYYWGWIRQPPGKGLEWIGS IYYSGSTYYNPSLKSRVTISVDTSKNQFSLKLSSVTAADTAVYYCTREDSSS WRSRGQGTLVTVSS | 70 |
| 335208 | QLQLQESGPGLVKPSETLSLTCTVSGGSISSSSYYWGWIRQPPGKGLEWIGS IYYSGATYYNPSLKNRVTISVDTSRNQFSLNLSSVTAADTAVYYCTREDSS NWRSRGQGTLVTVSS | 71 |
| 335195 | QLQLQESGPGLVKPSETLSLTCTVSGGSISSSSYYWGWIRQPPGKGLEWIGS IYYSGATYYNPSLKNRVTISVDTSRNQFSLNLSSVTAADTAMYYCTREDSS NWRSRGQGTLVTVSS | 72 |
| 335285 | QLQLQESGPGLVKPSETLSLTCTVSGGSISSSSYYWGWIRQPPGKGLEWIGS IYYSGVTYYNPSLKNRVTISVDTSKNQFSLKLSSVTAADTAVYYCTREDSS SWRSRGQGTLVTVSS | 73 |
| 335150 | QLQLQESGPGLVKPSETLSLTCTVSGDSISSGDYYWGWIRQSPEKGLEWIG HIYYSGVTYYNPSLKNRVTISVDTSKNQFSLKLSSVTAADTAVYYCKRDDS SNWRSRGQGTLVTVSS | 74 |
| 335316 | QLQLQESGPGLVKPSETLSLTCTVSGGSISSSSYYWGWIRQPPGKGLEWIGH IYYSGATYYNPSLKNRVTISVDTSKNQFSLKLSSVTAADTAVYYCTREDSS SWRSRGQGTLVTVSS | 75 |
| 335189 | QLQLQESGPGLVKPSETLSLTCTVSGGSISSSSYYWGWIRQPPGKGLEWIGS VYYTGATYYNPSLKNRVTISVDTSKNQFSLKLSSVTAADTAVYYCTRDDS SNWRSRGQGTLVTVSS | 76 |
| 335179 | QLQLQESGPGLVKPSETLSLTCTVSGGSISSSSYYWGWFRHPPGKGLDWIG SIHYSGSTYYNPSLKSRVTISVDTSRNQFSLNLSSVTAADTAVYYCTRDDSS NWRSRGQGTLVTVSS | 77 |
| 335230 | QLQLQESDPGLVKPSETLSLTCTVSGGSISSS SHYWGWIRQPPGKGLEWIGH IYYSGATYYNPSLKNRVTISVDTSRNQFSLNLSSVTAADTAVYYCTREDSS NWRSRGQGTLVTVSS | 78 |
| 335166 | QLQLQESGPGLVKPSETLSLTCTVSGGSISSSSYYWGWIRQPPGKGLEWIGS IYYSGSTYYNP SLKNRVTISVDTSRNQFSLNLSSVTAADTAVYYCTRDDSS NWRSRGQGTLVTVSS | 79 |
| 335242 | QLQLQESGPGLVKPSETLSLTCTVSGGSISSSSYYWGWIRQPPGKGLEWIGH IYYSGATYYNPSLKNRVTISVDTSRNQFSLNLSSVTAADTAVYYCTREDSS NWRSRGQGTLVTVSS | 80 |
| 335162 | QLQLQESGPGLVKPSETLSLTCTVSGGSIISSSYYWGWIRQPPGKGLEWIGSI YYSGS AYYHPSLKSRVTISIDTSKNQFSLKLSSVTAADTAVYYCARDDSSN WRSRGQGTLVTVSS | 81 |

TABLE 2-continued

Anti-CD22 heavy chain antibody variable domain amino acid sequences.

| Clone ID # | SEQ_aa_FR1_FR4 | SEQ ID NO: |
|---|---|---|
| 335171 | QLQLQESGPGLVKPSETLSLTCTVSGGSISSSSYYWGWIRQPPGKGLEWIGS IYYSGATYYNPSLKNRVTISVDTSRNQFSLNLSSVTAADTAVYYCTRDDSS NWRSRGQGTLVTVSS | 82 |
| 335232 | QLQLQESGPGLVKPSETLSLTCTVSGDSISSGDYYWGWIRQPPGKGLEWIG HIYYSGATYYNPSLKNRVTISVDTSRNQSSLNLSSVTAADTAVYYCTREDS SNWRSRGQGTLVTVSS | 83 |
| 335263 | QLQLQESGPGLVKPSETLSLTCTVSGGSINDNSHYWGWIRQPPGKGLEWIG HIYYSGATYYNPSLKNRVTISVDTSRNQFSLNLSSVTAADTAVYYCTREDS SSWRSRGQGTLVTVSS | 84 |

Figure 14A:
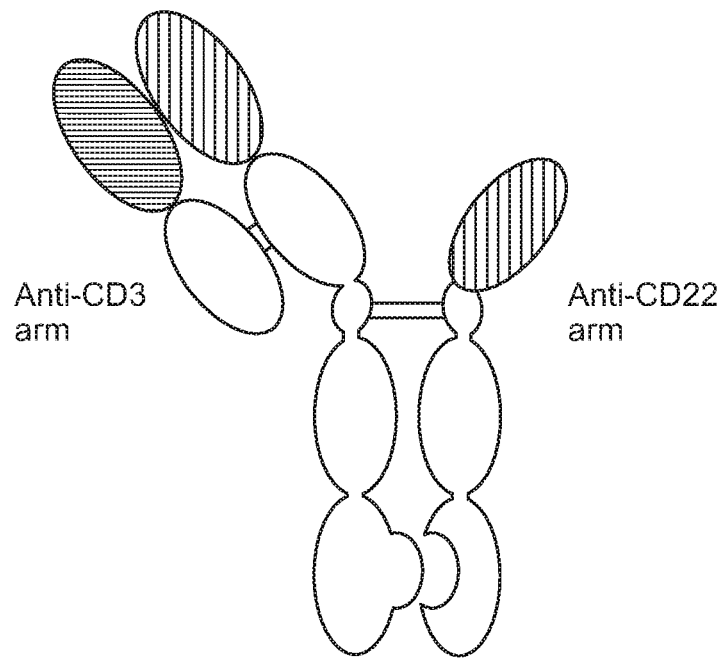
FIG. 14A is a schematic illustration of a bispecific binding compound having one binding unit that specifically binds to CD3 and one binding unit the specifically binds to CD22.
Figure 14B:
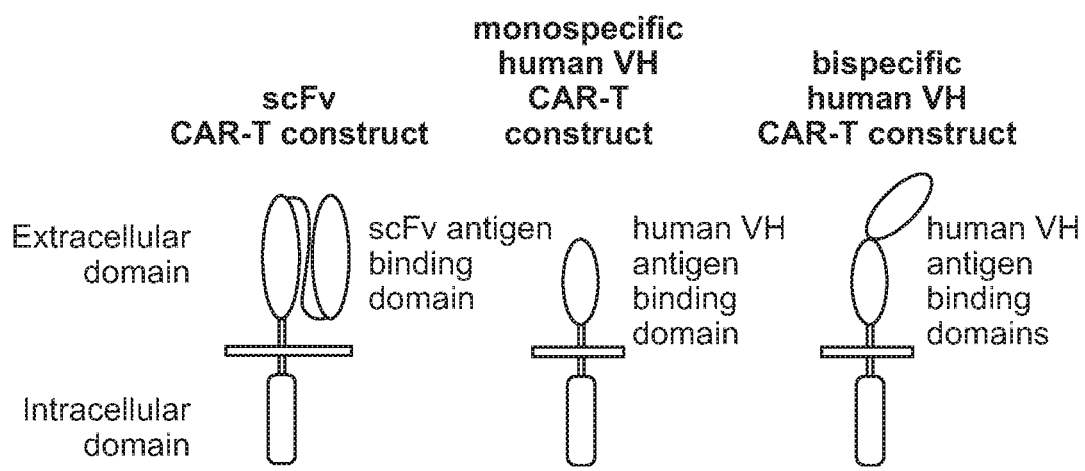
FIG. 14B is an illustration of various CAR-T constructs that can incorporate one or more binding domains in accordance with embodiments of the present invention.

A suitable antibody may be selected from those provided herein for development and therapeutic or other use, including, without limitation, use as a bispecific antibody, e.g., as shown in FIG. 14A, or a tri-specific antibody, or part of a CAR-T structure (e.g., as shown in FIG. 14B). FIG. 14A is an illustration of a non-limiting example of an anti-CD3× anti-CD22 multi-specific antibody, where the anti-CD22 domain is monovalent and monospecific. In some embodiments, the anti-CD3 domain contains a CH1 domain and pairs with a light chain, while the anti-CD22 domain(s) is derived from heavy chain-only antibodies and does not contain a CH1 domain or interact with a light chain. In some embodiments, the two heavy chains are pared using, e.g., knobs-into-holes technology.

Figure 15A:
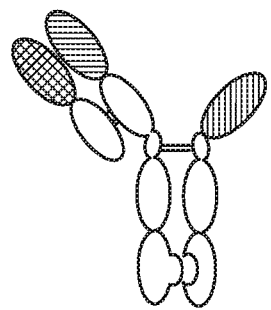
FIG. 15A is a schematic illustration of a bispecific binding molecule having one binding unit that specifically binds to CD3 and one binding unit the specifically binds to CD22 (monovalent, monospecific for CD22).
Figure 15B:
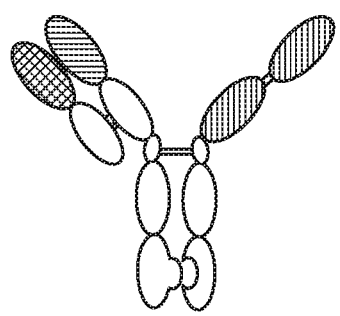
FIG. 15B is a schematic illustration of a bispecific binding molecule having one binding unit that specifically binds to CD3 and two binding units that specifically bind to CD22 (bivalent, monospecific for CD22).
Figure 15C:
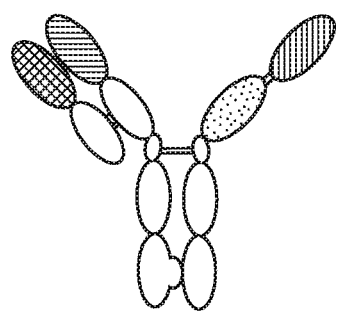
FIG. 15C is a schematic illustration of a bispecific binding molecule having one binding unit that specifically binds to CD3 and two binding units that specifically bind to CD22 (bivalent, biparatopic for CD22).

Turning to the antibodies depicted in FIG. 15, FIG. 15A depicts an anti-CD3× anti-CD22 bispecific antibody wherein the anti-CD22 binding arm is monovalent and monospecific, and the antigen-binding domain of the anti-CD22 arm is in a single configuration, meaning only one antigen-binding domain is present. FIG. 15B depicts an anti-CD3× anti-CD22 bispecific antibody wherein the anti-CD22 binding arm is bivalent and monospecific, and the antigen-binding domain of the anti-CD22 arm is in a tandem configuration, meaning there are two identical antigen binding domains placed in tandem. FIG. 15C depicts an anti-CD3× anti-CD22 bispecific antibody wherein the anti-CD22 binding arm is bivalent and biparatopic, and the antigen-binding domains of the anti-CD22 arm are in a tandem configuration.

Determination of affinity for a candidate protein can be performed using methods known in the art, such as Biacore measurements. Members of the antibody family may have an affinity for CD22 with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a CD22 biological activity, including in vitro assays, pre-clinical models, and clinical trials, as well as assessment of potential toxicity.

Members of the antibody family herein are not cross-reactive with the CD22 protein of Cynomolgus macaque, but can be engineered to provide cross-reactivity with the CD22 protein of Cynomolgus macaque, or with the CD22 of any other animal species, if desired.

The family of CD22-specific antibodies herein comprises a VH domain, comprising CDR1, CDR2 and CDR3 sequences in a human VH framework. The CDR sequences may be situated, as an example, in the region of around amino acid residues 26-35; 53-59; and 98-117 for CDR1, CDR2 and CDR3, respectively, of the provided exemplary variable region sequences set forth in SEQ ID NOs: 24 to 84. It will be understood by one of ordinary skill in the art that the CDR sequences may be in different positions if a different framework sequence is selected, although generally the order of the sequences will remain the same.

The CDR1, CDR2, and CDR3 sequences of the anti-CD22 antibodies of the present invention may be encompassed by the following structural formulas, where an X indicates a variable amino acid, which may be specific amino acids as indicated below.

CDR1 (SEQ ID NO: 104)

G $X_1$ S I $X_2$ $X_3$ $X_4$ $X_5$ $X_6$ Y where $X_1$ is D or G;
$X_2$ is S, T, I or N;
$X_3$ is S or D;
$X_4$ is G, S or N;
$X_5$ is D, G or S; and
$X_6$ is Y or H.

CDR2 (SEQ ID NO: 105)

$X_7$ $X_8$ Y $X_9$ G $X_{10}$ $X_{11}$ where $X_7$ is I or V;
$X_8$ is Y or H;
$X_9$ is S or T;
$X_{10}$ is A, V or S; and
$X_{11}$ is T or A.

CDR3 (SEQ ID NO: 106)

$X_{12}$ R $X_{13}$ D S S $X_{14}$ W R S where $X_{12}$ is T, A or K;
$X_{13}$ is D or E; and
$X_{14}$ is N or S.

Representative CDR1, CDR2 and CDR3 sequences are shown in Tables 1 and 3.

TABLE 3

Anti-CD22 heavy chain antibody CDR1, CDR2 and CDR3 amino acid sequences.

| Clone ID # | SEQ_aa_CDR1 | SEQ_aa_CDR2 | SEQ_aaCDR3 |
|---|---|---|---|
| 335207 | GDSISSGDYY (SEQ ID NO: 1) | IYYSGVT (SEQ ID NO: 11) | TREDSSNWRS (SEQ ID NO: 18) |
| 335161 | GDSISSGDYY (SEQ ID NO: 1) | IYYSGAT (SEQ ID NO: 12) | TRDDSSNWRS (SEQ ID NO: 19) |
| 335254 | GDSISSGDYY (SEQ ID NO: 1) | IYYSGVT (SEQ ID NO: 11) | TREDSSSWRS (SEQ ID NO: 20) |
| 335260 | GDSISSGDYY (SEQ ID NO: 1) | IYYSGVT (SEQ ID NO: 11) | TREDSSSWRS (SEQ ID NO: 20) |
| 335151 | GDSISSGDYY (SEQ ID NO: 1) | IYYSGAT (SEQ ID NO: 12) | TRDDSSNWRS (SEQ ID NO: 19) |
| 335170 | GDSISSGDYY (SEQ ID NO: 1) | IYYSGAT (SEQ ID NO: 12) | TRDDSSNWRS (SEQ ID NO: 19) |
| 335176 | GDSISSGDYY (SEQ ID NO: 1) | IYYSGAT (SEQ ID NO: 12) | TRDDSSNWRS (SEQ ID NO: 19) |
| 335181 | GDSISSGGYY (SEQ ID NO: 2) | IYYSGAT (SEQ ID NO: 12) | TRDDSSNWRS (SEQ ID NO: 19) |
| 335244 | GDSISSGDYY (SEQ ID NO: 1) | IYYSGAT (SEQ ID NO: 12) | TREDSSSWRS (SEQ ID NO: 20) |
| 335154 | GDSISSGDYY (SEQ ID NO: 1) | IYYSGVT (SEQ ID NO: 11) | TRDDSSNWRS (SEQ ID NO: 19) |
| 335201 | GDSISSGDYY (SEQ ID NO: 1) | IYYSGVT (SEQ ID NO: 11) | TREDSSNWRS (SEQ ID NO: 18) |
| 335261 | GDSISSGDYY (SEQ ID NO: 1) | IYYSGAT (SEQ ID NO: 12) | TREDSSSWRS (SEQ ID NO: 20) |
| 335293 | GDSISSGDYY (SEQ ID NO: 1) | IYYSGAT (SEQ ID NO: 12) | TREDSSSWRS (SEQ ID NO: 20) |
| 335203 | GDSISSGDYY (SEQ ID NO: 1) | IYYSGVT (SEQ ID NO: 11) | TREDSSNWRS (SEQ ID NO: 18) |
| 335185 | GDSISSGDYY (SEQ ID NO: 1) | IYYSGAT (SEQ ID NO: 12) | TREDSSNWRS (SEQ ID NO: 18) |
| 335206 | GDSISSGDYY (SEQ ID NO: 1) | IYYSGAT (SEQ ID NO: 12) | TREDSSNWRS (SEQ ID NO: 18) |
| 335245 | GDSISSGDYY (SEQ ID NO: 1) | IYYSGAT (SEQ ID NO: 12) | TREDSSSWRS (SEQ ID NO: 20) |
| 335218 | GDSISSGDYY (SEQ ID NO: 1) | IYYSGAT (SEQ ID NO: 12) | TREDSSNWRS (SEQ ID NO: 18) |
| 335160 | GDSISSGDYY (SEQ ID NO: 1) | IYYSGAT (SEQ ID NO: 12) | TRDDSSNWRS (SEQ ID NO: 19) |
| 335158 | GGSISSGDYY (SEQ ID NO: 3) | IYYSGAT (SEQ ID NO: 12) | TRDDSSNWRS (SEQ ID NO: 19) |
| 324508 | GGSISSGDYY (SEQ ID NO: 3) | IYYSGAT (SEQ ID NO: 12) | TRDDSSNWRS (SEQ ID NO: 19) |
| 335307 | GDSISSGDYY (SEQ ID NO: 1) | IYYSGST (SEQ ID NO: 13) | TREDSSSWRS (SEQ ID NO: 20) |
| 335301 | GDSISSGDYY (SEQ ID NO: 1) | IYYSGAT (SEQ ID NO: 12) | TREDSSSWRS (SEQ ID NO: 20) |
| 335323 | GDSISSGGYY (SEQ ID NO: 2) | IYYSGST (SEQ ID NO: 13) | TREDSSSWRS (SEQ ID NO: 20) |
| 335271 | GDSISSGDYY (SEQ ID NO: 1) | IYYSGAT (SEQ ID NO: 12) | TREDSSSWRS (SEQ ID NO: 20) |

TABLE 3-continued

Anti-CD22 heavy chain antibody CDR1, CDR2 and CDR3 amino acid sequences.

| Clone ID # | SEQ_aa_CDR1 | SEQ_aa_CDR2 | SEQ_aaCDR3 |
|---|---|---|---|
| 335234 | GDSISSGDYY (SEQ ID NO: 1) | IYYSGAT (SEQ ID NO: 12) | TREDSSNWRS (SEQ ID NO: 18) |
| 335182 | GDSISSGDYY (SEQ ID NO: 1) | IYYSGAT (SEQ ID NO: 12) | TRDDSSNWRS (SEQ ID NO: 19) |
| 335186 | GGSISSSSYY (SEQ ID NO: 4) | IYYSGST (SEQ ID NO: 13) | TRDDSSNWRS (SEQ ID NO: 19) |
| 335233 | GDSISSGDYY (SEQ ID NO: 1) | IYYSGST (SEQ ID NO: 13) | TREDSSNWRS (SEQ ID NO: 18) |
| 335224 | GDSISSGDYY (SEQ ID NO: 1) | IYYTGST (SEQ ID NO: 14) | TREDSSNWRS (SEQ ID NO: 18) |
| 335210 | GGSISSGDYY (SEQ ID NO: 3) | IYYSGAT (SEQ ID NO: 12) | TREDSSNWRS (SEQ ID NO: 18) |
| 335311 | GGSFSGYY (SEQ ID NO: 5) | IYYSGAT (SEQ ID NO: 12) | TREDSSSWRS (SEQ ID NO: 20) |
| 335159 | GGSISSSSYY (SEQ ID NO: 4) | IYYSGVT (SEQ ID NO: 11) | TRDDSSNWRS (SEQ ID NO: 19) |
| 335188 | GGSISSSSYY (SEQ ID NO: 4) | IYYSGVT (SEQ ID NO: 11) | TRDDSSNWRS (SEQ ID NO: 19) |
| 335274 | GGSISSSSYY (SEQ ID NO: 4) | IYYSGST (SEQ ID NO: 13) | TREDSSSWRS (SEQ ID NO: 20) |
| 335226 | GDSISSSSYY (SEQ ID NO: 6) | IYYSGST (SEQ ID NO: 13) | TREDSSNWRS (SEQ ID NO: 18) |
| 335333 | GGSISSSSYY (SEQ ID NO: 4) | IYYSGST (SEQ ID NO: 13) | AREDSSSWRS (SEQ ID NO: 21) |
| 335283 | GGSISSSSYY (SEQ ID NO: 4) | IYYSGAT (SEQ ID NO: 12) | TREDSSSWRS (SEQ ID NO: 20) |
| 335297 | GGSISSSSYY (SEQ ID NO: 4) | IYYSGAT (SEQ ID NO: 12) | TREDSSSWRS (SEQ ID NO: 20) |
| 335273 | GGSISSSSYY (SEQ ID NO: 4) | IYYSGST (SEQ ID NO: 13) | TREDSSSWRS (SEQ ID NO: 20) |
| 335187 | GGSISSSSYY (SEQ ID NO: 4) | IYYSGAT (SEQ ID NO: 12) | TRDDSSNWRS (SEQ ID NO: 19) |
| 335295 | GGSISSSSYY (SEQ ID NO: 4) | IYYSGAT (SEQ ID NO: 12) | TREDSSSWRS (SEQ ID NO: 20) |
| 335220 | GGSISSSSYY (SEQ ID NO: 4) | IYYSGST (SEQ ID NO: 13) | TREDSSNWRS (SEQ ID NO: 18) |
| 335173 | GGSITSSSYY (SEQ ID NO: 7) | IYYSGST (SEQ ID NO: 13) | TRDDSSNWRS (SEQ ID NO: 19) |
| 335219 | GGSISSSSYY (SEQ ID NO: 4) | IYYSGVT (SEQ ID NO: 11) | TREDSSNWRS (SEQ ID NO: 18) |
| 335236 | GGSISSSSYY (SEQ ID NO: 4) | IYYSGST (SEQ ID NO: 13) | TREDSSNWRS (SEQ ID NO: 18) |
| 335266 | GGSISSSSYY (SEQ ID NO: 4) | IYYSGST (SEQ ID NO: 13) | TREDSSSWRS (SEQ ID NO: 20) |
| 335208 | GGSISSSSYY (SEQ ID NO: 4) | IYYSGAT (SEQ ID NO: 12) | TREDSSNWRS (SEQ ID NO: 18) |
| 335195 | GGSISSSSYY (SEQ ID NO: 4) | IYYSGAT (SEQ ID NO: 12) | TREDSSNWRS (SEQ ID NO: 18) |
| 335285 | GGSISSSSYY (SEQ ID NO: 4) | IYYSGVT (SEQ ID NO: 11) | TREDSSSWRS (SEQ ID NO: 20) |

TABLE 3-continued

Anti-CD22 heavy chain antibody CDR1, CDR2 and CDR3 amino acid sequences.

| Clone ID # | SEQ_aa_CDR1 | SEQ_aa_CDR2 | SEQ_aaCDR3 |
|---|---|---|---|
| 335150 | GDSISSGDYY (SEQ ID NO: 1) | IYYSGVT (SEQ ID NO: 11) | KRDDSSNWRS (SEQ ID NO: 22) |
| 335316 | GGSISSSSYY (SEQ ID NO: 4) | IYYSGAT (SEQ ID NO: 12) | TREDSSSWRS (SEQ ID NO: 20) |
| 335189 | GGSISSSSYY (SEQ ID NO: 4) | VYYTGAT (SEQ ID NO: 15) | TRDDSSNWRS (SEQ ID NO: 19) |
| 335179 | GGSISSSSYY (SEQ ID NO: 4) | IHYSGST (SEQ ID NO: 16) | TRDDSSNWRS (SEQ ID NO: 19) |
| 335230 | GGSISSSSHY (SEQ ID NO: 8) | IYYSGAT (SEQ ID NO: 12) | TREDSSNWRS (SEQ ID NO: 18) |
| 335166 | GGSISSSSYY (SEQ ID NO: 4) | IYYSGST (SEQ ID NO: 13) | TRDDSSNWRS (SEQ ID NO: 19) |
| 335242 | GGSISSSSYY (SEQ ID NO: 4) | IYYSGAT (SEQ ID NO: 12) | TREDSSNWRS (SEQ ID NO: 18) |
| 335162 | GGSIISSSYY (SEQ ID NO: 9) | IYYSGSA (SEQ ID NO: 17) | ARDDSSNWRS (SEQ ID NO: 23) |
| 335171 | GGSISSSSYY (SEQ ID NO: 4) | IYYSGAT (SEQ ID NO: 12) | TRDDSSNWRS (SEQ ID NO: 19) |
| 335232 | GDSISSGDYY (SEQ ID NO: 1) | IYYSGAT (SEQ ID NO: 12) | TREDSSNWRS (SEQ ID NO: 18) |
| 335263 | GGSINDNSHY (SEQ ID NO: 10) | IYYSGAT (SEQ ID NO: 12) | TREDSSSWRS (SEQ ID NO: 20) |

In some embodiments, an anti-CD22 heavy chain-only antibody of the invention comprises a CDR1 sequence of any one of SEQ ID NOs: 1-10. In a particular embodiment, the CDR1 sequence is SEQ ID NO: 1.

In some embodiments, an anti-CD22 heavy chain-only antibody of the invention comprises a CDR2 sequence of any one of SEQ ID NOs: 11-17. In a particular embodiment, the CDR2 sequence is SEQ ID NO: 11.

In some embodiments, an anti-CD22 heavy chain-only antibody of the invention comprises a CDR3 sequence of any one of SEQ ID NOs: 18-23. In a particular embodiment, the CDR2 sequence is SEQ ID NO: 18.

In a further embodiment, an anti-CD22 heavy chain-only antibody of the invention comprises the CDR1 sequence of SEQ ID NO:1; the CDR2 sequence of SEQ ID NO: 11; and the CDR3 sequence of SEQ ID NO: 18.

In further embodiments, an anti-CD22 heavy chain-only antibody of the invention comprises any of the heavy chain variable region amino acid sequences of SEQ ID NOs: 24 to 84 (Table 2).

In a still further embodiment, an anti-CD22 heavy chain-only antibody of the present invention comprises the heavy chain variable region sequence of SEQ ID NO: 24.

Figure 1B:
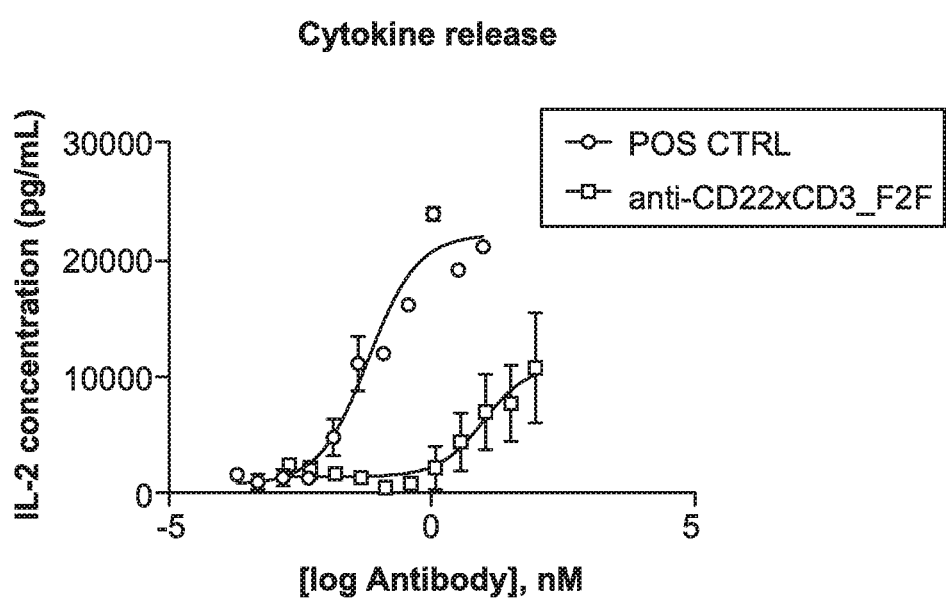
FIG. 1B is a graph depicting dose response curves of cytokine release by resting human pan T cells incubated with CD22 positive cells (Daudi) and treated with an anti-CD22xCD3_F2F multispecific binding compound and a positive control.

In some embodiments, a CDR sequence in an anti-CD22 heavy chain-only antibody of the invention comprises one or two amino acid substitutions relative to a CDR1, CDR2 and/or CDR3 sequence or set of CDR1, CDR2 and CDR3 sequences in any one of SEQ ID NOs:1 to 23 (FIG. 1). In some embodiments, said amino acid substitution(s) are one or two of amino acid positions 4-6 of CDR1, and/or one or two of the amino acid positions of 2, 4-7 of CDR2, and/or one or two of the amino acid positions 5 and 12 of CDR3, relative to the formulas provided above. In some embodiments, the heavy chain-only anti-CD22 antibodies herein can comprise a heavy chain variable region sequence with at least about 85% identity, at least 90% identity, at least 95% identity, at least 98% identify, or at least 99% identity to any one of the heavy chain variable region sequences of SEQ ID NOs: 24 to 84 (shown in Table 2).

In some embodiments, bispecific or multi-specific antibodies are provided, which may have any of the configurations discussed herein, including, without limitation, a bispecific three-chain antibody like molecule. In some embodiments, a multi-specific antibody can comprise at least one heavy chain variable region having binding specificity for CD22. In some embodiments, a multi-specific antibody can comprise a heavy chain variable region comprising at least two antigen-binding domains, wherein each of the antigen-binding domains has binding specificity for CD22. In some embodiments, a multi-specific antibody can comprise a heavy chain/light chain pair that has binding specificity for a first antigen (e.g., CD3), and a heavy chain from a heavy chain-only antibody. In certain embodiments, the heavy chain from the heavy chain only antibody comprises an Fc portion comprising CH2 and/or CH3 and/or CH4 domains, in the absence of a CH1 domain. In one particular embodiment, a bispecific antibody comprises a heavy chain/light chain pair that has binding specificity for an antigen on an effector cell (e.g., a CD3 protein on a T cell), and a heavy chain from a heavy chain-only antibody comprising an antigen-binding domain that has binding specificity for CD22.

In some embodiments, a multi-specific antibody comprises a CD3-binding VH domain that is paired with a light chain variable domain. In certain embodiments, the light chain is a fixed light chain. In some embodiments, the CD3-binding VH domain comprises a CDR1 sequence of SEQ ID NO: 85, a CDR2 sequence of SEQ ID NO: 86, and a CDR3 sequence of SEQ ID NO: 87, in a human VH framework. In some embodiments, the fixed light chain comprises a CDR1 sequence of SEQ ID NO: 88, a CDR2 sequence of SEQ ID NO: 89, and a CDR3 sequence of SEQ ID NO: 90, in a human VL framework. Together, the CD3-binding VH domain and the light chain variable domain have binding affinity for CD3. In some embodiments, a CD3-binding VH domain comprises a heavy chain variable region sequence of SEQ ID NO: 91. In some embodiments, a CD3-binding VH domain comprises a sequence having at least about 80%, at least about 85%, at least about 90%, at least about 95%, or at least about 99% percent identity to the heavy chain variable region sequence of SEQ ID NO: 91. In some embodiments, a fixed light chain comprises a light chain variable region sequence of SEQ ID NO: 92. In some embodiments, a fixed light chain comprises a sequence having at least about 80%, at least about 85%, at least about 90%, at least about 95%, or at least about 99% percent identity to the heavy chain variable region sequence of SEQ ID NO: 92.

Multi-specific antibodies comprising the above-described CD3-binding $V_H$ domain and light chain variable domain have advantageous properties, for example, as described in published PCT application publication number WO2018/052503, the disclosure of which is incorporated by reference herein in its entirety. Any of the multi-specific antibodies and antigen-binding domains described herein, having binding affinity to CD22, can be combined with the CD3-binding domains and fixed light chain domains described herein to generate multi-specific antibodies having binding affinity to one or more CD22 epitopes as well as CD3.

TABLE 4

Anti-CD3 Heavy and Light Chain CDR1, CDR2, CDR3 amino acid sequences.

| | SEQ_aa_CDR1 | SEQ_aa_CDR2 | SEQ_aa_CDR3 |
| --- | --- | --- | --- |
| Heavy Chain | GFTFHNYA (SEQ ID NO: 85) | ISWNSGSI (SEQ ID NO: 86) | AKDSRGYGDYS LGGAY (SEQ ID NO: 87) |
| Light Chain | QSVSSN (SEQ ID NO: 88) | GAS (SEQ ID NO: 89) | QQYNNWPWT (SEQ ID NO: 90) |

TABLE 5

Anti-CD3 heavy and light chain variable region amino acid sequences.

| | |
| --- | --- |
| VH | EVQLVESGGGLVQPGRSLRLSCAASGFTFHNYAMHWVRQAPGK GLEWVSGISWNSGSIGYADSVKGRFTISRDNAKNSLYLQMNSL RAEDTALYYCAKDSRGYGDYSLGGAYWGQGTLVTVSS (SEQ ID NO: 91) |
| VL | EIVMTQSPATLSVSPGERATLSCRASQSVSSNLAWYQQKPGQA PRLLIYGASTRATGIPARFSGSGSGTEFTLTISSLQSEDFAVY YCQQYNNWPWTFGQGTKVEIK (SEQ ID NO: 92) |

TABLE 6

Human IgG1 and IgG4 Fc region sequences.

| | |
| --- | --- |
| Human IgG1 (UniProt. No. P01857) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGK (SEQ ID NO: 93) |
| Human IgG4 (UniProt No. P01861) | ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPSCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK (SEQ ID NO: 94) |
| Human IgG1 with silencing mutation (Fc region) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK (SEQ ID NO: 95) |
| Human IgG4 with mutation silencing (Fc region) | ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPPCPAPEAAGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK (SEQ ID NO: 96) |

TABLE 7 additional sequences.

| | |
| --- | --- |
| Anti-CD3 light chain constant region sequence (kappa light chain) | EIVMTQSPATLSVSPGERATLSCRASQSVSSNLAWYQQKPGQAPRLLI YGASTRATGIPARFSGSGSGTEFTLTISSLQSEDFAVYYCQQYNNWPW TFGQGTKVEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC (SEQ ID NO: 97) |
| Anti-CD3 heavy chain sequence (with wt IgG1 Fc) | EVQLVESGGGLVQPGRSLRLSCAASGFTFHNYAMHWVRQAPGKGLE WVSGISWNSGSIGYADSVKGRFTISRDNAKNSLYLQMNSLRAEDTAL YYCAKDSRGYGDYSLGGAYWGQGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNW YVDGVEVHNAKTKPREEQYNSTYRVVSVLTVLHQDWLNGKEYKCK |

TABLE 7-continued additional sequences.

| | |
|---|---|
| | VSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGK (SEQ ID NO: 98) |
| Anti-CD3 heavy<br>chain constant<br>region sequence<br>(with silenced IgG1<br>Fc) | EVQLVESGGGLVQPGRSLRLSCAASGFTFHNYAMHWVRQAPGKGLE<br>WVSGISWNSGSIGYADSVKGRFTISRDNAKNSLYLQMNSLRAEDTAL<br>YYCAKDSRGYGDYSLGGAYWGQGTLVTVSSASTKGPSVFPLAPSSKS<br>TSGGTAALGCLVKDYFPEPVTVSWNSGALTSGVHTFPAVLQSSGLYS<br>LSSVVTVPSSSLGTQTYICNVNHKPSNTKVDKKVEPKSCDKTHTCPPC<br>PAPEAAGGPSVFLFPPKPKDTLMISRTPEVTCVVVDVSHEDPEVKFNW<br>YVDGVEVHNAKTKPREEQYNSTYRVVSVLTVLHQDWLNGKEYKCK<br>VSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRW<br>QQGNVFSCSVMHEALHNHYTQKSLSLSPGK (SEQ ID NO: 99) |
| Anti-CD3 heavy<br>chain constant<br>region sequence<br>(with wt IgG4 Fc) | EVQLVESGGGLVQPGRSLRLSCAASGFTFHNYAMHWVRQAPGKGLE<br>WVSGISWNSGSIGYADSVKGRFTISRDNAKNSLYLQMNSLRAEDTAL<br>YYCAKDSRGYGDYSLGGAYWGQGTLVTVSSASTKGPSVFPLAPCSRS<br>TSESTAALGCLVKDYFPEPVTVSWNSGALTSGVHTFPAVLQSSGLYSL<br>SSVVTVPSSSLGTKTYTCNVDHKPSNTKVDKRVESKYGPPCPSCPAPE<br>FLGGPSVFLFPPKPKDTLMISRTPEVTCVVVDVSQEDPEVQFNWYVDG<br>VEVHNAKTKPREEQFNSTYRVVSVLTVLHQDWLNGKEYKCKVSNKG<br>LPSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVF<br>SCSVMHEALHNHYTQKSLSLSLGK (SEQ ID NO: 100) |
| Anti-CD3 heavy<br>chain constant<br>region sequence<br>(with silenced IgG4<br>Fc) | EVQLVESGGGLVQPGRSLRLSCAASGFTFHNYAMHWVRQAPGKGLE<br>WVSGISWNSGSIGYADSVKGRFTISRDNAKNSLYLQMNSLRAEDTAL<br>YYCAKDSRGYGDYSLGGAYWGQGTLVTVSSASTKGPSVFPLAPCSRS<br>TSESTAALGCLVKDYFPEPVTVSWNSGALTSGVHTFPAVLQSSGLYSL<br>SSVVTVPSSSLGTKTYTCNVDHKPSNTKVDKRVESKYGPPCPPCPAPE<br>AAGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNK<br>GLPSSIEKTISKAKGQPREPQVYTLPPSQEEMTKNQVSLTCLVKGFYPS<br>DIAVEWESNGQPENNYKTTPPVLDSDGSFFLYSRLTVDKSRWQEGNV<br>FSCSVMHEALHNHYTQKSLSLSLGK (SEQ ID NO: 101) |

In some embodiments, bispecific or multi-specific antibodies are provided, which may have any of the configurations discussed herein, including, without limitation, a bispecific three-chain antibody like molecule. In some embodiments, a bispecific antibody can comprise at least one heavy chain variable region having binding specificity for CD22, and at least one heavy chain variable region having binding specificity for a protein other than CD22. In some embodiments, a bispecific antibody can comprise a heavy chain/light chain pair that has binding specificity for a first antigen, and a heavy chain from a heavy chain-only antibody, comprising an Fc portion comprising CH2 and/or CH3 and/or CH4 domains, in the absence of a CH1 domain, and an antigen binding domain that binds an epitope of a second antigen or a different epitope of the first antigen. In one particular embodiment, a bispecific antibody comprises a heavy chain/light chain pair that has binding specificity for an antigen on an effector cell (e.g., a CD3 protein on a T cell), and a heavy chain from a heavy chain-only antibody comprising an antigen-binding domain that has binding specificity for CD22.

In some embodiments, where a binding compound of the invention is a bispecific antibody, one arm of the antibody (one binding moiety, or one binding unit) is specific for human CD22, while the other arm may be specific for target cells, tumor-associated antigens, targeting antigens, e.g., integrins, etc., pathogen antigens, checkpoint proteins, and the like. Target cells specifically include cancer cells, including, without limitation, cells from hematologic tumors, e.g. B-cell tumors, as discussed below. In some embodiments, one arm of the antibody (one binding moiety, or one binding unit) is specific for human CD22, while the other arm is specific for CD3.

In some embodiments, a binding compound comprises an anti-CD3 light chain polypeptide comprising the sequence of SEQ ID NO: 92 linked to the sequence of SEQ ID NO: 97, an anti-CD3 heavy chain polypeptide comprising the sequence of any one of SEQ ID NOs: 98, 99, 100 or 101, and an anti-CD22 heavy chain polypeptide comprising the sequence of any one of SEQ ID NOs: 24-84 linked to the sequence of any one of SEQ ID NOs: 93, 94, 95 or 96. These sequences can be combined in various ways to produce a bispecific antibody of a desired IgG subclass, e.g., IgG1, IgG4, silenced IgG1, silenced IgG4.

Various formats of bispecific antibodies are within the ambit of the invention, including, without limitation, single chain polypeptides, two chain polypeptides, three chain polypeptides, four chain polypeptides, and multiples thereof. The multi-specific antibodies herein specifically include T cell multi-specific (e.g., bispecific) antibodies binding to CD22 (anti-CD22× anti-CD3 antibodies), which is selectively expressed on mature B-cells, and CD3. Such antibodies induce potent T cell mediated killing of cells expressing CD22.

Preparation of Antibodies

The multispecific binding compounds of the present invention can be prepared by methods known in the art. In a preferred embodiment, the heavy chain antibodies herein are produced by transgenic animals, including transgenic mice and rats, preferably rats, in which the endogenous immunoglobulin genes are knocked out or disabled. In a preferred embodiment, the heavy chain antibodies herein are produced in UniRat™. UniRat™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety of technologies, in UniRat™ the zinc-finger (endo)nuclease (ZNF) technology was used to inactivate the endogenous rat heavy chain J-locus, light chain Cκ locus and light chain a Cλ locus. ZNF constructs for microinjection into oocytes can produce IgH and IgL knock out (KO) lines. For details see, e.g., Geurts et al., 2009, Science 325:433. Characterization of Ig heavy chain knockout rats has been reported by Menoret et al., 2010, Eur. J. Immunol. 40:2932-2941. Advantages of the ZNF technology are that non-homologous end joining to silence a gene or locus via deletions up to several kb can also provide a target site for homologous integration (Cui et al., 2011, Nat Biotechnol 29:64-67). Human heavy chain antibodies produced in UniRat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, rat can also be used, rats and mice being preferred. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), *E. coli* or yeast.

Domains of heavy chain-only antibodies combine advantages of antibodies and small molecule drugs: can be mono- or multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost effective manner.

In a particular embodiment, the heavy chain antibodies of the present invention, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. The substituted amino acid residue preferably is charged, and more preferably is positively charged, such as lysine (Lys, K), arginine (Arg, R) or histidine (His, H), preferably arginine (R). In a preferred embodiment the heavy chain-only antibodies derived from the transgenic animals contain a Trp to Arg mutation at position 101. The resultant HCAbs preferably have high antigen-binding affinity and solubility under physiological conditions in the absence of aggregation.

As part of the present invention, human anti-CD22 heavy chain antibodies with unique sequences from UniRat™ animals (UniAb™) were identified that bind human CD22 in ELISA protein and cell-binding assays. The identified heavy chain variable region (VH) sequences (see, e.g., Table 2) are positive for human CD22 protein binding and/or for binding to CD22+ cells, and are all negative for binding to cells that do not express CD22.

Heavy chain antibodies binding to non-overlapping epitopes on a CD22 protein, e.g., UniAbs™ can be identified by competition binding assays, such as enzyme-linked immunoassays (ELISA assays) or flow cytometric competitive binding assays. For example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn XPR36 (BioRad, Inc), Biacore 2000 and Biacore T200 (GE Healthcare Life Sciences), and MX96 SPR imager (Ibis technologies B.V.), as well as on biolayer interferometry platforms, such as Octet Red384 and Octet HTX (ForteBio, Pall Inc). For further details see the examples herein.

Typically, an antibody "competes" with a reference antibody if it causes about 15-100% reduction in the binding of the reference antibody to the target antigen, as determined by standard techniques, such as by the competition binding assays described above. In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, at least about 95% or higher.

Pharmaceutical Compositions, Uses and Methods of Treatment

It is another aspect of the present invention to provide pharmaceutical compositions comprising one or more multispecific binding compounds of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

In one embodiment, a pharmaceutical composition comprises a heavy chain antibody (e.g., UniAb™) that binds to CD22. In another embodiment, a pharmaceutical composition comprises a multi-specific (including bispecific) heavy chain antibody (e.g., UniAb™) with binding specificity for two or more non-overlapping epitopes on a CD22 protein. In a preferred embodiment, a pharmaceutical composition comprises a multi-specific (including bispecific) heavy chain antibody (e.g., UniAb™) with binding specificity to CD22 and with binding specificity to a binding target on an effector cell (e.g., a binding target on a T cell, such as, e.g., a CD3 protein on a T cell).

Pharmaceutical compositions of the antibodies used in accordance with the present invention are prepared for storage by mixing proteins having the desired degree of purity with optional pharmaceutically acceptable carriers, excipients or stabilizers (see, e.g. Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Antibody formulations are disclosed, for example, in U.S. Pat. No. 9,034,324. Similar formulations can be used for the heavy chain antibodies, including UniAbs™, of the present invention. Subcutaneous antibody formulations are described, for example, in U520160355591 and US20160166689.

Methods of Use

The heavy chain-only anti-CD22 antibodies, multi-specific antibodies, and pharmaceutical compositions described herein can be used for the treatment of diseases and conditions characterized by the expression of CD22, including, without limitation, the conditions and diseases described further herein.

CD22 is a 135-kDa type I transmembrane protein that is expressed at low levels on pre- and immature B cells, maximally on mature B cells, and ultimately downregulated on plasma cells. (E.g., Walker et al., Immunology, 2008 March; 123(3) 314-25). CD22 is strongly expressed in follicular (primary and secondary B cell zones), mantle, and marginal zone B cells, and has been reported to be present in 60% to 80% of samples from patients with B cell malignancies (Alderson et al., Clin. Cancer Res 2009; 15(3) Feb. 11, 2009). Due to its observed expression in a number of hematological malignancies, CD22 is a promising target for antibody-based therapeutics.

In one aspect, the CD22 heavy chain antibodies (e.g., UniAbs™) and pharmaceutical compositions herein can be used to treat hematological malignancies characterized by the expression of CD22, including, without limitation, diffuse large B cell lymphoma (DLBCL), non-Hodgkin's lymphoma, B-cell chronic lymphocylic leukemia (CLL), and B-cell acute lymphoblastic leukemia (ALL).

Diffuse large B cell lymphoma (DLBCL or DLBL) is the most common form of non-Hodgkin's lymphoma among adults (Blood 1997 89 (11): 3909-18), with an estimated annual incidence of 7 to 8 cases per 100,000 people per year in the US and the UK. It is characterized as an aggressive cancer that can arise in virtually any part of the body. The causes of DLBCL are not well understood, and it can arise from normal B cells as well as malignant transformation of other types of lymphoma or leukemia cells. Treatment approaches generally involve chemotherapy and radiation, and have resulted in an overall five-year survival rate average of approximately 58% for adults. Although some monoclonal antibodies have shown promise for treating DLBCL, consistent clinical efficacy has not yet been conclusively demonstrated. There is therefore a great need for new therapies, including immunotherapies, for DLBCL.

In another aspect, the CD22 heavy chain antibodies (e.g., UniAbs™) and pharmaceutical compositions herein can be used to treat autoimmune disorders characterized by pathogenic B-cells that express CD22, including, without limitation, systemic lupus erythematosus (SLE), rheumatoid arthritis (RA), and multiple sclerosis (MS).

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other agent (e.g., another ablative agent) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g., a chemotherapeutic drug, etc. Kits typically include a label indicating the intended use of the contents of the kit. The term "label" as used herein includes any writing, or recorded material supplied on or with a kit, or which otherwise accompanies a kit.

The invention now being fully described, it will be apparent to one of ordinary skill in the art that various changes and modifications can be made without departing from the spirit or scope of the invention.

EXAMPLES

Materials and Methods
CD22 Protein Binding

The kinetic binding experiments to determine the antigen-antibody affinities were performed on the Octet QK-384 system (ForteBio) using bilayer interferometry. Anti-human IgG Fc Capture (AHC) biosensors (Forte Bio, Part No: 18-5064) were hydrated in assay buffer (1×PBS, 0.1% BSA, 0.02% Tween-20, pH 7.2) and preconditioned in 100 mM Glycine pH 1.5. A baseline was established in the assay buffer for 120 seconds. AHC biosensors were then immobilized with UniAbs™ at a concentration of 5 μg/mL for 120 seconds. Another baseline (120 seconds) was established in the assay buffer. Next, they were then dipped into a 7-point, 1:2 dilution series of the human CD22 protein in the assay buffer, starting from 250 nM. The last well of the analyte column contained only assay buffer to test for non-specific binding between the buffer and the loaded biosensors, and was used as a reference well. Association was observed for 600 seconds, followed by dissociation for 900 seconds. Data analysis was performed using Octet Data Analysis v9.0 (ForteBio). Binding kinetics were analyzed using a standard 1:1 binding model.

CD22 Cell Binding

Binding to CD22 positive cells was assessed by flow cytometry (Guava easyCyte 8HT, EMD Millipore) using the Daudi cell line (ATCC). Briefly, 100,000 target cells were stained with a dilution series of purified UniAbs™ for 30 minutes at 4° C. Following incubation, the cells were washed twice with flow cytometry buffer (1×PBS, 1% BSA, 0.1% NaN$_3$) and stained with goat F(ab')$_2$ anti-human IgG conjugated to R-phycoerythrin (PE) (Southern Biotech, cat. #2042-09) to detect cell-bound antibodies. After a 20-minute incubation at 4° C., the cells were washed twice with flow cytometry buffer and then mean fluorescence intensity (MFI) was measured by flow cytometry. EC50 values were calculated using GraphPad Prism 7. Binding to cynomolgus CD22 positive cells was determined using the same protocol with the following modifications: the target cells were from CHO cells stably transfected to express the extracellular domain of cynomolgus CD22 and each antibody was tested at a single concentration (~1.7 μg/mL) so EC50 values were not calculated.

Example 1: Genetically Engineered Rats Expressing Heavy Chain-Only Antibodies

A 'human-rat' IgH locus was constructed and assembled in several parts. This involved the modification and joining of rat C region genes downstream of human J$_H$s and subsequently, the upstream addition of the human V$_H$6-D-segment region. Two BACs with separate clusters of human V$_H$ genes [BAC6 and BAC3] were then co-injected with the BAC termed Georg, encoding the assembled and modified region comprising human V$_H$6, all Ds, all J$_H$s, and modified rat Cγ2a/1/2b (ΔC$_H$1).

Transgenic rats carrying artificial heavy chain immunoglobulin loci in unrearranged configuration were generated. The IgG2a(ΔC$_H$1), IgG1(ΔC$_H$1), IgG2b(ΔC$_H$1) genes lacked the C$_H$1 segment. The constant region genes IgE, IgA and 3' enhancer were included in Georg BAC. RT-PCR and serum analysis (ELISA) of transgenic rats revealed productive rearrangement of transgenic immunoglobulin loci and expression of heavy chain-only antibodies of various isotypes in serum. Transgenic rats were cross-bred with rats with mutated endogenous heavy chain and light chain loci previously described in US patent publication 2009/0098134 A1. Analysis of such animals demonstrated inactivation of rat immunoglobulin heavy and light chain expression and high level expression of heavy chain antibodies with variable regions encoded by human V, D, and J genes Immunization of transgenic rats resulted in production of high titer serum responses of antigen-specific heavy chain antibodies. These transgenic rats expressing heavy chain antibodies with a human VDJ region were called UniRats™.

Example 2: Immunization

Immunization with Recombinant Extracellular Domain of CD22.

Twelve UniRat animals (6 HC27, 6 HC28) were immunized with recombinant human CD22 protein. The animals were immunized according to standard protocol using a Titermax/Alhydrogel adjuvant. Recombinant extracellular domain of CD22 was purchased from R&D Systems and was diluted with sterile saline and combined with adjuvant. The immunogen was combined with Titermax and Alhydrogel adjuvants. The first immunization (priming) with immunogen in Titermax was administered in the left and right legs. Subsequent boosting immunizations were done in the presence of Alhydrogel and three days before harvest boosts were performed with immunogens in PBS. Serum was collected from rats at the final bleed to determine serum titers.

Serum Titer Results

Figure 17:
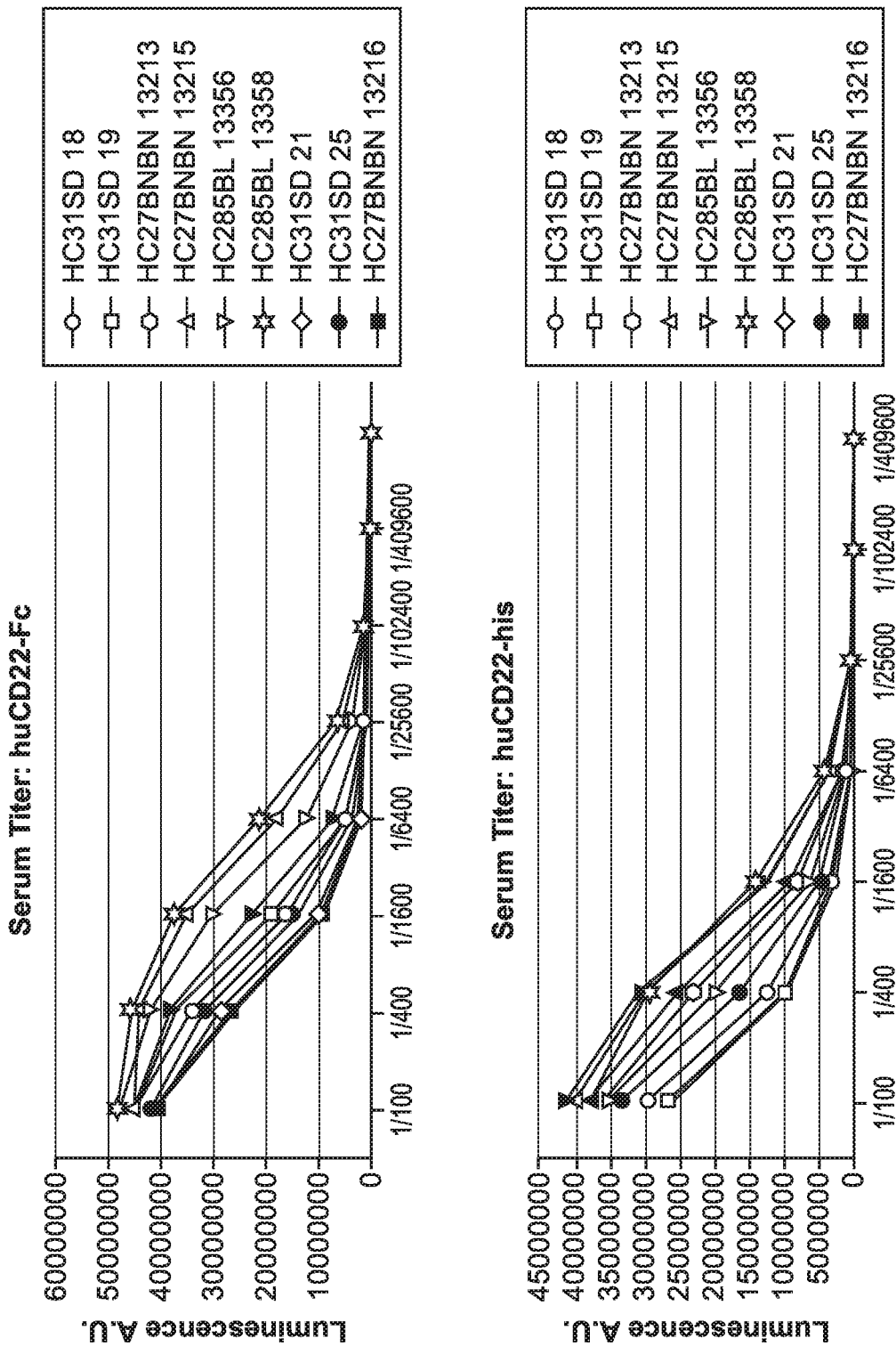
FIG. 17 is a series of graphs showing serum titer as a function of dilution.
Figure 17:
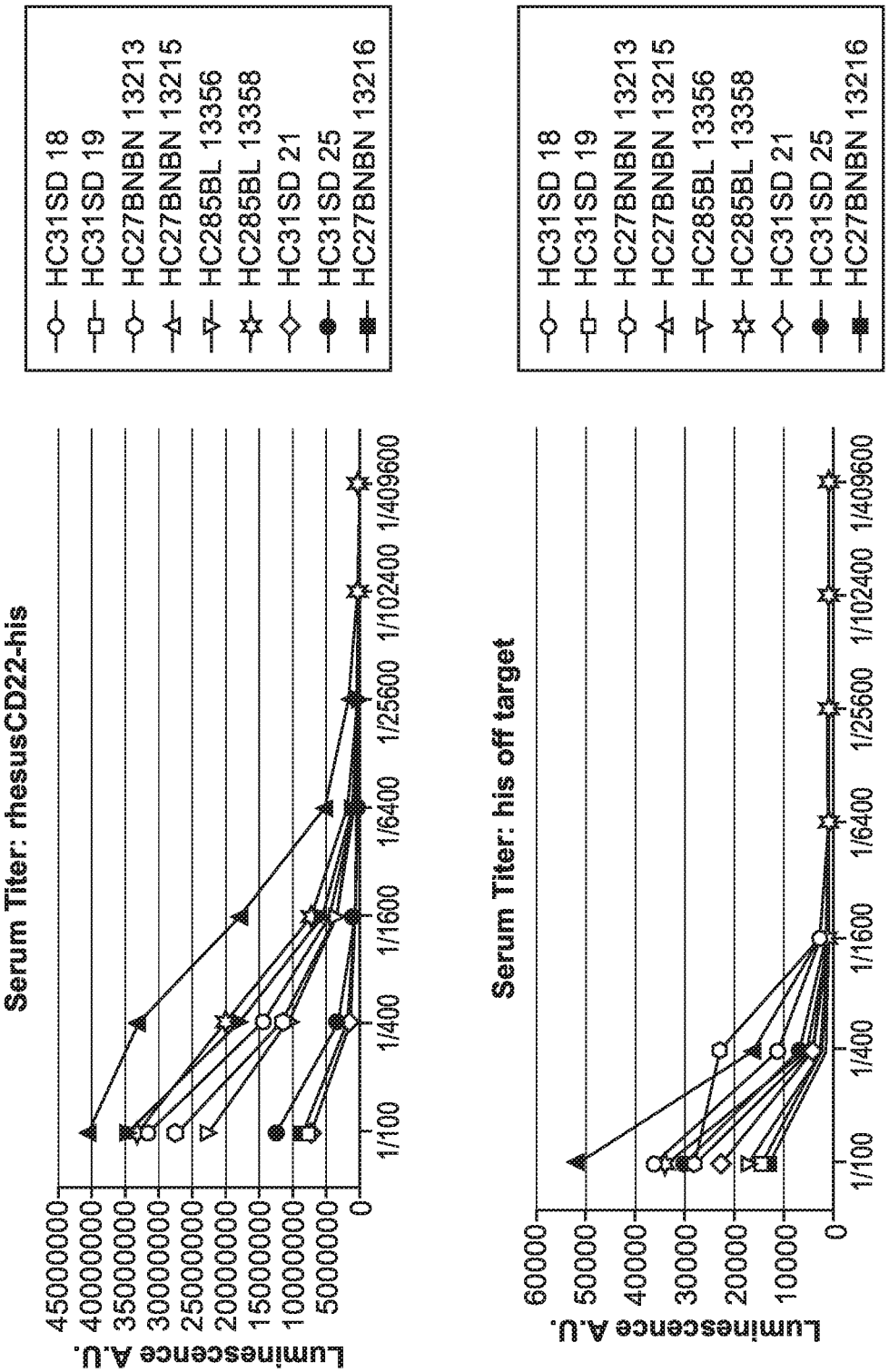

Serum titer summary information is shown in FIG. 17. In the graphs depicted in FIG. 17, each line represents an individual animal. The legends of the graphs show the ID number of each individual animal Binding activity for an 8-point dilution series of serum was tested by ELISA against a huCD22+Fc protein, huCD22+His tag, rhesus CD22+His tag protein, and a His tag off-target protein. Among this group of animals, a range of serum reactivity levels to both human and rhesus CD22 protein was observed. A serum response to the His protein tag was also observed.

Example 3: Binding to CD22-Expressing Cell Lines

FIG. 16 summarizes target binding activity of the anti-CD22 heavy chain-only antibodies described herein. Column 1 indicates the Clone ID number of the anti-CD22 heavy chain-only antibody. Column 2 indicates the binding affinity to protein (KD) measured in molarity. Column 3 indicates the dissociation constant of binding to protein (K-off rate) measured in seconds. Column 4 indicates binding to Daudi cells measured as fold over background MFI signal. Column 5 indicates binding to CHO cells stably expressing cyno CD22 measured as fold over background MFI signal. Column 6 indicates binding to CHO cells that do not express CD22 protein measured as fold over background MFI signal.

Example 4: T Cell Mediated Cytotoxicity of CD22 Positive Cells Using Resting Human Pan T Cells Unstimulated human T cells were incubated with CD22 positive cells (Daudi) and different concentrations of bispecific antibodies. After 48 hours, flow cytometry was performed on the cells to measure cytotoxicity. Supernatants from the cell culture were used to measure release of the cytokine IL-2. POS CTRL antibody refers to an antibody which comprises the same anti-CD22 arm, but a stronger affinity anti-CD3 arm. Results are provided in FIG. 1A and FIG. 1B.

Figure 2A:
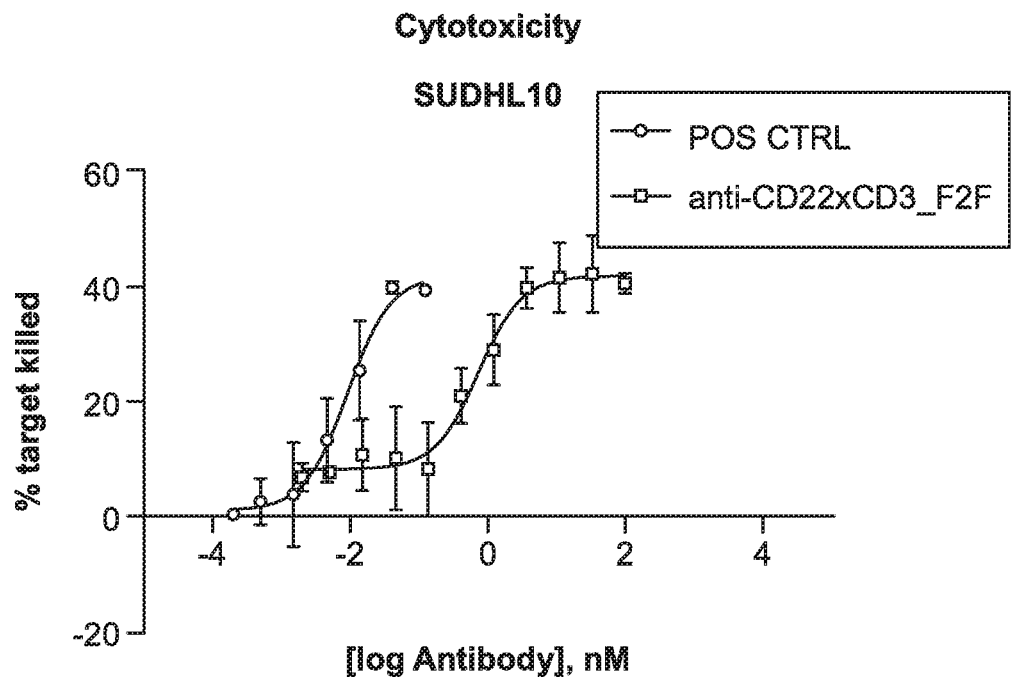
FIG. 2A is a graph depicting T cell mediated cytotoxicity of CD22 positive cells (SUDHL10) using resting human pan T cells.
Figure 2B:
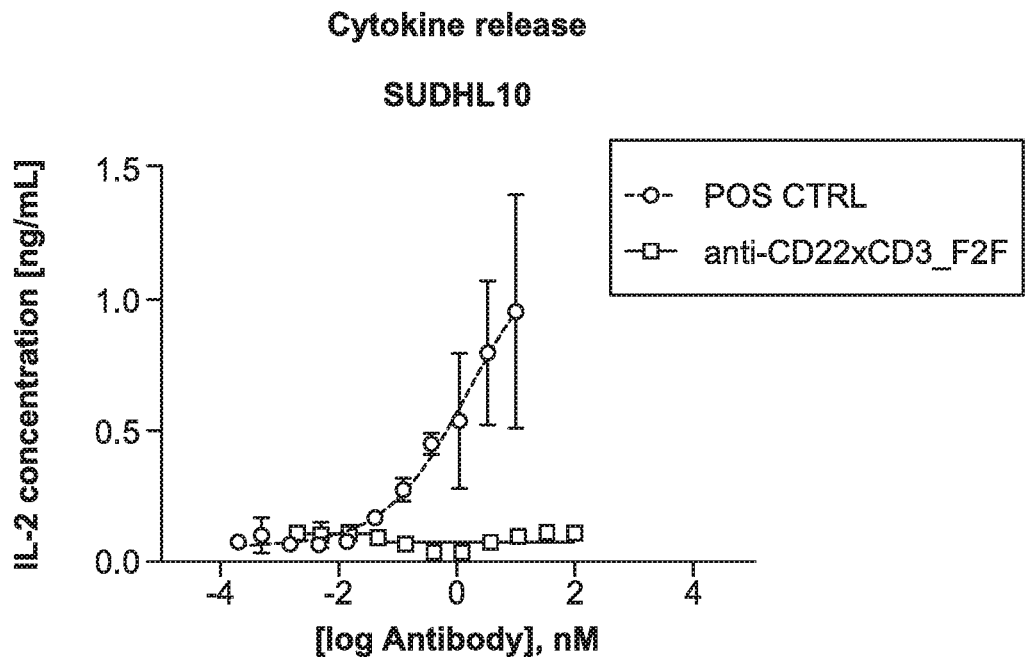
FIG. 2B is a graph depicting dose response curves of cytokine release by resting human pan T cells incubated with CD22 positive cells (SUDHL10) and treated with an anti-CD22xCD3_F2F multispecific binding compound and a positive control.

Unstimulated human T cells were incubated with CD22 positive cells (SUDHL10) and different concentrations of bispecific antibodies. After 72 hours, flow cytometry was performed on the cells to measure cytotoxicity. Supernatants from the cell culture were used to measure release of the cytokine IL-2. POS CTRL antibody refers to an antibody which comprises the same anti-CD22 arm, but a stronger affinity anti-CD3 arm. Results are provided in FIG. 2A and FIG. 2B.

Figure 3A:
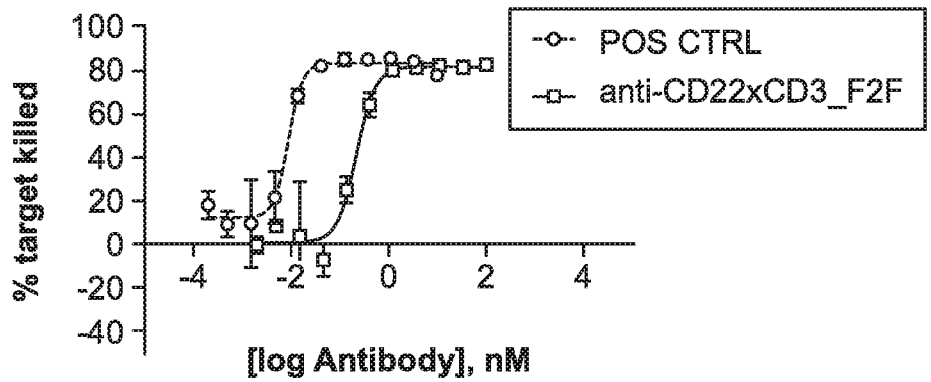
FIG. 3A shows a series of graphs depicting T cell mediated cytotoxicity of CD22 positive cells (RI-1) using resting human pan T cells.
Figure 3A:
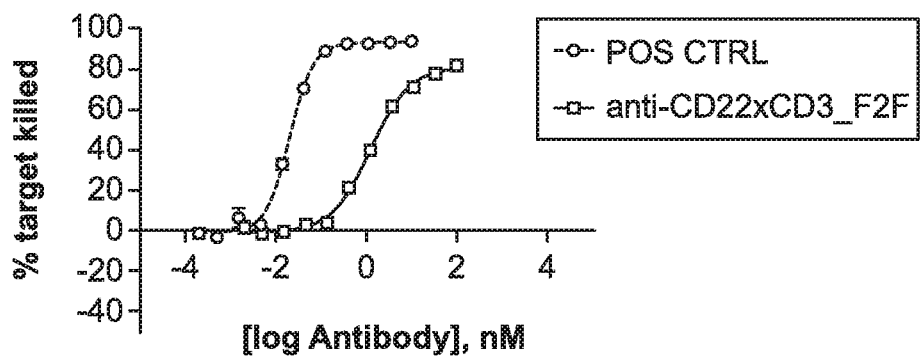
Figure 3A:
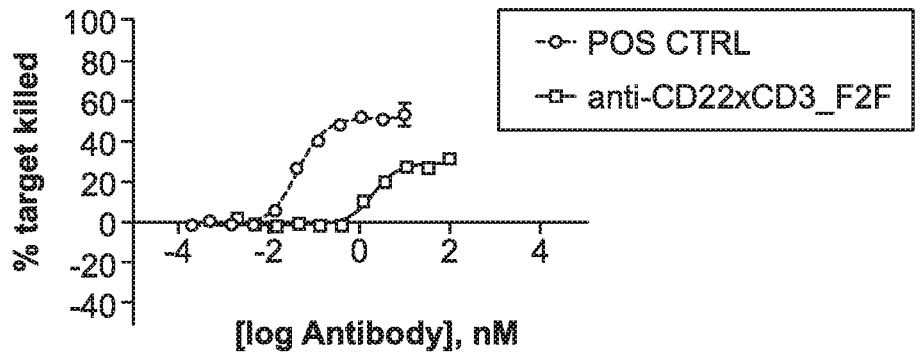
Figure 3B:
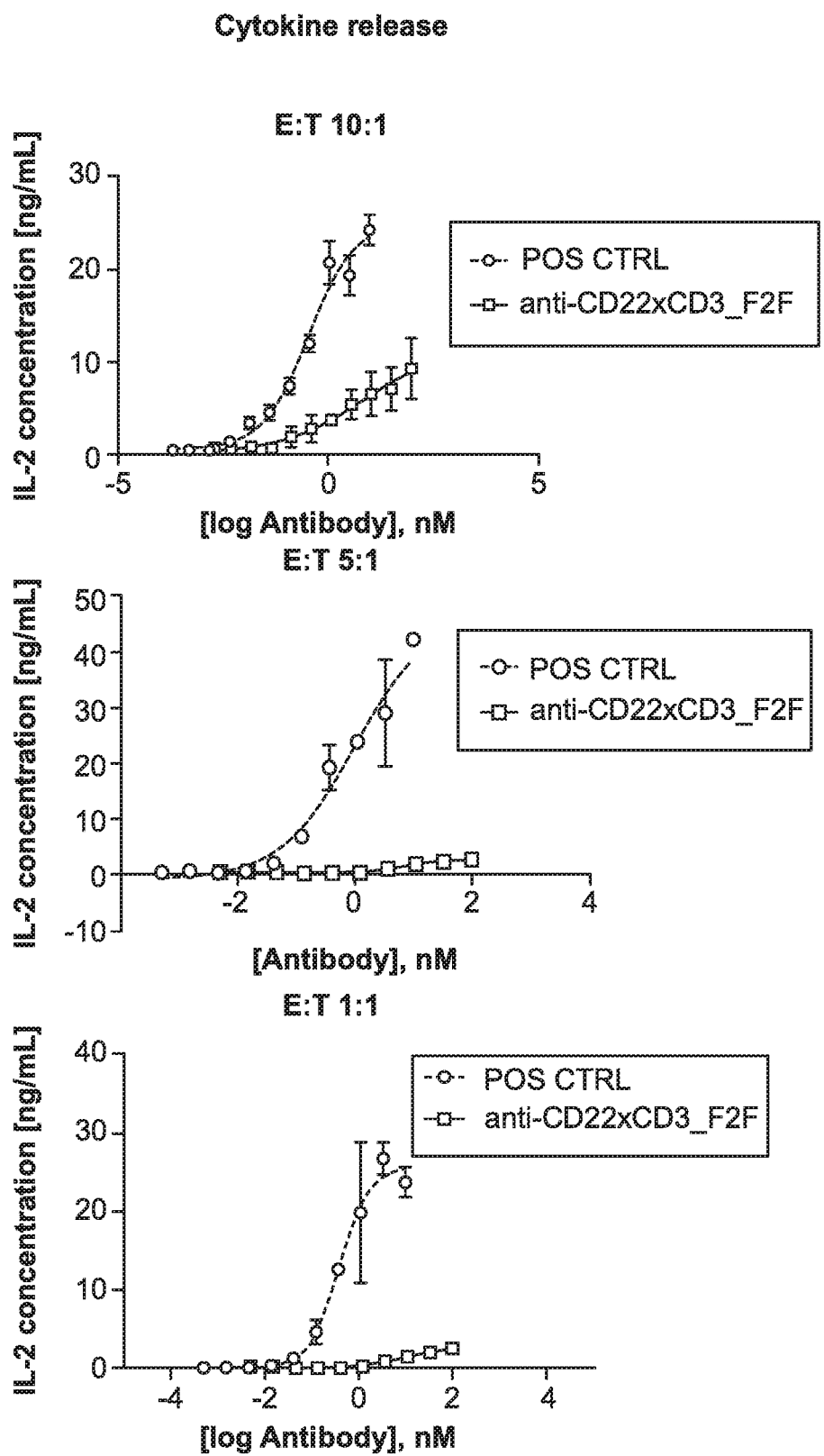
FIG. 3B shows a series of graphs depicting dose response curves of cytokine release by resting human pan T cells incubated with CD22 positive cells (RI-1) and treated with an anti-CD22xCD3_F2F multispecific binding compound and a positive control.

Unstimulated human T cells were incubated with CD22 positive DL-BCL cell line (RI-1) and different concentrations of bispecific antibodies with varying effector:target (E:T) cell ratios of 10:1, 5:1 or 1:1. After 72 hours, flow cytometry was performed on the cells to measure cytotoxicity. Supernatants from the cell culture were used to measure release of the cytokine IL-2. POS CTRL antibody refers to an antibody which comprises the same anti-CD22 arm, but a stronger affinity anti-CD3 arm. Data shows that the % cytotoxicity is dependent of E:T ratio. Results are provided in FIG. 3A and FIG. 3B.

Figure 4:
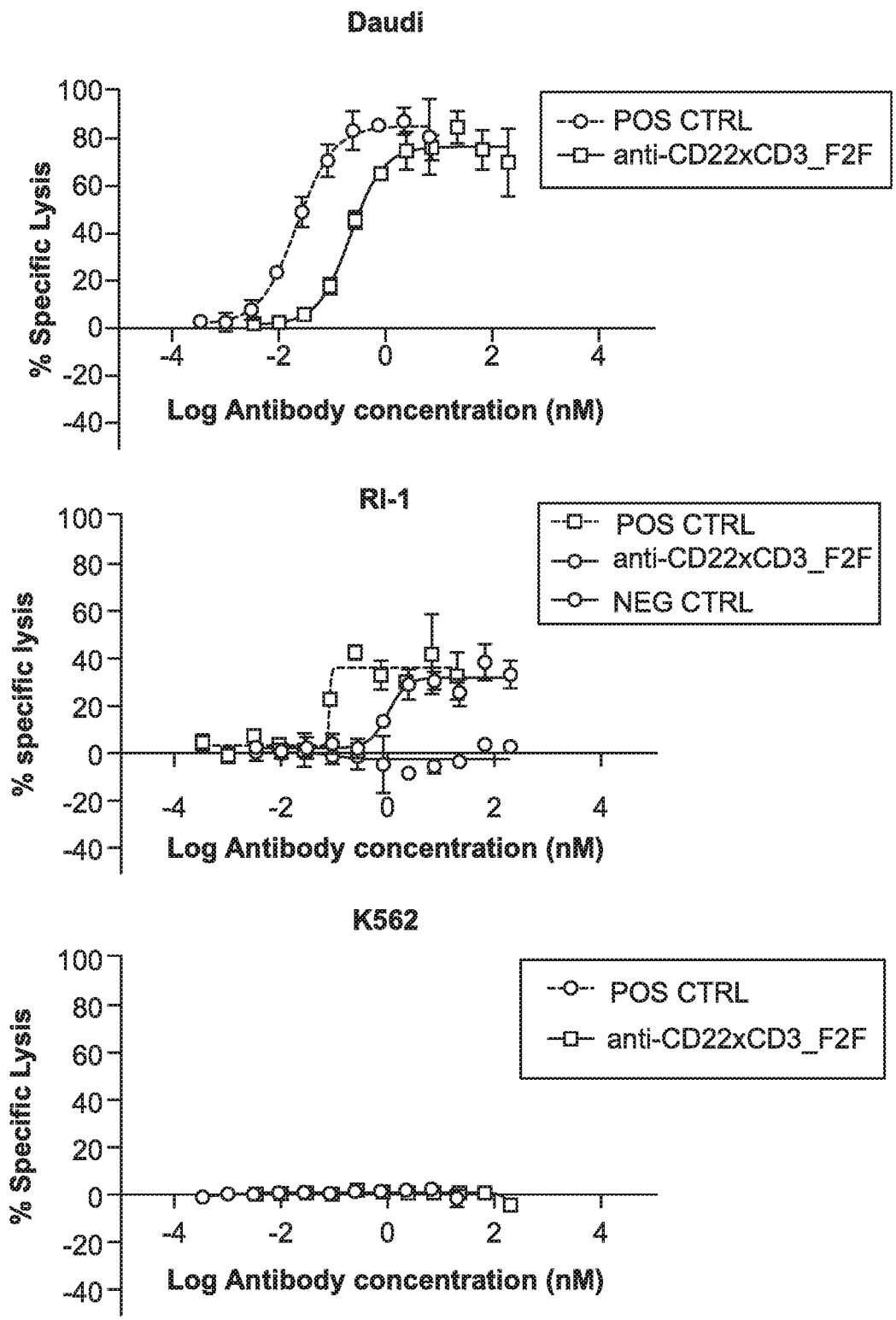
FIG. 4 shows a series of graphs depicting T cell mediated cytotoxicity of CD22 positive cells using activated human pan T cells.

Example 5: T Cell Mediated Cytotoxicity of CD22 Positive Cells Using Activated Human Pan T Cells Activated human T cells were incubated with CD22 positive cells (Daudi and RI-1) or a CD22 negative cell line (K562) and different concentrations of bispecific antibodies. Cell lysis was measured using a calcein-based fluorescence readout. The bispecific CD22×CD3_F2F binding compound specifically caused lysis of CD22+ cells, but not CD22-K562 cells. POS CTRL antibody refers to an antibody which comprises the same anti-CD22 arm, but a stronger affinity anti-CD3 arm. NEG CTRL refers to an antibody with a non-specific tumor arm and the same anti-CD3 arm as anti-CD3_F2F. Results are provided in FIG. 4.

Example 6: Cell Binding of Bispecific Antibodies Against CD22 and CD3

Figure 5:
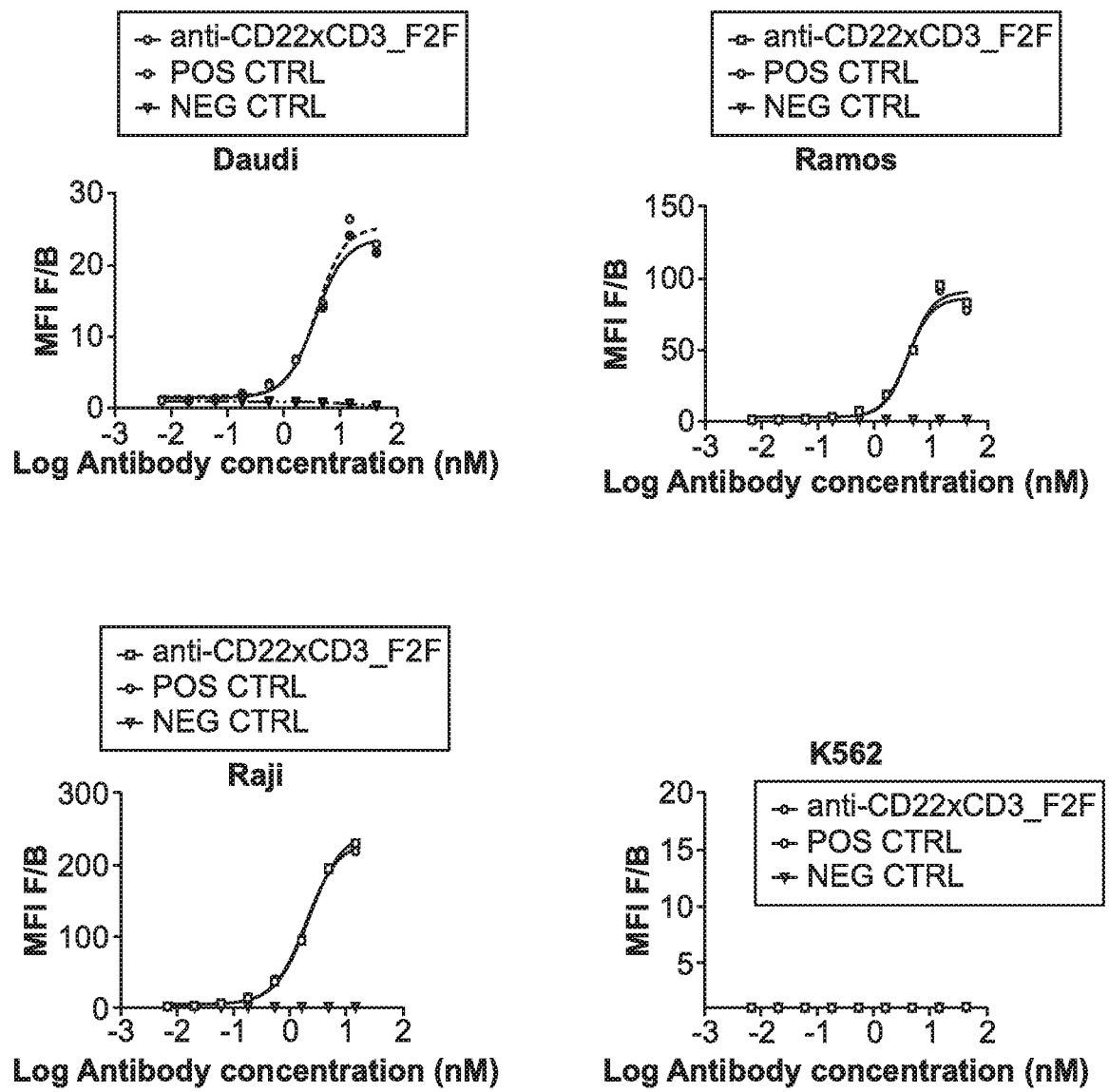
FIG. 5 shows a series of graphs depicting cell binding of bispecific antibodies against CD22 and CD3.

CD22 positive cells Daudi, Raji, Ramos and CD22 negative cells K562 were incubated with bispecific antibodies. Cell binding was measured by flow cytometry using an anti-human IgG secondary antibody reagent. Data shows that the bispecific antibodies bind to CD22+ cells, but not CD22-cells. POS CTRL antibody refers to an antibody which comprises the same anti-CD22 arm, but a stronger affinity anti-CD3 arm. NEG CTRL refers to an antibody with a non-specific tumor arm and the same anti-CD3 arm as anti-CD3_F2F. Results are provided in FIG. 5.

Example 7: In Vivo Efficacy Study with CD22-1×CD3_F2F in Daudi Xenografts

Figure 6:
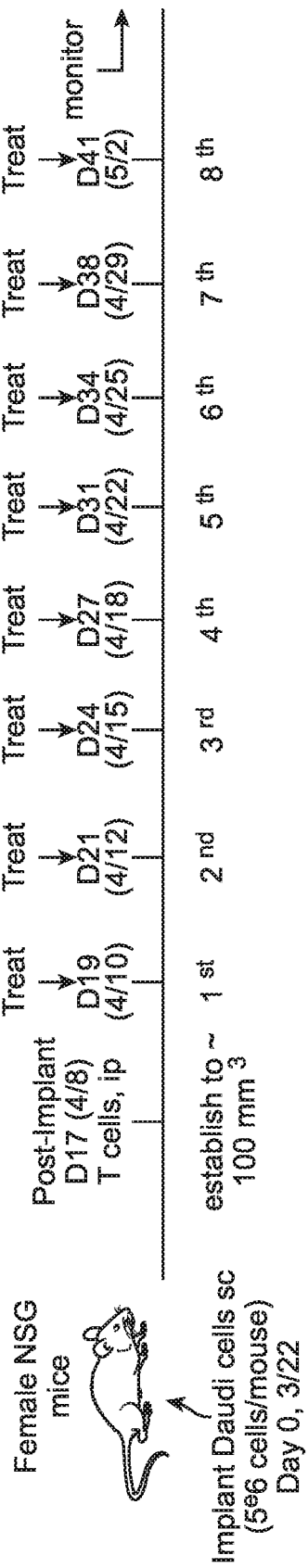
FIG. 6 shows a treatment plan to determine the in vivo efficacy of an anti-CD22xCD3_F2F multispecific binding compound in Daudi xenografts.
Figure 7:
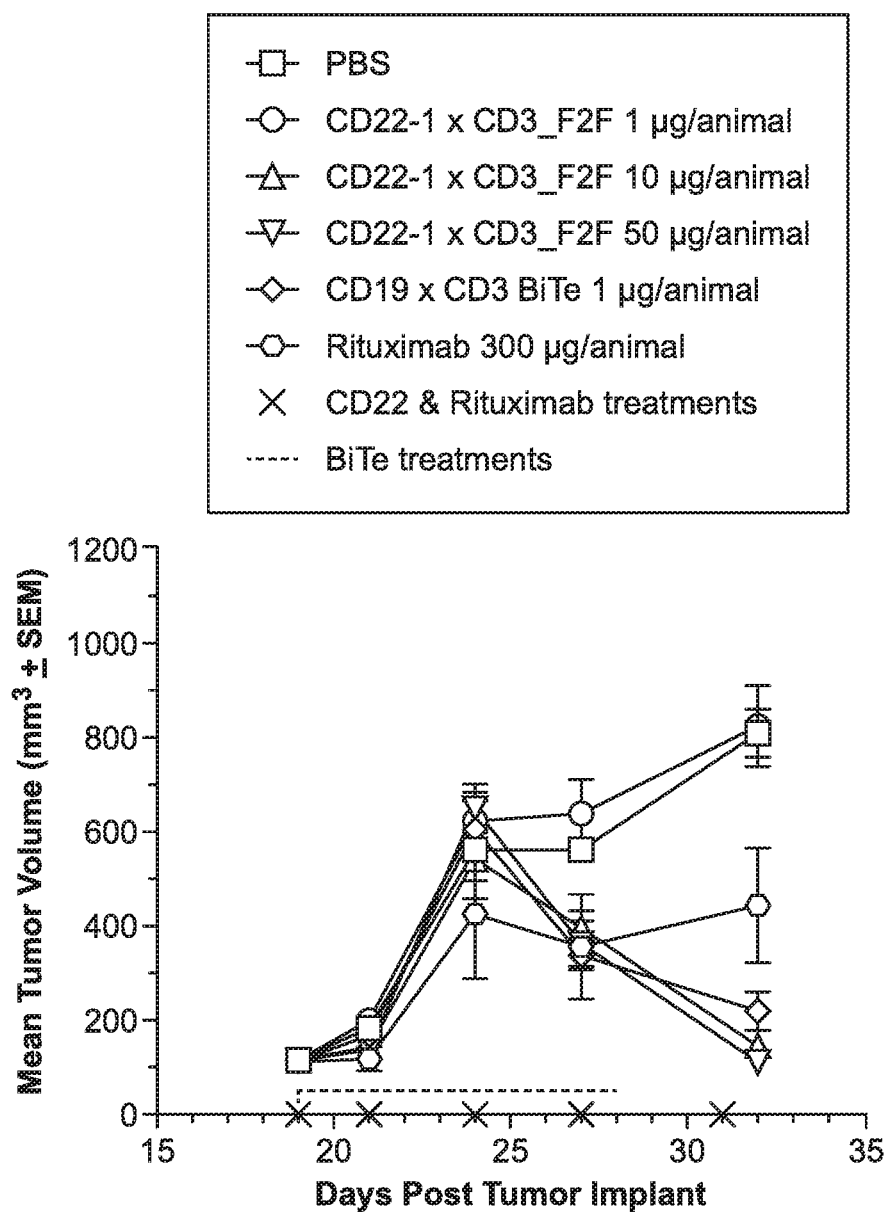
FIG. 7 is a graph depicting mean tumor volume as a function of days post tumor implant in mouse Daudi xenografts.
Figure 8:
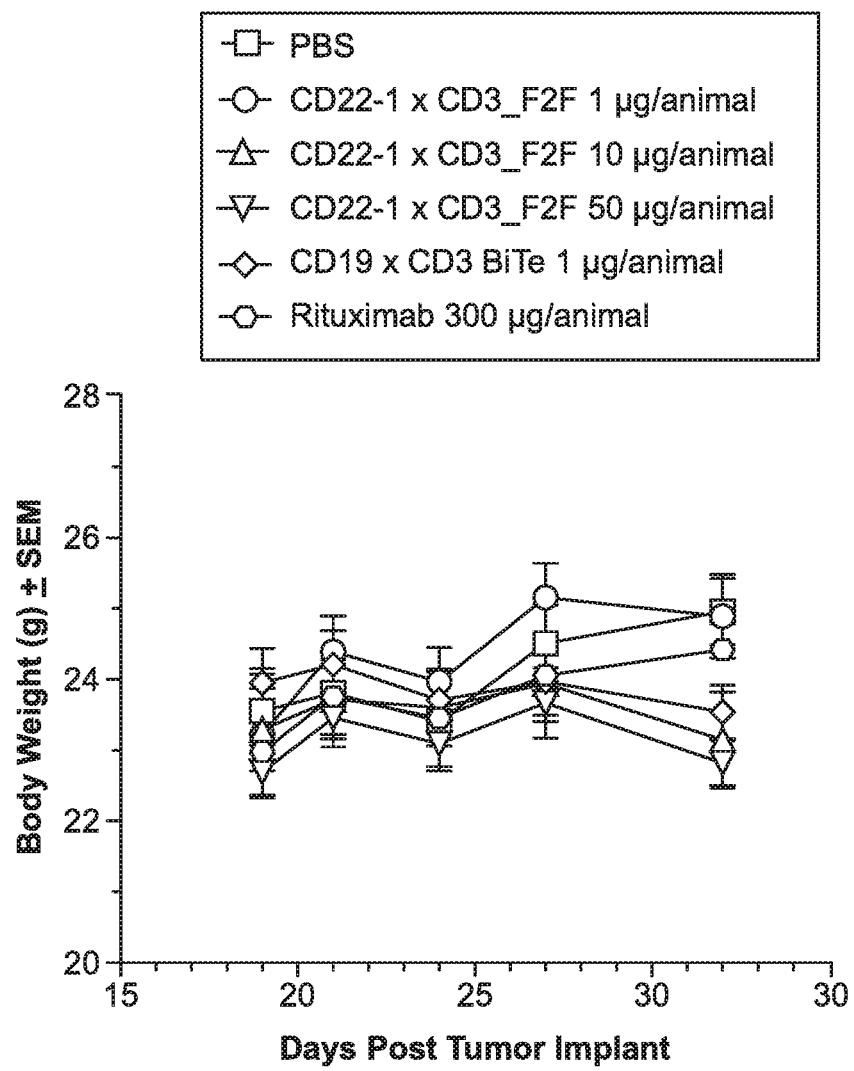
FIG. 8 is a graph depicting body weight as a function of days post tumor implant in mouse Daudi xenografts.
Figure 9:
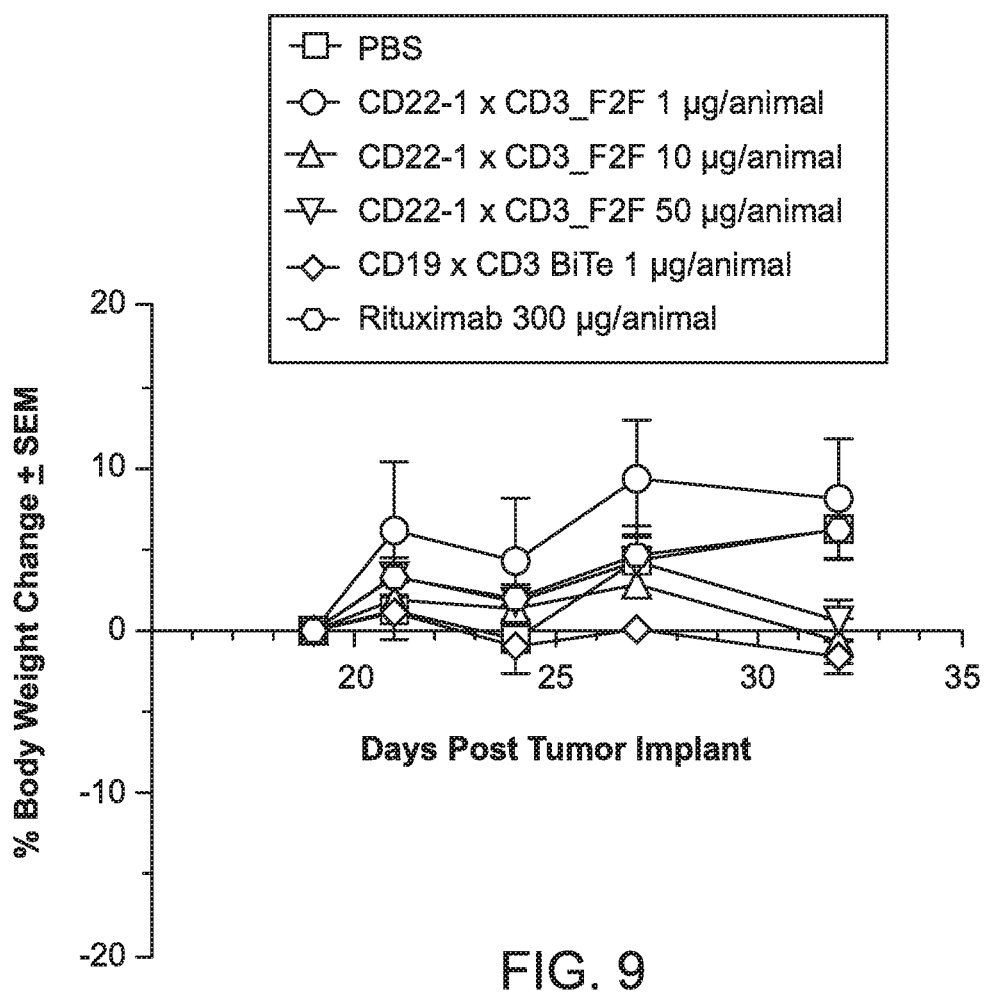
FIG. 9 is a graph depicting percent body weight change as a function of days post tumor implant in mouse Daudi xenografts.
Figure 10:
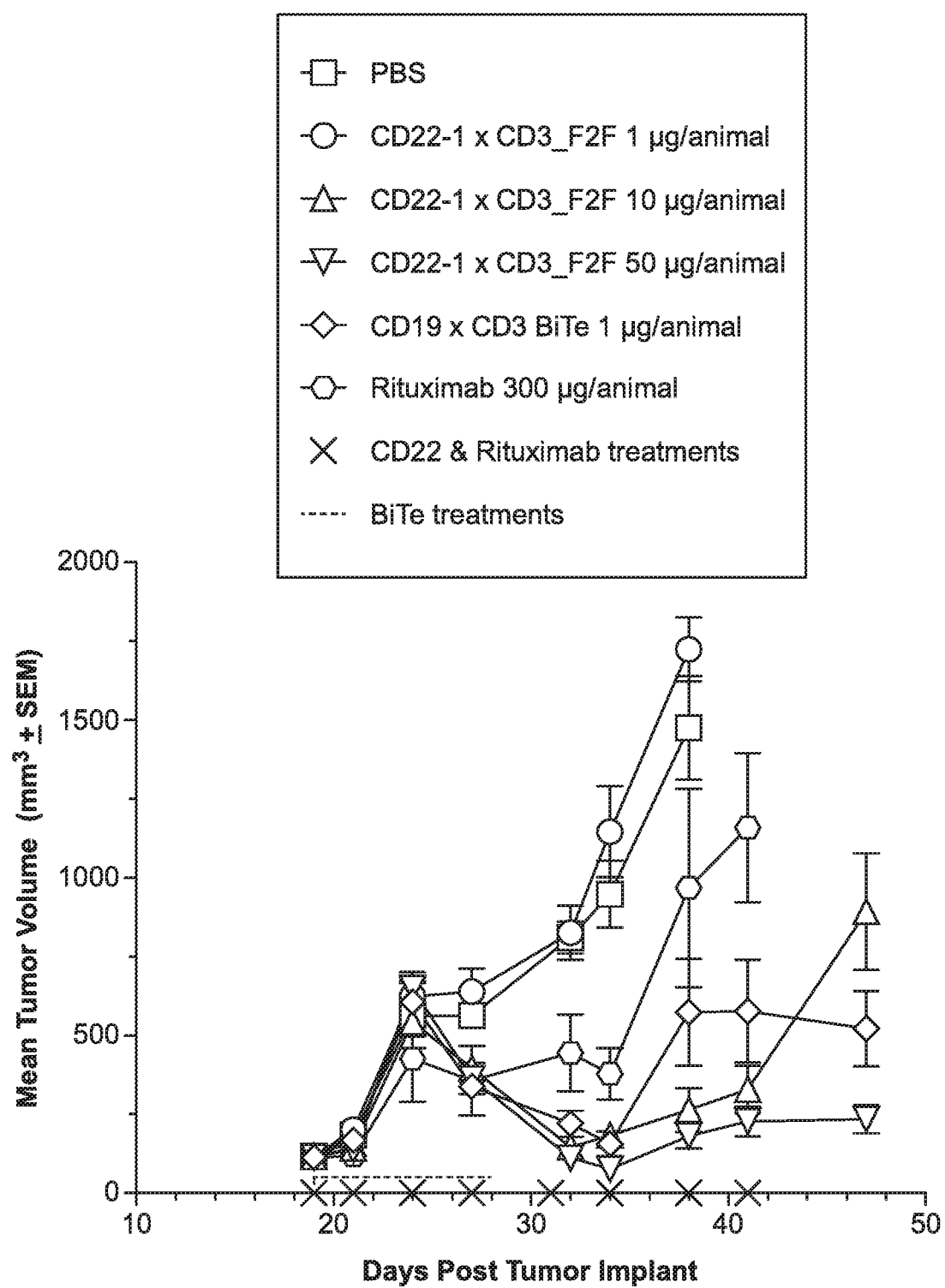
FIG. 10 is a graph depicting mean tumor volume as a function of days post tumor implant in mouse Daudi xenografts.
Figure 11:
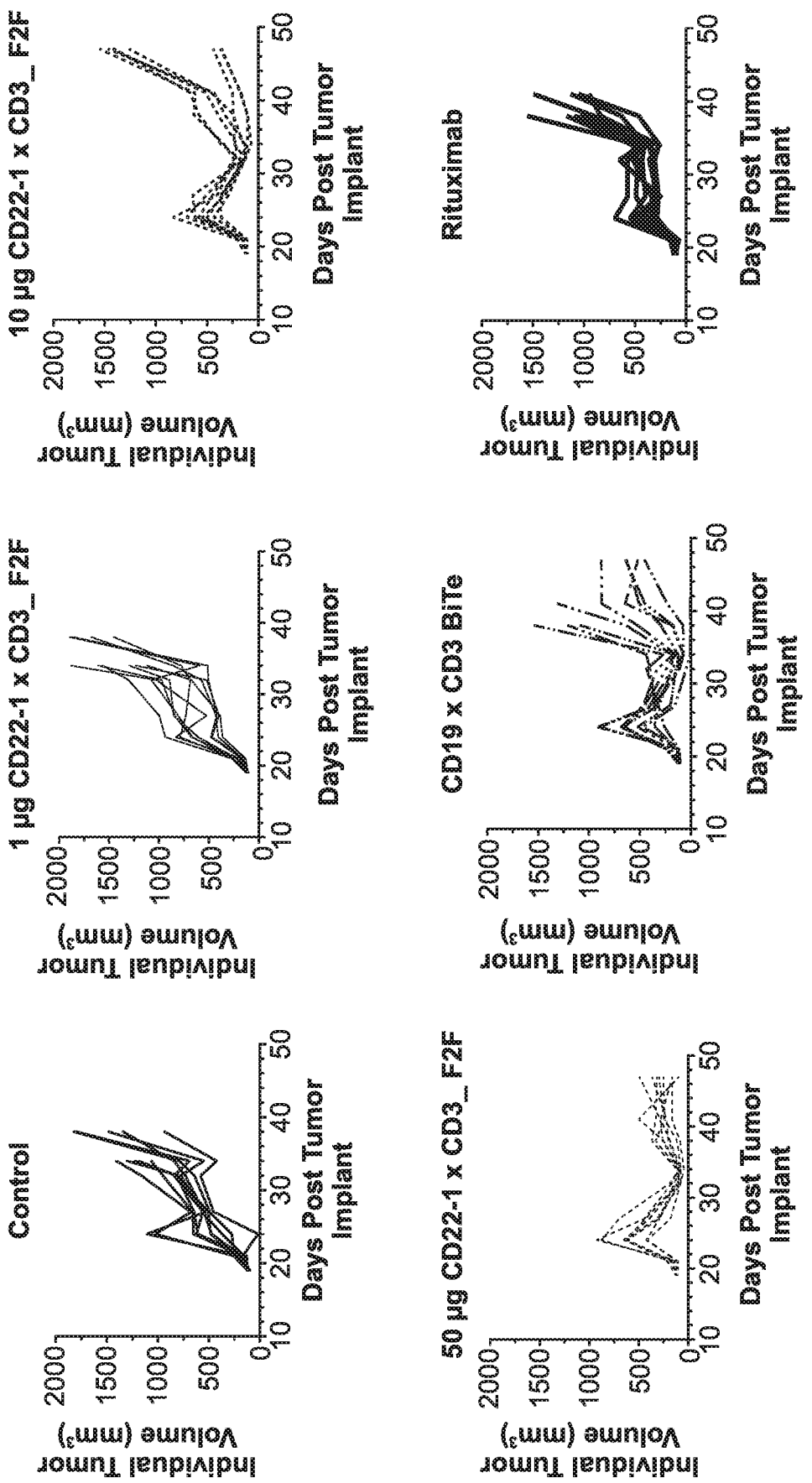
FIG. 11 shows a series of graphs depicting individual tumor measurements as a function of days post tumor implant in mouse Daudi xenografts.
Figure 12:
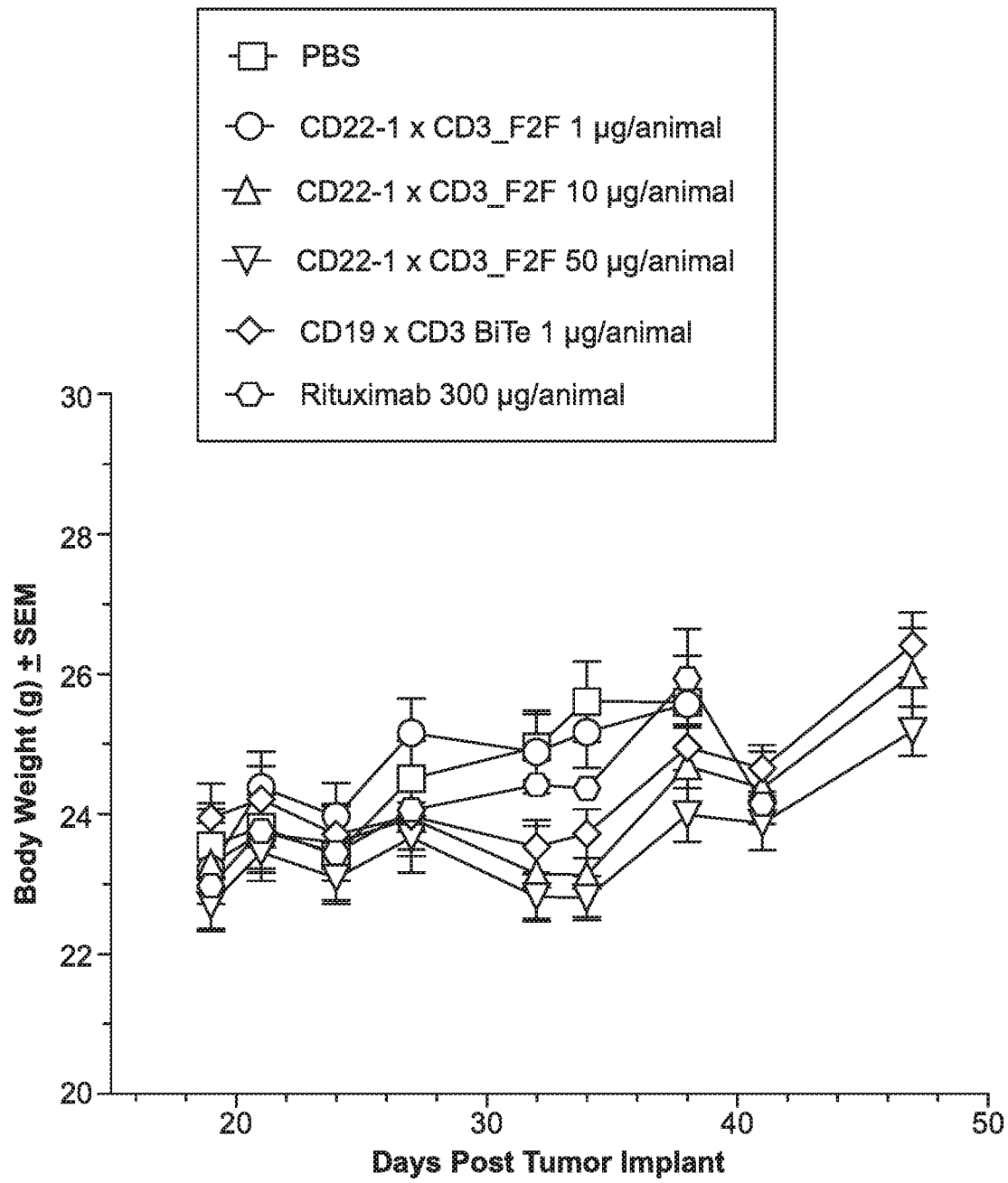
FIG. 12 is a graph depicting body weight as a function of days post tumor implant in mouse Daudi xenografts.
Figure 13:
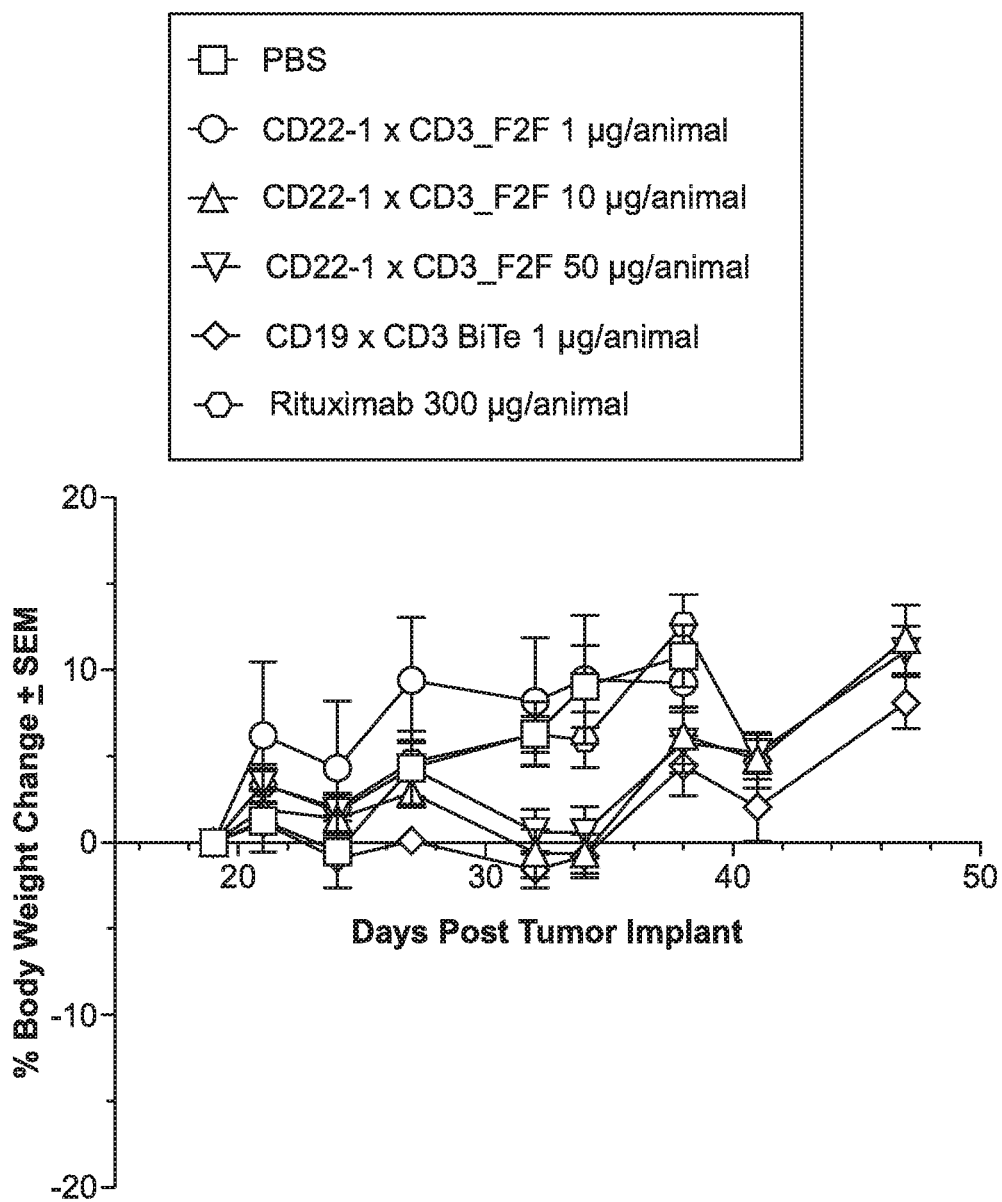
FIG. 13 is a graph depicting percent body weight change as a function of days post tumor implant in mouse Daudi xenografts.

To test the in vivo efficacy of CD22-1×CD3_F2F, varying doses of CD22-1×CD3_F2F were administered to female NSG mice implanted with Daudi cells (5e6 cells/mouse) as shown in FIG. 6. The treatment schedule is shown below in Table 7. Mean tumor volume, body weight, percent body weight change, and individual tumor volume were used to assess efficacy of treatment.

TABLE 7

| Sample treatment schedule | | | | | |
|---|---|---|---|---|---|
| Group | Treatment | Dose | Route | n | Schedule |
| 1 | PBS | — | ip | 10 | |
| 2 | CD22-1 × CD3_F2F | 0.05 (1 μg/mouse) | ip | 10 | 2×/wk (q3-4d) × 4 |
| 3 | CD22-1 × CD3_F2F | 0.5 (10 μg/mouse) | ip | 10 | 2×/wk (q3-4d) × 4 |

TABLE 7-continued

Sample treatment schedule

| Group | Treatment | Dose | Route | n | Schedule |
|---|---|---|---|---|---|
| 4 | CD22-1 × CD3_F2F | 2.5 (50 μg/mouse) | ip | 10 | 2×/wk (q3-4d) × 4 |
| 5 | CD19 × CD3 BiTe | 0.05 (1 μg/mouse) | ip | 10 | qd × 10 |
| 6 | Rituximab | 15 (300 μg/mouse) | ip | 10 | 2×/wk (q3-4d) × 4 |

The data from CD22-1×CD3_F2F are shown in FIGS. 7-13, compared to a negative control and Rituximab, and demonstrate the efficacy of CD22-1×CD3_F2F.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A multi-specific binding compound comprising a first binding unit having binding affinity to CD22 and a second binding unit having binding affinity to CD3, wherein the first binding unit having binding affinity to CD22 comprises a heavy chain variable region comprising:

(a) a CDR1 sequence of SEQ ID NO: 1, a CDR2 sequence of SEQ ID NO: 11, and a CDR3 sequence of SEQ ID NO: 18;

(b) a CDR1 sequence of SEQ ID NO: 1, a CDR2 sequence of SEQ ID NO: 12, and a CDR3 sequence of SEQ ID NO: 19; or (c) a CDR1 sequence of SEQ ID NO: 1, a CDR2 sequence of SEQ ID NO: 12, and a CDR3 sequence of SEQ ID NO: 20; and wherein the second binding unit comprises:

(a) a heavy chain variable region comprising a CDR1 sequence of SEQ ID NO: 85, a CDR2 sequence of SEQ ID NO: 86, and a CDR3 sequence of SEQ ID NO: 87; and (b) a light chain variable region comprising a CDR1 sequence of SEQ ID NO: 88, a CDR2 sequence of SEQ ID NO: 89, and a CDR3 sequence of SEQ ID NO: 90.

2. The multi-specific binding compound of claim 1, wherein the first binding unit having binding affinity to CD22 comprises a heavy chain variable region sequence having at least 95% identity to SEQ ID NO: 24.

3. The multi-specific binding compound of claim 2, wherein the first binding unit having binding affinity to CD22 comprises a heavy chain variable region sequence comprising SEQ ID NO: 24.

4. The multi-specific binding compound of claim 1, wherein the first binding unit having binding affinity to CD22 comprises a heavy chain variable region sequence having at least 95% identity to SEQ ID NO: 25.

5. The multi-specific binding compound of claim 4, wherein the first binding unit having binding affinity to CD22 comprises a heavy chain variable region sequence comprising SEQ ID NO: 25.

6. The multi-specific binding compound of claim 1, wherein the first binding unit having binding affinity to CD22 comprises a heavy chain variable region sequence having at least 95% identity to SEQ ID NO: 32.

7. The multi-specific binding compound of claim 6, wherein the first binding unit having binding affinity to CD22 comprises a heavy chain variable region sequence comprising SEQ ID NO: 32.

8. The multi-specific binding compound of claim 1, wherein the second binding unit having binding affinity to CD3 comprises a heavy chain variable region sequence having at least 95% identity to SEQ ID NO: 91.

9. The multi-specific binding compound of claim 8, wherein the second binding unit having binding affinity to CD3 comprises a heavy chain variable region sequence comprising SEQ ID NO: 91.

10. The multi-specific binding compound of claim 1, wherein the second binding unit having binding affinity to CD3 comprises a light chain variable region sequence having at least 95% identity to SEQ ID NO: 92.

11. The multi-specific binding compound of claim 10, wherein the second binding unit having binding affinity to CD3 comprises a light chain variable region sequence comprising SEQ ID NO: 92.

12. The multi-specific binding compound of claim 1, wherein the first binding unit having binding affinity to CD22 further comprises a heavy chain constant region sequence in the absence of a CH1 sequence.

13. The multi-specific binding compound of claim 1, comprising a human IgG4 Fc region.

14. The multi-specific binding compound of claim 13, wherein the human IgG4 Fc region is a silenced human IgG4 Fc region.

15. A polynucleotide encoding a multi-specific binding compound of claim 1.

16. A method for the treatment of a B-cell disorder characterized by expression of CD22, comprising administering to a subject with said disorder a multi-specific binding compound of claim 1.

17. The method of claim 16, wherein the B-cell disorder is non-Hodgkin's lymphoma (NHL).

18. The method of claim 16, wherein the B-cell disorder is B-cell chronic lymphocytic leukemia (B-cell CLL).

19. The method of claim 16, wherein the B-cell disorder is follicular lymphoma (FL).

20. The multi-specific binding compound of claim 13, wherein the human IgG4 Fc region comprises a hinge region mutation.

21. The multi-specific binding compound of claim 13, wherein the human IgG4 Fc region comprises a plurality of knobs-into-holes mutations.

22. The multi-specific binding compound of claim 13, wherein the human IgG4 Fc region comprises a C-terminal lysine.

23. The multi-specific binding compound of claim 13, wherein the human IgG4 Fc region does not comprise a C-terminal lysine.

24. A multi-specific binding compound comprising a first binding unit having binding affinity to CD22 and a second binding unit having binding affinity to CD3;
wherein the first binding unit having binding affinity to CD22 comprises a heavy chain variable region comprising a CDR1 sequence of SEQ ID NO: 1, a CDR2 sequence of SEQ ID NO: 12, and a CDR3 sequence of SEQ ID NO: 19; and
wherein the second binding unit comprises:
(a) a heavy chain variable region comprising a CDR1 sequence of SEQ ID NO: 85, a CDR2 sequence of SEQ ID NO: 86, and a CDR3 sequence of SEQ ID NO: 87; and
(b) a light chain variable region comprising a CDR1 sequence of SEQ ID NO: 88, a CDR2 sequence of SEQ ID NO: 89, and a CDR3 sequence of SEQ ID NO: 90.

25. The multi-specific binding compound of claim 24, wherein the first binding unit having binding affinity to CD22 comprises a heavy chain variable region sequence having at least 95% identity to SEQ ID NO: 25.

26. The multi-specific binding compound of claim 24, wherein the first binding unit having binding affinity to CD22 comprises a heavy chain variable region sequence comprising SEQ ID NO: 25.

27. The multi-specific binding compound of claim 24, wherein the second binding unit having binding affinity to CD3 comprises a heavy chain variable region sequence having at least 95% identity to SEQ ID NO: 91.

28. The multi-specific binding compound of claim 27, wherein the second binding unit having binding affinity to CD3 comprises a heavy chain variable region sequence comprising SEQ ID NO: 91.

29. The multi-specific binding compound of claim 24, wherein the second binding unit having binding affinity to CD3 comprises a light chain variable region sequence having at least 95% identity to SEQ ID NO: 92.

30. The multi-specific binding compound of claim 29, wherein the second binding unit having binding affinity to CD3 comprises a light chain variable region sequence comprising SEQ ID NO: 92.

31. The multi-specific binding compound of claim 24, wherein the first binding unit having binding affinity to CD22 further comprises a heavy chain constant region sequence in the absence of a CH1 sequence.

32. The multi-specific binding compound of claim 24, comprising a human IgG4 Fc region.

33. The multi-specific binding compound of claim 32, wherein the human IgG4 Fc region is a silenced human IgG4 Fc region.

34. The multi-specific binding compound of claim 32, wherein the human IgG4 Fc region comprises a hinge region mutation.

35. The multi-specific binding compound of claim 32, wherein the human IgG4 Fc region comprises a plurality of knobs-into-holes mutations.

36. The multi-specific binding compound of claim 32, wherein the human IgG4 Fc region comprises a C-terminal lysine.

37. The multi-specific binding compound of claim 32, wherein the human IgG4 Fc region does not comprise a C-terminal lysine.

38. A polynucleotide encoding a multi-specific binding compound of claim 24.

39. A method for the treatment of a B-cell disorder characterized by expression of CD22 comprising administering to a subject with said disorder a multi-specific binding compound of claim 24.

40. The method of claim 39, wherein the B-cell disorder is non-Hodgkin's lymphoma (NHL).

41. The method of claim 39, wherein the B-cell disorder is B-cell chronic lymphocytic leukemia (B-cell CLL).

42. The method of claim 39, wherein the B-cell disorder is follicular lymphoma (FL).

43. A heavy chain-only antibody binding to CD22 comprising a heavy chain variable region comprising:
  (a) a CDR1 sequence of SEQ ID NO: 1, a CDR2 sequence of SEQ ID NO: 11, and a CDR3 sequence of SEQ ID NO: 18; or
  (b) a CDR1 sequence of SEQ ID NO: 1, a CDR2 sequence of SEQ ID NO: 12, and a CDR3 sequence of SEQ ID NO: 19; or
  (c) a CDR1 sequence of SEQ ID NO: 1, a CDR2 sequence of SEQ ID NO: 12, and a CDR3 sequence of SEQ ID NO: 20.

44. The heavy chain-only antibody of claim 43, wherein the CDR1, CDR2, and CDR3 sequences are present in a human VH framework.

45. The heavy chain-only antibody of claim 43, wherein the heavy chain variable region comprises a sequence having at least 95% identity to SEQ ID NO: 24.

46. The heavy chain-only antibody of claim 43, wherein the heavy chain variable region sequence comprises SEQ ID NO: 24.

47. The heavy chain-only antibody of claim 43, wherein the heavy chain variable region comprises a sequence having at least 95% identity to SEQ ID NO: 25.

48. The heavy chain-only antibody of claim 43, wherein the heavy chain variable region sequence comprises SEQ ID NO: 25.

49. The heavy chain-only antibody of claim 43, wherein the heavy chain variable region comprises a sequence having at least 95% identity to SEQ ID NO: 32.

50. The heavy chain-only antibody of claim 43, wherein the heavy chain variable region sequence comprises SEQ ID NO: 32.

51. The heavy chain-only antibody of claim 43, further comprising a heavy chain constant region sequence.

52. The heavy chain-only antibody of claim 43, wherein the heavy chain constant region sequence lacks a CH1 sequence.

53. The heavy chain-only antibody of claim 51, wherein the heavy chain constant region sequence comprises a CH2 domain and a CH3 domain.

54. The heavy chain-only antibody of claim 43, further comprising a human IgG4 Fc region.

55. The heavy chain-only antibody of claim 54, wherein the human IgG4 Fc region is a variant human IgG4 Fc region.

56. The heavy chain-only antibody of claim 54, wherein the human IgG4 Fc region comprises a hinge region mutation.

57. The heavy chain-only antibody of claim 54, wherein the human IgG4 Fc region comprises a plurality of knobs-into-holes mutations.

58. The heavy chain-only antibody of claim 54, wherein the human IgG4 Fc region comprises a C-terminal lysine.

59. The heavy chain-only antibody of claim 54, wherein the human IgG4 Fc region does not comprise a C-terminal lysine.

60. The heavy chain-only antibody of claim 43, which is multi-specific.

61. The heavy chain-only antibody of claim 60, which is bispecific.

62. The heavy chain-only antibody of claim 60, having binding affinity to an effector cell.

63. The heavy chain-only antibody of claim 60, having binding affinity to a T-cell antigen.

64. The heavy chain-only antibody of claim 60, having binding affinity to CD3.

65. A polynucleotide encoding the heavy chain-only antibody of claim 43.

66. A medicine or pharmaceutical composition comprising the heavy chain-only antibody of claim 43 for treating a B-cell disorder characterized by expression of CD22.

67. A multi-specific or bispecific antibody comprising the heavy chain-only antibody of claim 43.

68. The heavy chain-only antibody of claim 43 for treating a B-cell disorder characterized by expression of CD22.

69. The heavy chain-only antibody of claim 68, wherein the disorder is selected from the group consisting of: diffuse large B cell lymphoma (DLBCL), non-Hodgkin's lymphoma (NHL), systemic lupus erythematosus (SLE), rheumatoid arthritis (RA), and multiple sclerosis (MS).

70. The heavy chain-only antibody of claim 68, wherein the disorder is B-cell chronic lymphocytic leukemia.

71. The heavy chain-only antibody of claim 68, wherein the disorder is follicular lymphoma.

72. The heavy chain-only antibody of claim 43, which is in a chimeric antigen receptor format.

73. A heavy chain-only antibody binding to CD22 comprising a heavy chain variable region comprising a CDR1 sequence of SEQ ID NO: 1, a CDR2 sequence of SEQ ID NO: 12, and a CDR3 sequence of SEQ ID NO: 19.

74. The heavy chain-only antibody of claim 73, wherein the CDR1, CDR2, and CDR3 sequences are present in a human VH framework.

75. The heavy chain-only antibody of claim 73, wherein the heavy chain variable region comprises a sequence having at least 95% identity to SEQ ID NO: 25.

76. The heavy chain-only antibody of claim 73, wherein the heavy chain variable region sequence comprises SEQ ID NO: 25.

77. The heavy chain-only antibody of claim 73, further comprising a heavy chain constant region sequence.

78. The heavy chain-only antibody of claim 77, wherein the heavy chain constant region sequence lacks a CH1 sequence.

79. The heavy chain-only antibody of claim 77, wherein the heavy chain constant region sequence comprises a CH2 domain and a CH3 domain.

80. The heavy chain-only antibody of claim 73, further comprising a human IgG4 Fc region.

81. The heavy chain-only antibody of claim 80, wherein the human IgG4 Fc region is a variant human IgG4 Fc region.

82. The heavy chain-only antibody of claim 80, wherein the human IgG4 Fc region comprises a hinge region mutation.

83. The heavy chain-only antibody of claim 80, wherein the human IgG4 Fc region comprises a plurality of knobs-into-holes mutations.

84. The heavy chain-only antibody of claim 80, wherein the human IgG4 Fc region comprises a C-terminal lysine.

85. The heavy chain-only antibody of claim 80, wherein the human IgG4 Fc region does not comprise a C-terminal lysine.

86. The heavy chain-only antibody of claim 73, which is multi-specific.

87. The heavy chain-only antibody of claim 86, which is bispecific.

88. The heavy chain-only antibody of claim 86, having binding affinity to an effector cell.

89. The heavy chain-only antibody of claim 86, having binding affinity to a T-cell antigen.

90. The heavy chain-only antibody of claim 86, having binding affinity to CD3.

91. A polynucleotide encoding the heavy chain-only antibody of claim 73.

92. A medicine or pharmaceutical composition comprising the heavy chain-only antibody of claim 73 for treating a B-cell disorder characterized by expression of CD22.

93. A multi-specific or bispecific antibody comprising the heavy chain-only antibody of claim 73.

94. The heavy chain-only antibody of claim 73 for treating a B-cell disorder characterized by expression of CD22.

95. The heavy chain-only antibody of claim 94, wherein the disorder is selected from the group consisting of: diffuse large B cell lymphoma (DLBCL), non-Hodgkin's lymphoma (NHL), systemic lupus erythematosus (SLE), rheumatoid arthritis (RA), and multiple sclerosis (MS).

96. The heavy chain-only antibody of claim 94, wherein the disorder is B-cell chronic lymphocytic leukemia.

97. The heavy chain-only antibody of claim 94, wherein the disorder is follicular lymphoma.

\* \* \* \* \*